United States Patent
Rustamzadeh

(10) Patent No.: US 10,631,842 B1
(45) Date of Patent: Apr. 28, 2020

(54) LATERAL RETRACTION SYSTEM FOR MINIMIZING MUSCLE DAMAGE IN SPINAL SURGERY

(71) Applicant: Edward Rustamzadeh, San Jose, CA (US)

(72) Inventor: Edward Rustamzadeh, San Jose, CA (US)

(*) Notice: Subject to any disclaimer, the term of this patent is extended or adjusted under 35 U.S.C. 154(b) by 0 days.

(21) Appl. No.: 16/669,013

(22) Filed: Oct. 30, 2019

Related U.S. Application Data

(60) Continuation-in-part of application No. 16/533,368, filed on Aug. 6, 2019, which is a continuation of
(Continued)

(51) Int. Cl.
*A61B 17/02* (2006.01)
*A61M 29/00* (2006.01)
(Continued)

(52) U.S. Cl.
CPC ........ *A61B 17/0218* (2013.01); *A61B 17/025* (2013.01); *A61B 17/0206* (2013.01);
(Continued)

(58) Field of Classification Search
CPC ........ A61B 2017/0262; A61B 17/0206; A61B 2017/00022
See application file for complete search history.

(56) References Cited

U.S. PATENT DOCUMENTS

| | | | |
|---|---|---|---|
| 6,285,902 B1 | 9/2001 | Kienzle, III | |
| 6,517,563 B1 | 2/2003 | Paolitto | |

(Continued)

FOREIGN PATENT DOCUMENTS

| | | |
|---|---|---|
| AU | 2012299061 B2 | 2/2013 |
| CA | 2 845 332 A1 | 2/2013 |

(Continued)

OTHER PUBLICATIONS

English Abstract of CN 105997165A, NuVasive, Inc., Oct. 12, 2016, 2 pp.
(Continued)

*Primary Examiner* — David W Bates
(74) *Attorney, Agent, or Firm* — James A. Sheridan; Sheridan Law, LLC

(57) ABSTRACT

A lateral retractor system for forming a pathway to a patient's intervertebral disc space includes a single dilator and a retractable dual-tapered-blade assembly. The dilator may feature a narrow rectangular body for insertion at an insertion orientation parallel to the fibers of the patient's psoas muscle, at an approximate 45-degree angle to the patient's spine. The retractable dual-tapered-blade assembly consists of only two blade subassemblies, each having a blade bordered by adjustable wings, along with built-in lighting and video capabilities. The dual-tapered-blade assembly may be passed over the single dilator at the insertion orientation and rotated approximately 45-50 degrees to a final rotated orientation parallel to the intervertebral disc space before the two blade subassemblies are retracted away from one another to create the surgical pathway, while simultaneously and continuously assessing for encroachment upon one or more nerve structures within 360-degrees of the instrument. Other embodiments are also disclosed.

20 Claims, 42 Drawing Sheets

Related U.S. Application Data application No. 16/356,494, filed on Mar. 18, 2019, now Pat. No. 10,426,452, which is a division of application No. 16/273,322, filed on Feb. 12, 2019, now Pat. No. 10,363,023.

(51) Int. Cl.

| | | |
|---|---|---|
| *A61N 1/00* | (2006.01) | |
| *A61B 90/00* | (2016.01) | |
| *A61F 2/46* | (2006.01) | |
| *A61B 90/30* | (2016.01) | |
| *A61B 17/00* | (2006.01) | |

(52) U.S. Cl.
CPC ............ *A61M 29/00* (2013.01); *A61N 1/00* (2013.01); *A61B 90/361* (2016.02); *A61B 2017/00022* (2013.01); *A61B 2017/0256* (2013.01); *A61B 2090/309* (2016.02); *A61F 2/4611* (2013.01)

(56) References Cited

U.S. PATENT DOCUMENTS

| | | | |
|---|---|---|---|
| 7,300,450 | B2 | 11/2007 | Vleugels |
| 7,435,219 | B2 | 10/2008 | Kim |
| 7,582,058 | B1 | 9/2009 | Miles et al. |
| 7,946,982 | B2 | 5/2011 | Hamada |
| 8,456,739 | B2 | 6/2013 | Stuettler |
| 8,550,994 | B2 | 10/2013 | Miles |
| 8,816,599 | B2 | 8/2014 | Wood |
| 9,002,159 | B2 | 4/2015 | Sutherland |
| 9,125,587 | B2 | 9/2015 | Hawkins |
| 9,351,845 | B1 | 5/2016 | Pimenta |
| 9,486,133 | B2 | 11/2016 | Lee et al. |
| 9,579,131 | B1* | 2/2017 | Gustine ............ A61B 17/705 |
| 9,615,728 | B2 | 4/2017 | Charles |
| 9,655,505 | B1 | 5/2017 | Gharib et al. |
| 9,675,334 | B2 | 6/2017 | Heiges et al. |
| 9,717,403 | B2 | 8/2017 | Kleiner |
| 9,730,683 | B2 | 8/2017 | Reimels |
| 9,795,367 | B1* | 10/2017 | Lee ............ A61B 17/0206 |
| 9,839,349 | B2 | 12/2017 | Dejima |
| 9,888,859 | B1 | 2/2018 | Spangler |
| 10,039,540 | B2 | 8/2018 | Heiman |
| 10,194,896 | B2 | 2/2019 | Donald |
| 10,363,023 | B1 | 7/2019 | Rustamzadeh |
| 10,413,287 | B2 | 9/2019 | Heiges et al. |
| 2005/0137461 | A1 | 6/2005 | Marchek |
| 2005/0149035 | A1* | 7/2005 | Pimenta ............ A61B 1/32 606/86 R |
| 2007/0100212 | A1* | 5/2007 | Pimenta ............ A61B 5/0488 600/210 |
| 2008/0097164 | A1 | 4/2008 | Miles |
| 2008/0221586 | A1 | 9/2008 | Garcia-Bengochea |
| 2009/0259108 | A1* | 10/2009 | Miles ............ A61B 5/0492 600/202 |
| 2010/0076502 | A1 | 3/2010 | Guyer |
| 2010/0174147 | A1* | 7/2010 | Miles ............ A61B 5/4893 600/202 |
| 2010/0030540 | A1 | 12/2010 | Chang |
| 2010/0331883 | A1 | 12/2010 | Schmitz |
| 2011/0088707 | A1 | 4/2011 | Hardenbrook |
| 2011/0208226 | A1* | 8/2011 | Fatone ............ A61B 5/0492 606/191 |
| 2011/0257478 | A1 | 10/2011 | Kleiner |
| 2012/0022575 | A1 | 1/2012 | Mire |
| 2012/0029518 | A1 | 2/2012 | Blackwell |
| 2012/0271120 | A1 | 10/2012 | Seex |
| 2013/0150676 | A1* | 6/2013 | Miles ............ A61B 1/32 600/202 |
| 2013/0338466 | A1 | 12/2013 | Stone |
| 2014/0005484 | A1 | 1/2014 | Charles |
| 2014/0005486 | A1 | 1/2014 | Charles |
| 2014/0039264 | A1* | 2/2014 | Heiman ............ A61B 5/04001 600/202 |
| 2014/0179998 | A1 | 6/2014 | Pacey |
| 2014/0296982 | A1 | 10/2014 | Cheng |
| 2015/0045626 | A1 | 2/2015 | Reimels |
| 2015/0051448 | A1 | 2/2015 | Hunt et al. |
| 2015/0265265 | A1 | 9/2015 | Hynes et al. |
| 2015/0265320 | A1 | 9/2015 | Hynes |
| 2016/0192922 | A1 | 7/2016 | Friedrich et al. |
| 2016/0270772 | A1 | 9/2016 | Beale |
| 2016/0287236 | A1 | 10/2016 | Garcia-Bengochea |
| 2017/0014118 | A1 | 1/2017 | Capote |
| 2017/0042003 | A1 | 2/2017 | Logvinov |
| 2017/0094236 | A1 | 3/2017 | Kiriyama |
| 2017/0105176 | A1 | 4/2017 | Finnegan |
| 2017/0189125 | A1 | 7/2017 | Malackowski |
| 2017/0231614 | A1 | 8/2017 | Vogel et al. |
| 2017/0258315 | A1* | 9/2017 | Gharib ............ A61B 1/32 |
| 2017/0367772 | A1 | 12/2017 | Gunn |
| 2018/0014722 | A1* | 1/2018 | Lee ............ A61B 90/30 |
| 2018/0124892 | A1 | 5/2018 | Hollopeter |
| 2018/0199927 | A1 | 7/2018 | Mast et al. |
| 2018/0206834 | A1 | 7/2018 | Villamil et al. |
| 2018/0333152 | A1 | 11/2018 | Heiman |
| 2019/0015089 | A1 | 1/2019 | Rosenbaum |
| 2019/0021874 | A1* | 1/2019 | Pimenta ............ A61B 17/8685 |
| 2019/0206562 | A1 | 7/2019 | Shelton, IV |
| 2019/0254650 | A1* | 8/2019 | Martinelli ............ A61B 5/0488 |
| 2019/0261498 | A1 | 8/2019 | Akita |

FOREIGN PATENT DOCUMENTS

| | | |
|---|---|---|
| CN | 105997165 A | 10/2016 |
| EP | 2 744 421 B1 | 12/2016 |
| WO | 2013/028571 A1 | 2/2013 |
| WO | 2015/023651 A1 | 2/2015 |
| WO | 2016/040497 A1 | 3/2016 |
| WO | 2017/011432 A1 | 1/2017 |
| WO | 2017/155718 A1 | 9/2017 |

OTHER PUBLICATIONS

International Search Report and Written Opinion from Int. Appl. No. PCT/US2019/054162, dated Nov. 29, 2019, 9 pp.

* cited by examiner

LATERAL RETRACTION SYSTEM FOR MINIMIZING MUSCLE DAMAGE IN SPINAL SURGERY

REFERENCE TO PENDING PRIOR PATENT APPLICATIONS

The application is a continuation-in-part of pending prior U.S. patent application Ser. No. 16/533,368, filed Aug. 6, 2019 by Edward Rustamzadeh for "LATERAL RETRACTOR SYSTEM FOR MINIMIZING MUSCLE DAMAGE IN SPINAL SURGERY," which is a continuation of prior U.S. patent application Ser. No. 16/356,494, filed Mar. 18, 2019 by Edward Rustamzadeh for "LATERAL RETRACTOR SYSTEM FOR MINIMIZING MUSCLE DAMAGE IN SPINAL SURGERY" and issued as U.S. Pat. No. 10,426,452 on Oct. 1, 2019, which is a divisional of prior U.S. patent application Ser. No. 16/273,322, filed Feb. 12, 2019 by Edward Rustamzadeh for "LATERAL RETRACTOR SYSTEM FOR MINIMIZING MUSCLE DAMAGE IN SPINAL SURGERY" and issued as U.S. Pat. No. 10,363,023 on Jul. 30, 2019, all of which patent applications are incorporated herein by reference.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies, or spinal discs. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal discs act as shock absorbers, cushioning the spine, and preventing individual bones from contacting each other. Discs also help to hold the vertebrae together. The weight of the upper body is transferred through the spine to the hips and the legs. The spine is held upright through the work of the back muscles, which are attached to the vertebrae.

A number of approaches, systems, and apparatuses have been devised to accomplish a variety of surgical interventions in association with the spine. These approaches enable a surgeon to place instrumentation and implantable apparatuses related to discectomy, laminectomy, spinal fusion, vertebral body replacement and other procedures intended to address pathologies of the spine. The variety of surgical approaches to the spine have a number of advantages and drawbacks such that no one perfect approach exists. A surgeon often chooses one surgical approach to the spine from a multitude of options dependent on the relevant anatomy, pathology, and a comparison of the advantages and drawbacks of the variety of approaches relevant to a particular patient.

A common surgical approach to the spine is the lateral approach, which, in general, requires a surgeon to access the spine by creating a surgical pathway through the side of the patient's body through the psoas muscle to an intervertebral disc space where it is possible to dock onto the lateral lumbar disc. Variants of the lateral approach are commonly referred to as the "direct lateral" approach in association with the "DLIF" procedure, the "extreme lateral" approach in association with the "XLIF" procedure, and the "oblique lumbar" approach in association with the "OLIF" procedure.

A common problem associated with the lateral surgical approach includes a significant risk of damage to the musculature surrounding the spine. FIGS. 1A-1B illustrates a partial view of a spine 100 comprised of sequential vertebrae 109, each separated by intervertebral disc space 110, with an attached psoas muscle group 102 (including the psoas minor and psoas major). As shown, the psoas muscle 102 runs generally in a cranial-caudal direction with muscle fibers attached diagonally or at an approximate 45-degree angle to the spine 100. FIGS. 2A-2B illustrate an exemplary lateral approach to the spine. In typical lateral approaches, after making an incision in the psoas muscle 102, the surgeon places a number of sequential circular dilators $104_{1-n}$, each larger in diameter, on the desired pathway to the spine 100 through the psoas muscle 102 to dilate the surgical site radially away from the initial incision site or K-wire insertion point. This dilation process can lead to compression of muscle, nerves, and blood supplies adjacent to the vertebral body, which can lead to ipsilateral upper thigh pain, hip flexor weakness that causes difficulty in walking and/or stair climbing, and muscle atrophy that follows from muscle injury.

After the series of circular dilators are forced into the muscle tissue, a multi-bladed or tubular retractor apparatus 106 may be placed over the final dilator $104_n$. The retractor is then retracted radially to separate the psoas muscle and other soft tissues. A common problem associated with this type of lateral procedure is that soft tissues, including the musculature and nerves surrounding the spine, become crushed and/or trapped near the distal end of the retractor's blades when the retractor is passed over the final dilator, a problem often referred to as "trappage," graphically depicted in FIG. 3.

In order for the surgeon to clear the surgical pathway to the disc space, or to "see" the disc space, the surgeon must cauterize and cut the muscle that is caught inside the retractor, effectively performing a muscle biopsy each time the surgeon performs an XLIF, DLIF, OLIF procedure. Beyond undesired muscular damage to the patient, this approach requires additional effort for the surgeon to utilize a cautery or similar device to remove the trapped soft tissues from between the distal end of the retractor and the vertebral bodies prior to completing access to the spine.

Oftentimes the resulting damage and trauma to the soft tissue resulting from trappage and removal of psoas muscle tissue with a cautery causes lasting problems for a patient. For instance, a patient who experiences trappage during surgery will often have ipsilateral upper thigh pain and leg weakness. Such pain and leg weakness occurs due to the linkage of the psoas to the lower body, as the psoas muscle connects to the femur. Thus, damage to the psoas will generally manifest in lower body discomfort, including pain and weakness in the leg.

Another problem associated with existing lateral surgical approaches to the spine is nerve damage. The lumbar plexus is a web of nerves (a nervous plexus) in the lumbar region of the body which forms part of the larger lumbosacral plexus. The lumbar plexus in particular is often damaged as a direct result of surgical intervention utilizing the lateral approach to the spine. The nerves associated with the lumbar plexus can experience indirect nerve injury as a result of over-dilation or over-retraction of apparatuses utilized to accomplish lateral access to the spine. They also can experience direct nerve injury as a result of direct trauma caused by impingement from the instrumentation utilized during the surgical intervention in association with the lateral approach to the spine, as in the case of trappage, discussed above. Such indirect and direct nerve damage can cause numbness in part or all of the leg and can lead to indirect muscle atrophy. A recent meta-analysis review of 24 published articles indicates that the lateral approach is associated with up to a 60.7% complication rate. Gemmel, Isaac D, et. al, Systemic Review of Thigh Symptoms after Lateral Transpsoas Interbody Fusion for Adult Patients with Degenerative Lumbar Spine Disease, International Journal of Spine Surgery 9:62 (2015). The review further found that the retractors resulted in 43% psoas muscle pain, 30.8% psoas muscle weakness, and 23.9% nerve or plexus injury due to the inherently flawed design of existing commercially available retractors.

One existing method of neuromonitoring involves the insertion of a number of epidural electrodes into the lumbar plexus. Stimulation of the electrodes is used to trigger a response in the patient's nerve structures, and the resulting evoked potentials correspond to the neural activities of the nerve structures near the recording electrodes. The potentials may be recorded to detect reactions in the nervous system that may indicate a problem, including some type of impingement or encroachment of an instrument upon the nerve structures during a procedure. This method, while providing information relating to a change in the behavior of the nerve structures nearby the inserted electrodes, does not directly correlate to a change in the behavior of the nerve structures in response to a nearby surgical instrument such as a dilator or a retractor, and is therefore not optimal for identifying impingement from the instrumentation utilized during the surgical intervention.

In addition, existing dilators oftentimes incorporate a vertical wire conductor that extends through the outer wall of the dilator parallel to the longitudinal axis of the apparatus, terminating in a pinpoint electrode at the distal end of the apparatus. The electrode may stimulate nearby nerve structures to asses for any impingement upon nerve or plexus. Because the vertical wire provides only a pinpoint electrode, the surgeon must manually rotate the apparatus through 360 degrees to perform a full range of neuromonitoring for impingement upon all of the adjacent neurological structures surrounding the device: the front and the back, superior and inferior. This additional step is cumbersome and presents challenges in achieving thorough neuromonitoring. Moreover, because existing dilators with pinpoint electrodes require the surgeon to rotate the dilators to achieve neuromonitoring in 360 degrees, the dilators cannot perform a full range of monitoring once they are affixed. After fixation, only pinpoint monitoring is provided, and existing devices cannot provide continuous, real-time neuromonitoring throughout the procedure.

Existing retractor systems also present challenges in terms of illumination and require a separate light source that attaches to the top of the retractor. This separate device is cumbersome, physically interfering and disruptive, and the limited ability to position the light source oftentimes means that light reflects off of the retractor blades before returning to the surgeons eyes, which leads to suboptimal visualization of the surgical area.

Existing retractor systems also lack ease of adjustability and are not designed with an eye toward ergonomic use by the surgeon, who is forced to hunch over the retractor apparatus during the course of the procedure to direct the surgical equipment as desired.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a lateral retractor system for forming a surgical pathway to a patient's intervertebral disc space. The lateral retractor system may include: (1) a dilator having a narrow body defined by opposing flat surfaces that extend between a proximal end and a distal end, the distal end tapering to a distal edge configured for insertion at an insertion orientation in which the opposing flat surfaces are parallel to a plurality of psoas muscle fibers and angled relative to the disc space; and (2) a retractable dual-blade assembly consisting of two opposing blade subassemblies, each of the blade subassemblies comprising: (a) a blade having a planar inner surface, an outer surface, a proximal blade portion, a distal blade portion, and opposing longitudinal edges extending from a proximal end of the proximal blade portion to a distal end of the distal blade portion; and (b) an adjustable wing hingedly coupled with each of the opposing longitudinal edges of the blade, the adjustable wing configured to move between an open position parallel to the planar inner surface of the blade and a closed position perpendicular to the planar inner surface of the blade, the retractable dual-blade assembly configured to pass over the dilator at the insertion orientation such that the planar inner surfaces of the blades contact the opposing flat surfaces of the dilator.

Another embodiment provides a lateral retraction system for minimizing damage to a patient's muscle fibers and nerve structures when forming a surgical pathway to the patient's spine. The lateral retraction system may include: (1) a dilator having a narrow body defined by opposing flat surfaces that taper to a distal edge configured for insertion adjacent to an intervertebral disc space at an insertion orientation in which the opposing flat surfaces of the dilator are parallel to a plurality of psoas muscle fibers and at an approximate 45 degree angle to the patient's spine; and (2) a lateral retractor, including (a) a dual-blade assembly consisting of a pair of blade subassemblies, each having a blade with a planar inner surface and an outer surface, the dual-blade assembly configured to pass proximally-to-distally over the dilator at the insertion orientation such that the planar inner surface of the blade of each of the blade subassemblies contacts one of the opposing flat surfaces of the dilator; (b) a rotation assembly operably coupled between the dual-blade assembly and a surgical table, the rotation assembly configured to rotate the dual-blade assembly about a longitudinal center axis of the dilator from the insertion orientation to a rotated orientation in which the planar inner surface of each of the blades is parallel to the intervertebral disc space; and (c) a lateral retraction assembly operably coupled between the dual-blade assembly and the surgical table, the lateral retraction assembly configured to separate the pair of the blade subassemblies from one another.

Yet another embodiment provides a dilation system for use with a lateral retraction assembly for forming a surgical pathway to a patient's intervertebral disc space. The dilation system may consist of a single dilator having a narrow body defined by opposing first and second flat surfaces that extend proximally-to-distally from a proximal end to a distal end, wherein the distal end of the body tapers to a distal edge along a first tapered surface and an opposing second tapered surface, the distal edge of the dilator configured for insertion at an insertion orientation in which the first and the second flat surfaces are disposed at approximately a 45-degree angle to the patient's disc space and parallel with a plurality of psoas muscle fibers of the patient.

Another embodiment provides a method of forming a surgical pathway through a side of a patient's body and through a psoas muscle to an intervertebral disc space. The method may include the following steps: (1) providing a dilator having a narrow body defined by opposing flat surfaces that extend from a proximal end to a distal end, the distal end tapering to a distal edge; (2) positioning the dilator at an insertion orientation in which the opposing flat surfaces of the dilator are disposed parallel to the psoas muscle; (3) using the distal edge of the dilator, traversing a plurality of fibers of the psoas muscle until the dilator spans the intervertebral disc space at the insertion orientation in which the opposing flat surfaces of the dilator are disposed parallel to the plurality of the fibers of the psoas muscle and at an angle of approximately 45 degrees to the intervertebral disc space; and (4) via a k-wire extending longitudinally through a center of the dilator, securing the dilator within the intervertebral disc space at the insertion orientation.

A further embodiment provides a method of creating a surgical pathway to a patient's spine using a lateral retractor system including a single planar dilator having a flat cross-section that tapers to a distal edge, a retractable blade assembly including two opposing blades that each taper to a distal edge, a rotation assembly operably coupled with the retractable blade assembly, and a retraction assembly operably coupled with the retractable blade assembly. The method may include the following steps: (1) inserting the single planar dilator through a psoas muscle of the patient such that the distal edge of the single planar dilator spans an intervertebral disc space at an insertion orientation that is parallel to a plurality of fibers of the psoas muscle; (2) using a k-wire extending longitudinally through a center of the single planar dilator, anchoring the single planar dilator at the intervertebral disc space; (3) rotating the single planar dilator about the k-wire from the insertion orientation that is parallel to the psoas muscle to a rotated orientation that is parallel to the intervertebral disc space; and (4) during the steps of inserting, anchoring, and rotating the single planar dilator, and using a first active neuromonitoring tip positioned adjacent to the distal edge of the single planar dilator, monitoring for an encroachment upon one or more nerve structures of the patient located adjacent to any portion of a circumference of the first active neuromonitoring tip.

Yet another embodiment provides a method of forming a surgical pathway to a patient's spine. The method may include the following steps: (1) providing a dilator having a body with a flat cross-section defined by two opposing flat surfaces that taper to a distal edge via two opposing tapered surfaces; (2) positioning the dilator over an intervertebral disc space of the patient at an insertion orientation in which the two opposing flat surfaces are parallel to one or more fibers of a psoas muscle of the patient; (3) passing a k-wire longitudinally through a center of the dilator; (4) securing the k-wire at the intervertebral disc space; (5) passing a dual-blade assembly proximally-to-distally over the dilator, the dual-blade assembly having (a) two opposing blades, each having a planar inner surface and an outer surface that extend from a proximal end of a reusable proximal portion to a distal end of a disposable distal portion along two longitudinal edges; and (b) an adjustable wing hingedly coupled with each of the two longitudinal edges of each of the two opposing blades; (6) operably coupling a rotation assembly to the dual-blade assembly; (7) using the rotation assembly, rotating the dual-blade assembly and the dilator about the k-wire from the insertion orientation to a rotated orientation in which the two opposing flat surfaces of the dilator are parallel to the intervertebral disc space; (8) operably coupling a lateral retraction assembly to the dual-blade assembly; and (9) using the lateral retraction assembly, separating the two opposing blades of the dual-blade assembly from one another.

A further embodiment provides a retractable blade assembly for use in forming a surgical pathway to an intervertebral disc space of a patient's spine. The retractable blade assembly consists of: (1) a first blade subassembly detachably attached to a second opposing blade subassembly, each of the first and the second blade subassemblies comprising (a) a blade defined by a planar inner surface, an outer surface, and two longitudinal edges, the blade including a proximal blade portion extending from a proximal end to a distal end that is attached to a distal blade portion extending from a proximal end to a distal edge.

Still another embodiment provides a dual-blade assembly for placement about a narrow planar dilator in forming a surgical pathway to a patient's spine, the dual-blade assembly comprising not more than two retractable blades, the retractable blades opposing one another and configured to separate from one another, each of the retractable blades comprising an opposing inner surface having a planar geometry.

An additional embodiment provides a dual-blade assembly for forming a surgical pathway to a patient's spine. The dual-blade assembly may include: (1) a first blade subassembly having (a) a first blade defined by a first outer surface, a first planar inner surface, and two first longitudinal sides; and (b) a first opposing adjustable wing hingedly coupled with each of the first longitudinal sides; (2) a second blade subassembly having (a) a second blade defined by a second outer surface, a second planar inner surface, and two second longitudinal sides; and (b) a second opposing adjustable wing hingedly coupled with each of the second longitudinal sides; and (3) a coupling device configured to detachably attach the first and the second blade subassemblies such that the first and the second planar inner surfaces oppose one another, wherein the dual-blade assembly is configured to provide three modalities of motion including: (i) when the coupling device is an attached configuration, rotation of the dual-blade assembly about a center longitudinal co-axis of the first and the second blades; (ii) when the coupling device is in a detached configuration, retraction of the first and the second blade subassemblies from one another; and (iii) when the coupling device is in the detached configuration, rotation of the first and the second opposing adjustable wings relative to the first and the second planar inner surfaces of the first and the second blades, respectively.

Still another embodiment provides a lateral retractor system for forming a surgical pathway through a plurality of psoas muscle fibers to a patient's intervertebral disc space, comprising a dilator including: (1) a conductive body defined by opposing flat surfaces that extend between a proximal end and a distal end; (2) a first nonconductive layer disposed upon an outer surface of the conductive body; (3) a first active neuromonitoring tip protruding from the distal end of the conductive body to a leading distal edge configured for insertion into the intervertebral disc space; and (4) a first conductive electrical pathway extending from a first conductive input surface at the proximal end of the conductive body, through the conductive body, and to the first active neuromonitoring tip such that an electrical signal applied to the first conductive input surface causes the first active neuromonitoring tip to simultaneously and continuously stimulate one or more nerve structures located adjacent to any portion of a circumference of the distal end of the conductive body to assess for an encroachment of the dilator upon the one or more of the nerve structures.

Yet another embodiment provides a dilation system for minimizing damage to a patient's psoas muscle fibers when forming a surgical pathway to an intervertebral disc space of the patient's spine. The dilation system may include a dilator having: (1) a conductive body portion comprising two opposing flat surfaces that extend between a proximal end and distal end; (2) an insulative coating overlaying the conductive body portion; and (3) a conductive neuromonitoring portion extending distally from the distal end of the conductive body portion to a leading distal edge configured for insertion between the patient's psoas muscle fibers, wherein when an electrical dilator stimulus is applied to the proximal end of the conductive body portion, the electrical dilator stimulus propagates through the conductive body portion to the conductive neuromonitoring portion such that the conductive neuromonitoring portion simultaneously stimulates one or more nerve structures located adjacent to any point about a circumference of the conductive neuromonitoring portion.

Another embodiment provides a retraction system for forming a surgical pathway through a patient's psoas muscle to the patient's intervertebral disc space, comprising: (1) a planar dilator for traversing a plurality of fibers of the patient's psoas muscle, the planar dilator having a dilator body portion with opposing flat surfaces and a dilator neuromonitoring portion extending distally from the dilator body portion; (2) a dual-blade retractor having opposing retractable blades, each of the opposing retractable blades configured to pass over the planer dilator such that each of the opposing retractable blades contacts one of the opposing flat surfaces of the planar dilator, each of the opposing retractable blades having a blade body portion and a blade neuromonitoring portion extending distally from the blade body portion, wherein: (a) the planar dilator and each of the opposing retractable blades are conductive such that an electrical dilator stimulus applied to the dilator body portion propagates to the dilator neuromonitoring portion and an electrical blade stimulus applied to the blade body portion of each of the opposing retractable blades propagates to each of the blade neuromonitoring portions to simultaneously and continuously stimulate one or more nerve structures located adjacent to any portion of a circumference of the dilator neuromonitoring portion and any portion of a circumference of each of the blade neuromonitoring portions to assess for an encroachment of the planar dilator and the dual-blade retractor upon the one or more of the nerve structures.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1A:
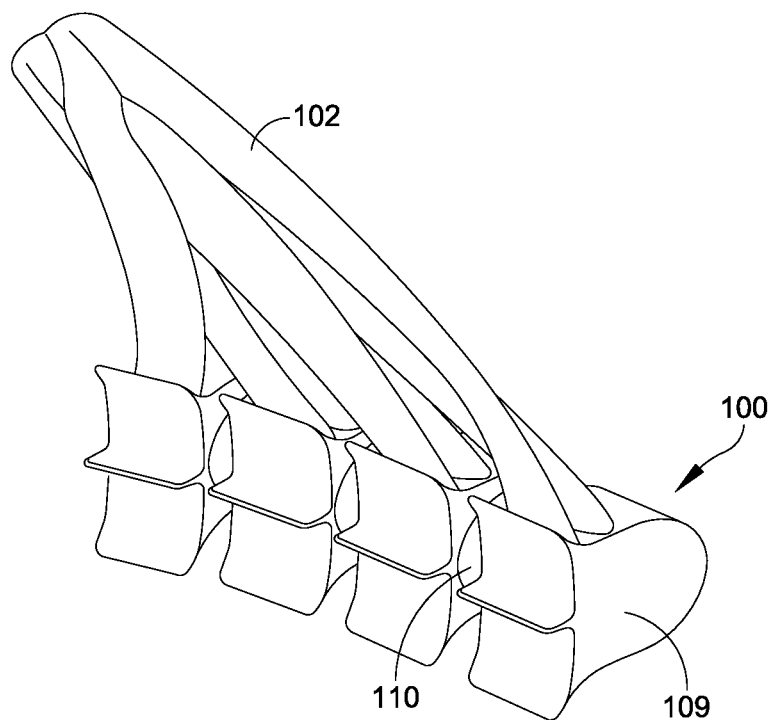
FIGS. 1A-1B illustrate perspective and top partial views, respectively, of a patient's spine comprised of sequential vertebrae, each separated by an intervertebral disc space, with an attached psoas muscle group.
Figure 1B:
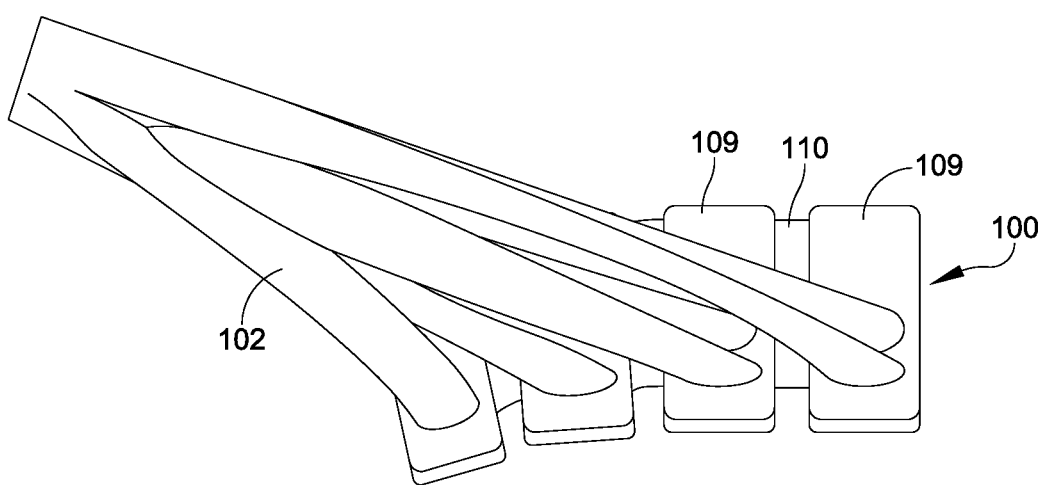
Figure 2A:
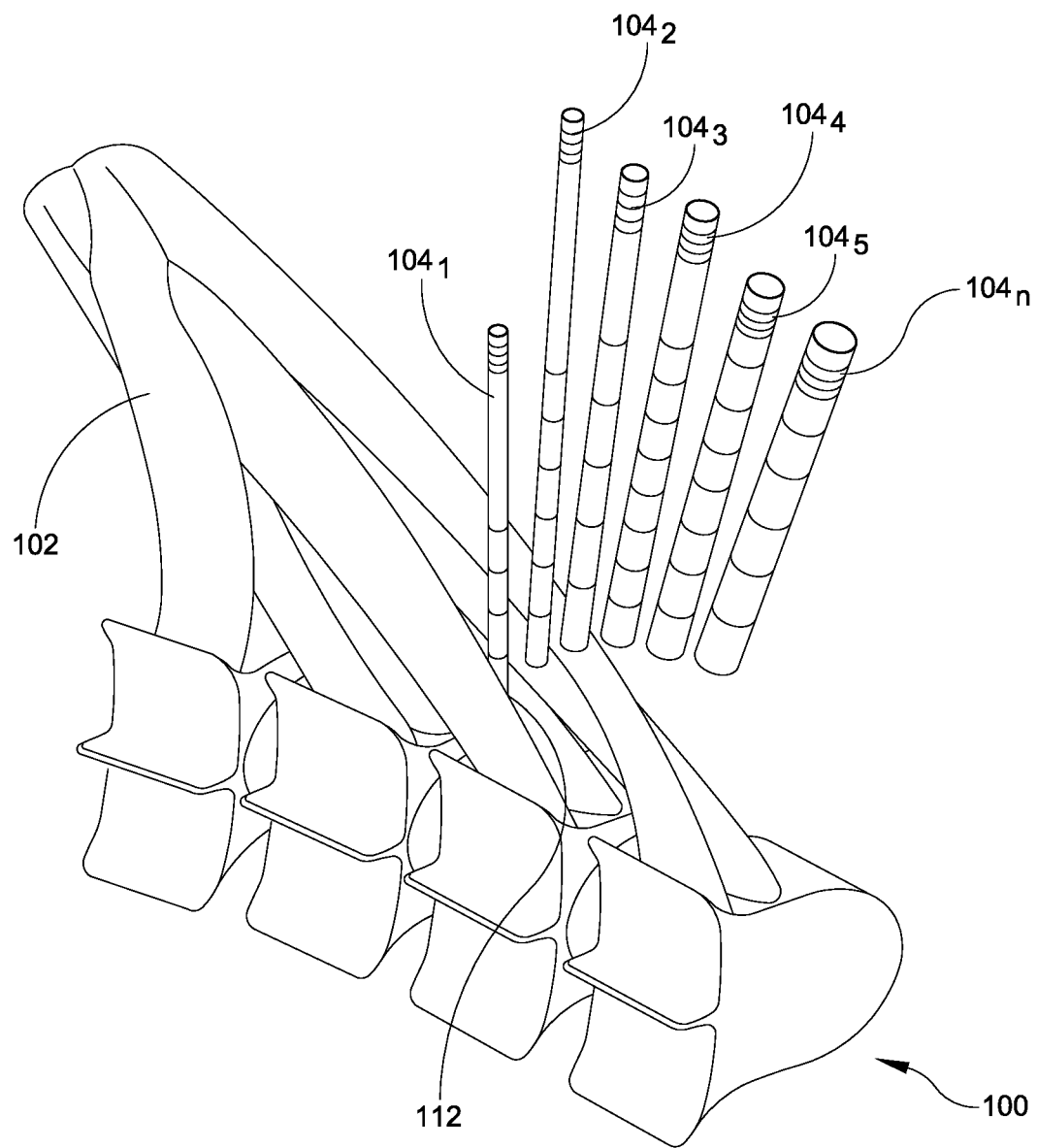
FIGS. 2A-2B illustrate perspective views of a prior art retraction system including a series of increasing-diameter dilators and a circular lateral retractor, as inserted into the spine of FIGS. 1A-1B.
Figure 2B:
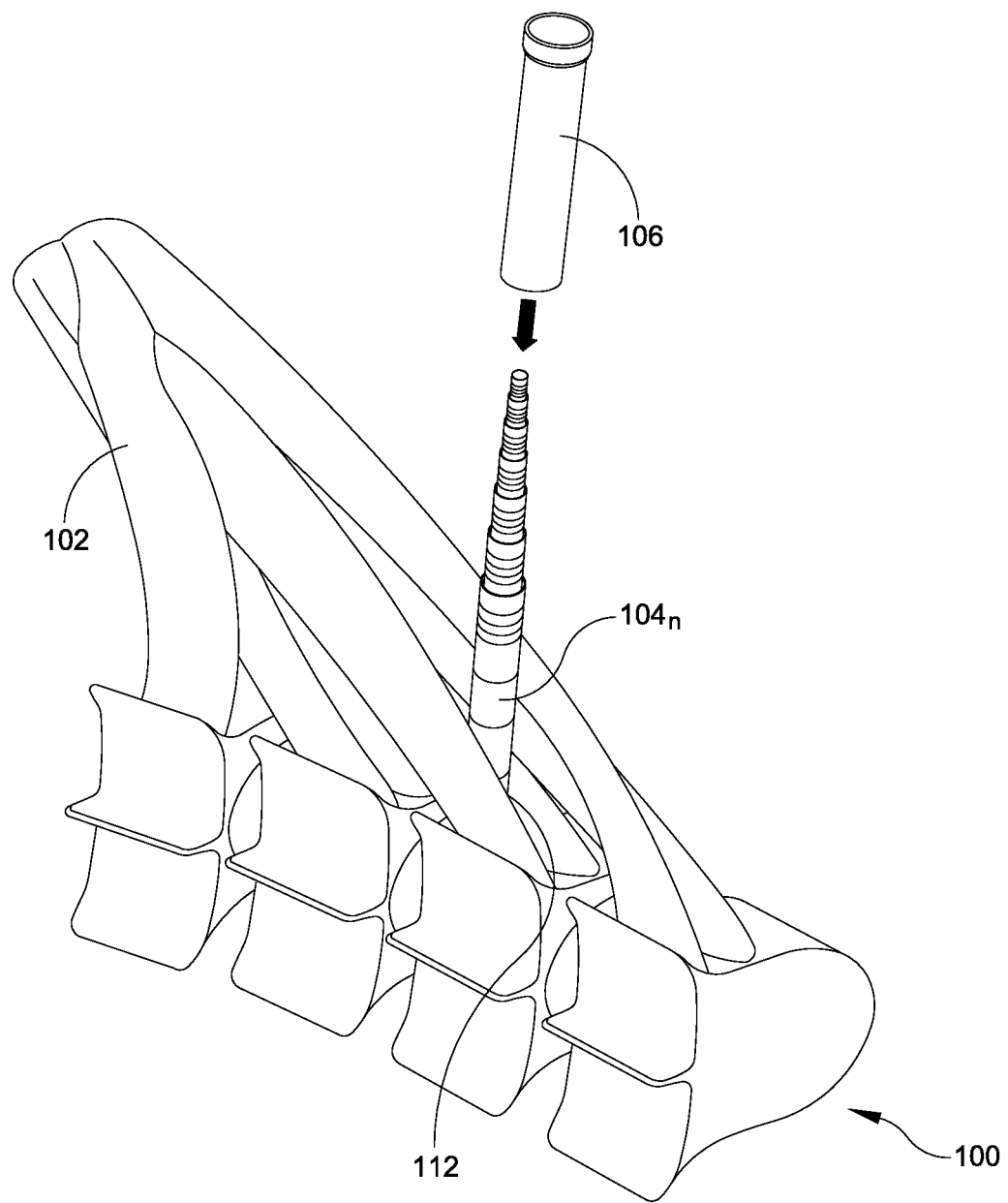
Figure 3:
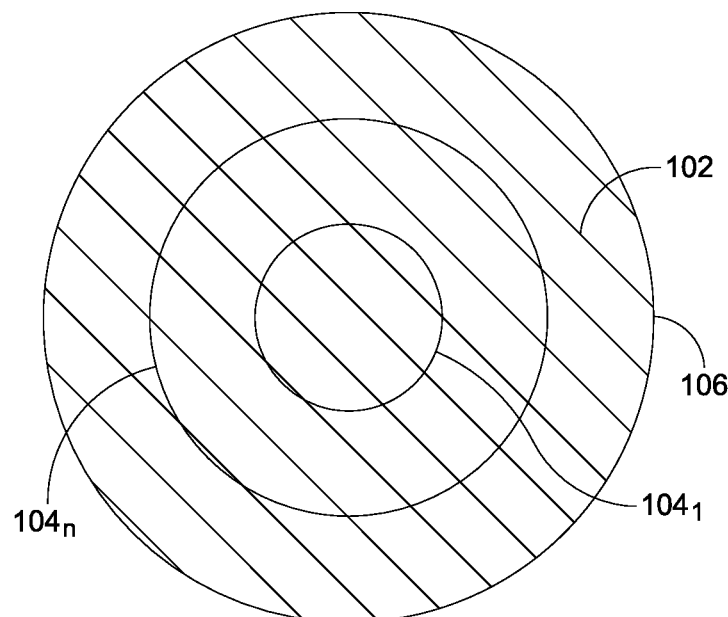
FIG. 3 illustrates a bottom-plan view of the prior art dilators and lateral retractor of FIGS. 2A-2B, as inserted into the psoas muscle and trapping the muscle fibers.
Figure 4:
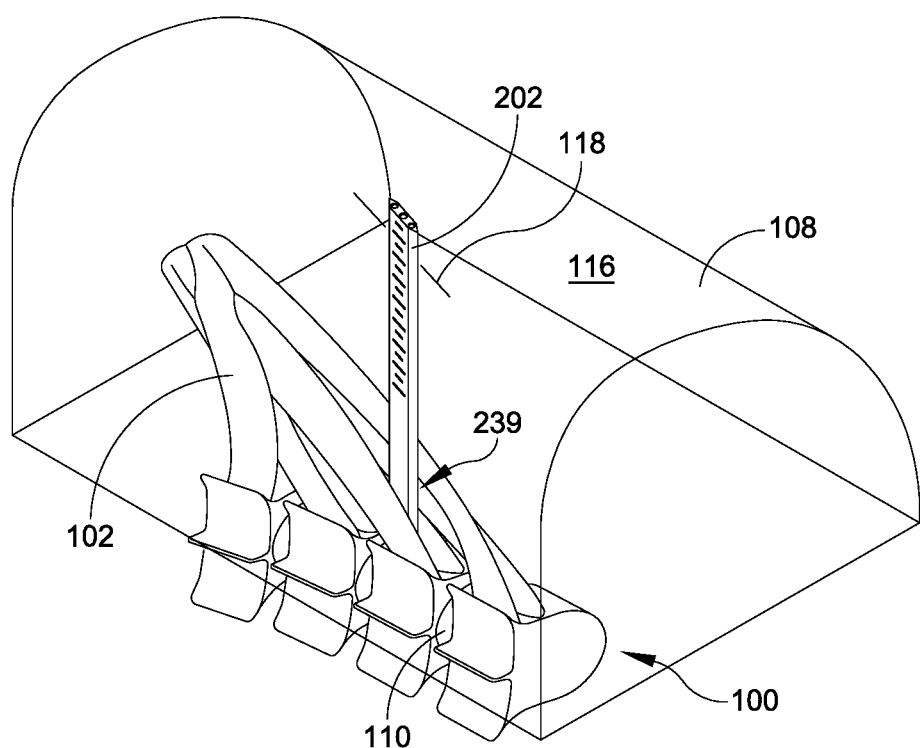
FIGS. 4-6 illustrate respective perspective, top, and front views of one embodiment of a rectangular dilator, as inserted at an insertion orientation through a patient's side body and through the psoas muscle over the intervertebral disc space of FIGS. 1A-1B.
Figure 5:
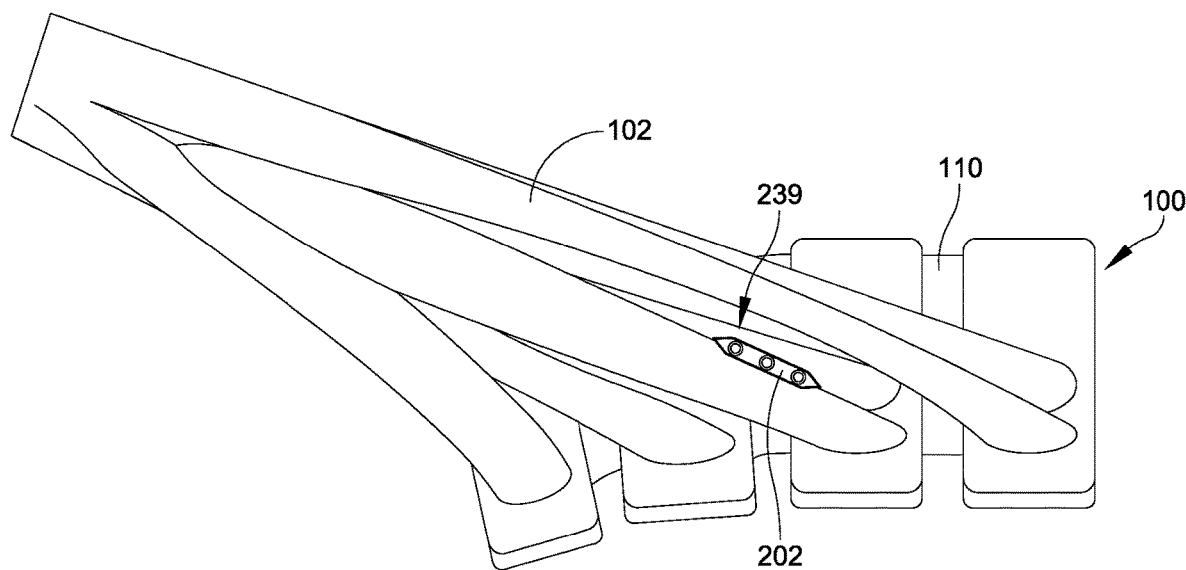

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

This disclosure details a system and method of use for a lateral approach to creating a minimally invasive surgical pathway through a patient's side body and psoas muscle 102 to the intervertebral disc space 110 of the spine 100. Embodiments may include a lateral retractor system having a flat, narrow dilator having a body that tapers to a distal edge. The dilator inserted in a diagonal orientation that is parallel to the angled fibers of the psoas muscle and anchored into the disc space 110 via a K-wire. The dilator may be used in conjunction with a dual-blade lateral retractor that may be placed in a corresponding diagonal orientation over the flat, narrow dilator before the entire system is rotated approximately 45-50 degrees to the horizontal, or until the dilator and the lateral retractor are parallel with the disc space 110, as shown and discussed in FIGS. 17-18 below. Once the system is rotated, the dilator may be removed and the dual blades of the lateral retractor may be laterally separated to push the muscle fibers away and to complete the surgical pathway in a manner that minimizes entrapment of, impingement upon, and/or damage to the patient's muscle fibers and nerve structures. Because the dilator is narrow or flat in shape, which allows the dilator to be placed in its insertion orientation parallel to the muscle fibers and then rotated to its final rotated orientation parallel to the disc space, the system functions with a single element or component dilator, rather than requiring placement of a series of sequentially larger circular dilators, as discussed in the Background section above.

Both the dilator and the lateral retractor may incorporate real-time, 360 degree neuromonitoring through stimulated horizontal wiring positioned on the external sides/surfaces of each of the distal dilator tip and the distal ends of the blades of the lateral retractor, enabling real-time and continuous neuromonitoring throughout the procedure from front to back and superior to inferior. Embodiments of the lateral retractor system may also incorporate built-in LED lighting for superior surgical visualization, as well as micro-video capabilities that enable the system to be operated in the most ergonomic and efficient fashion.

Turning to exemplary embodiments, FIGS. 4-34 and 35A-35B generally illustrate a method of using embodiments of a disclosed lateral retractor system 200 (FIG. 32) to employ a lateral surgical approach to clear a surgical pathway 114 to a patient's spinal disc space 110. Specifically and in one embodiment, FIGS. 4-34 detail a number of steps in which exemplary devices are in use to create the surgical pathway 114 through the side of a patient's body 108, through the psoas muscle 102, and to the intervertebral disc space 110, while FIGS. 35A-35B provide a flowchart depicting an exemplary method 500 of creating the surgical pathway 114 through the side of the patient's body 108 through the psoas muscle 102 to the disc space 110.

Figure 35A:
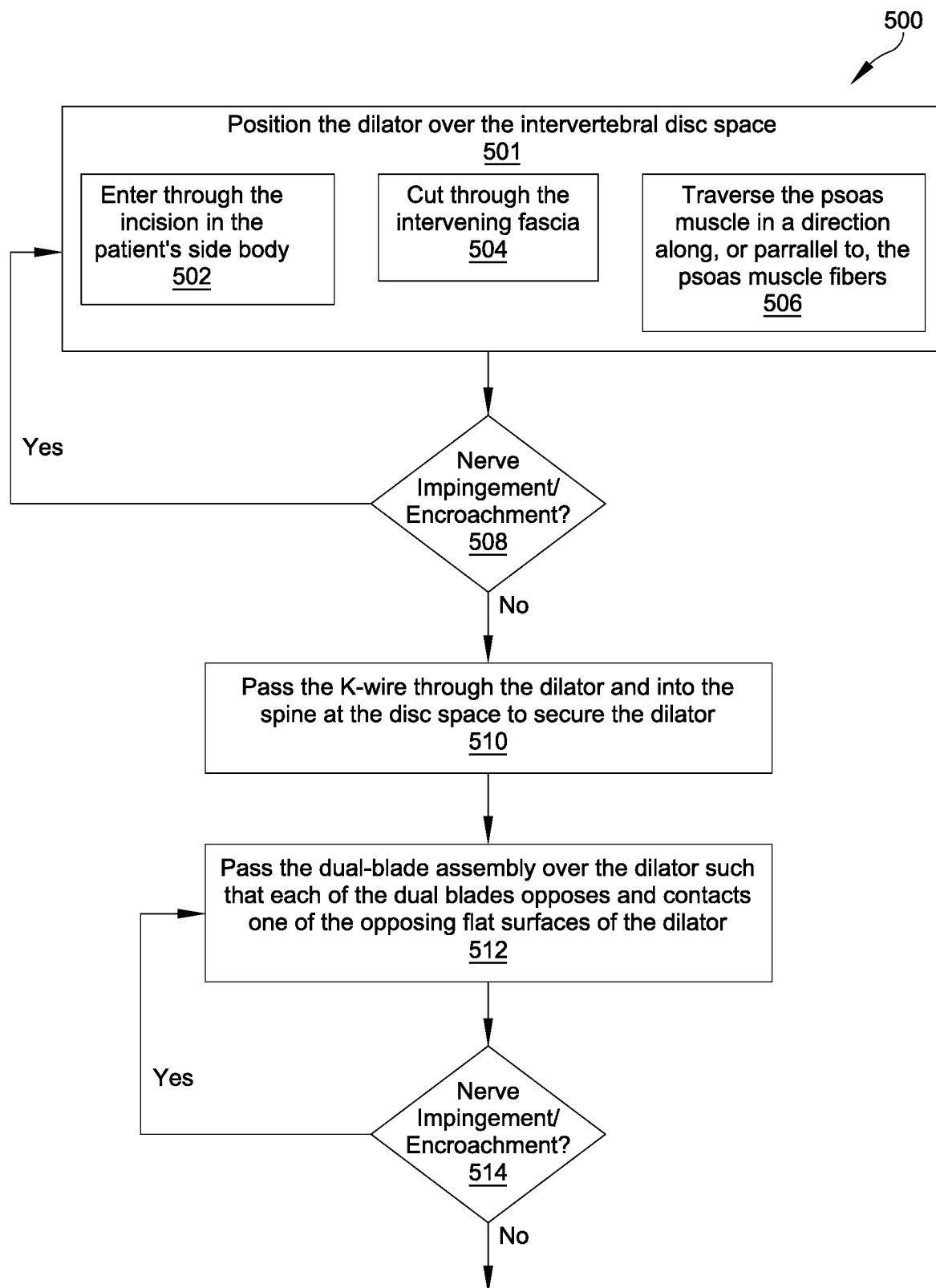
FIGS. 35A-35B provide a flowchart depicting an exemplary method of creating a surgical pathway to the patient's spine using the assemblies and systems of FIGS. 4-34

Employing fluoroscopy imaging technology, a dilator 202 may be placed over/adjacent to the intervertebral disc space 110 (FIG. 35A, 501). Specifically, and referring to FIGS. 4-7, the dilator 202 may enter through an incision 118 in the patient's side body 108 (FIG. 35A, 502), cut through any intervening fascia (FIG. 35A, 504), and then traverse the psoas muscle 102 in a direction, or at an insertion orientation 239, that is "along," or parallel to the muscle fibers of the psoas muscle 102, and diagonal to, or angled at approximately 45 degrees to, the patient's spine 100 (FIG. 35A, 506). The psoas muscle 102 may be accessed via the side of the patient's body 108 such that the dilator 202 protrudes from a lateral surface 116 of the patient's body 108 when inserted to full depth at the spinal column 100.

Figure 6:
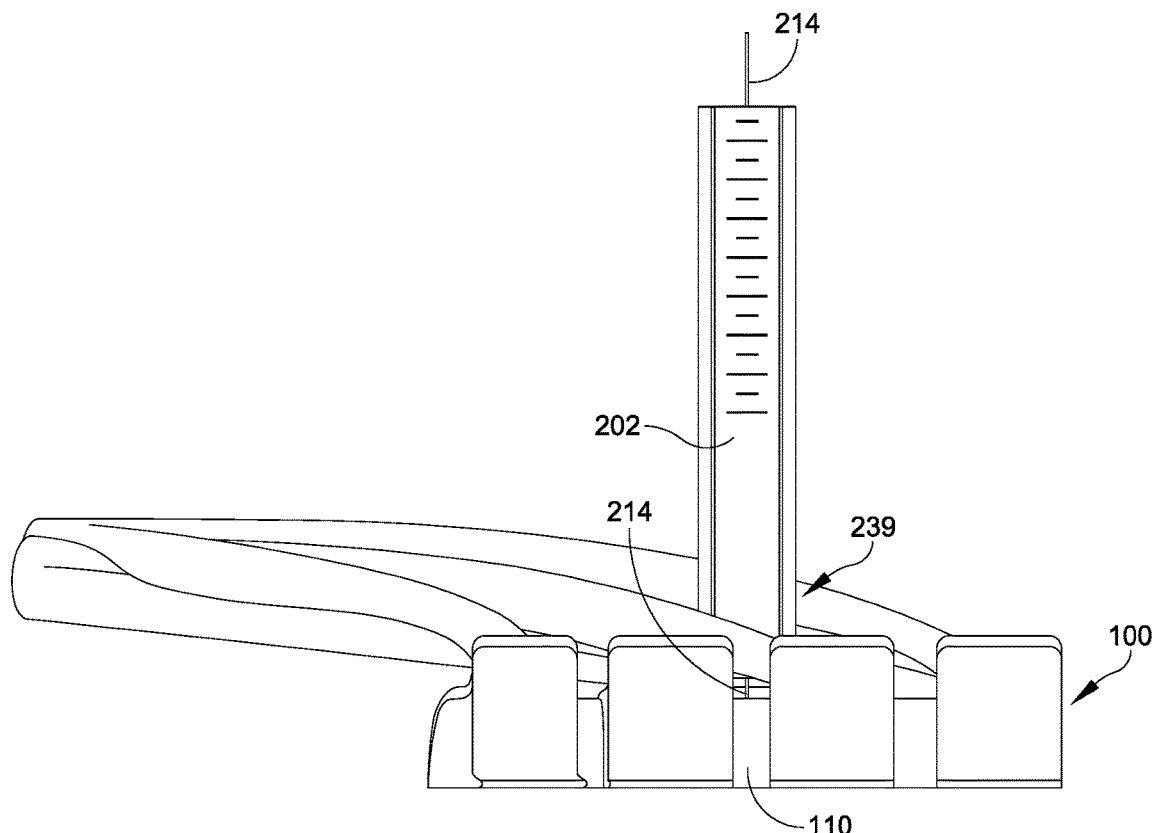
Figure 7:
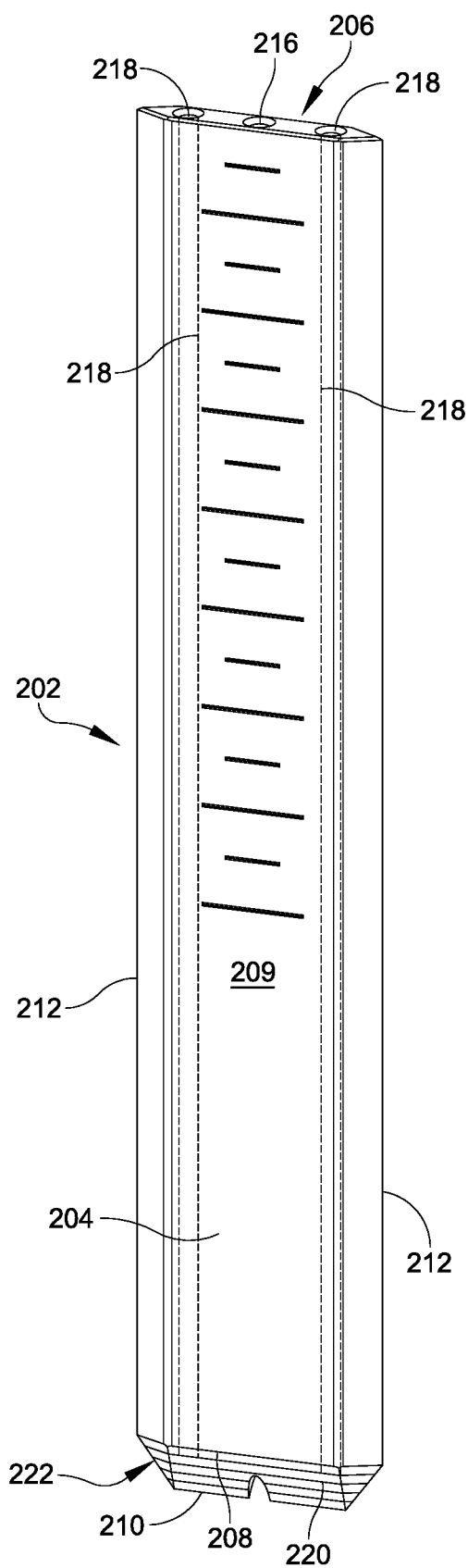
FIG. 7 illustrates a perspective view of the rectangular dilator of FIGS. 4-6.

FIG. 7 illustrates a perspective view of one embodiment of the dilator 202. In this embodiment, the dilator 202 may feature a flat, narrow body 204 having opposing flat surfaces 209 that extend between a proximal end 206 for positioning at the lateral surface 116 of the patient's side body 108 (FIG. 4) and a distal end 208 for positioning adjacent the patient's spine 100. The longitudinal sides of the narrow body 204 of the dilator 202 may taper to opposing longitudinal edges 212, and the distal end 208 of the dilator 202 may taper to a distal edge 210 capable of cutting through the patient's fascia and traversing the fibers of the psoas muscle 102 in the parallel manner described above. As a result, the dilator 202 separates, rather than crushes, the fibers of the psoas muscle 102 as it traverses through the psoas muscle 102 to the spine 100, as shown in FIGS. 4-6 and 8.

The dilator 202 may also include a K-wire access aperture 216 that extends longitudinally through the body 204 of the dilator 202. In addition, conducting wires 218 may extend longitudinally through each side of the body 204 of the dilator 202. At the distal end 208 of the dilator 202, the conducting wires 218 may be in electronic communication with a set of horizontal neurosensing wires 220 that are integrated or built into each side of the tapered distal end 208 of the dilator 202. At the proximal end 206 of the dilator, the conducting wires 218 may be in electronic communication with a monitoring cable 224, shown in FIG. 8, which may be configured to conduct an electronic stimulus through the conducting wires 218 to the horizontal neurosensing wires 220, forming an active neuromonitoring tip 222 about an entirety of the distal end 208 of the dilator 202.

Impingement of the active monitoring tip 222 upon, or alternatively, encroachment of the active monitoring tip 222 in close proximity to nerve structures located along the patient's spine 100 may stimulate those nerve structures that are nearby or adjacent to the active monitoring tip 222. The voltage of the applied electronic stimulus may be adjusted as necessary and/or required to stimulate nerve structures within a defined distance of the active monitoring tip 222. This applied stimulus causes the nerve structure(s) to fire and generate a responsive signal, which may in turn be conducted from the active monitoring tip 222, through the conducting wires 218, and to the monitoring cable(s) 224 in electronic communication with one or both of the conducting wires 218 at the proximal end 206 of the dilator 202, as shown in FIG. 8, thereby translating the neurosensing stimulation of the active monitoring tip 222 by the nearby nerve structure(s) to external monitoring equipment (not shown) via the monitoring cable 224 and determining, in real time and with 360 degrees of monitoring range or field of view about the distal end 208 of the dilator 202, a possibility of nerve or plexus injury as the dilator 202 is inserted (FIG. 35A, 508).

Embodiments of the dilator 202 and its components may be formed of any appropriate conductive or nonconductive, autoclavable or otherwise sterilizable metal or plastic. In addition, the body 204 of the dilator 202 may have any appropriate length to accommodate the patient's size, shape, and/or physiology. In one embodiment, the dilator 202 may be provided in a variety of lengths, allowing the surgeon to select in real-time the appropriate length for the patient.

Figure 8:
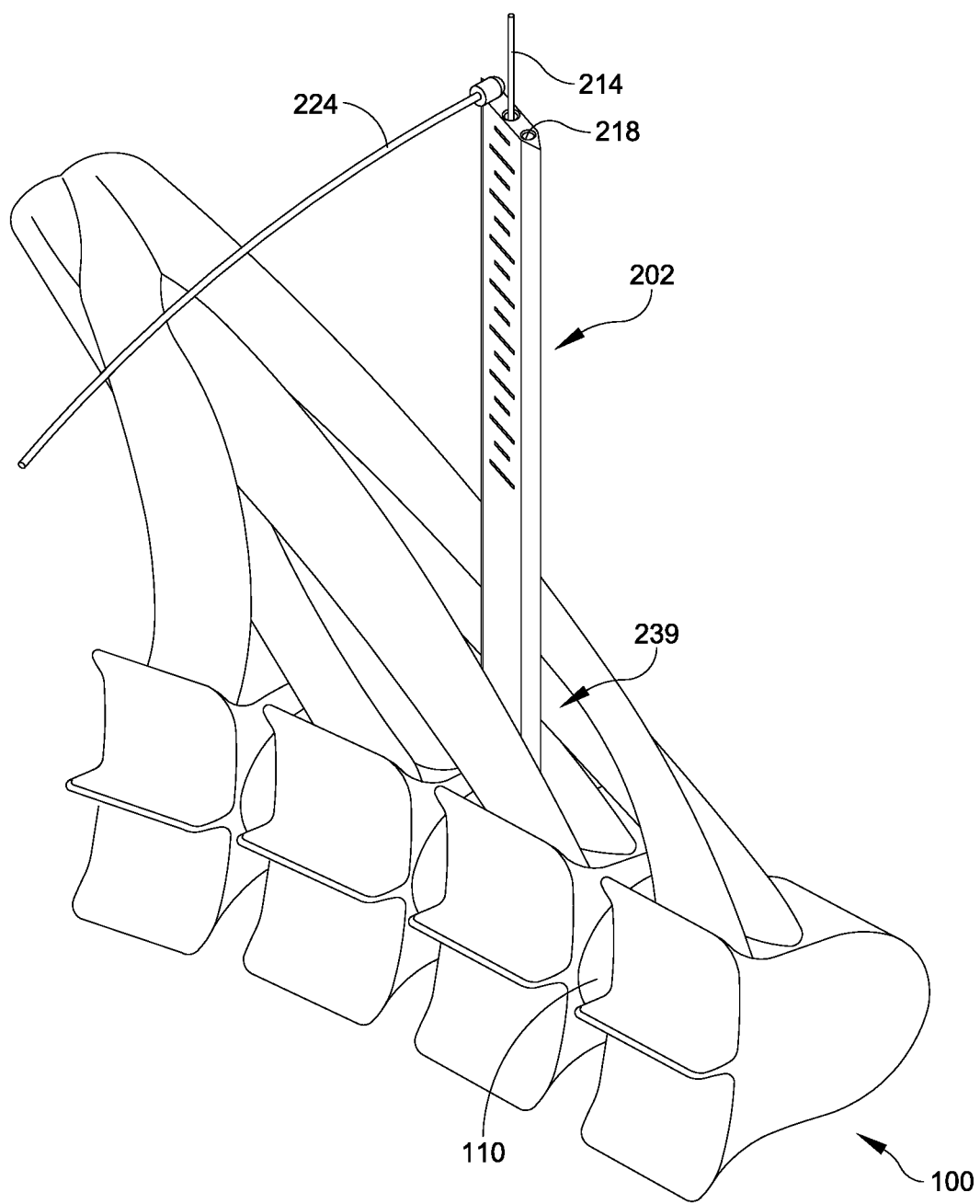
FIG. 8 illustrates a perspective view of the rectangular dilator of FIGS. 4-6, as inserted at the insertion orientation through the psoas muscle over the intervertebral disc space and having a monitor cable coupled with a conducting wire in electronic communication a neuromonitoring tip of the dilator.

Once the distal edge 210 of the dilator 202 is positioned at the spine 100 in the insertion orientation 239 that is parallel to the fibers of the psoas muscle 102 and spanning the disc space 110 diagonally at an approximate 45-degree angle, a K-wire 214 may be passed longitudinally through the access aperture 216 of the dilator 202 and into the spine 100 at the disc space 110 (FIG. 35A, 510), both stabilizing and securing the position of the dilator 202, as shown in FIGS. 6 and 8. Because of the active monitoring tip 222, the full range of monitoring—front to back and superior to inferior—may continue after the dilator 202 is fixed via the k-wire 214. Unlike previous devices featuring pinpoint electrodes that require manual rotation to perform 360 degrees of monitoring, the active monitoring tip 222 remains active and provides a geometry capable of monitoring in 360 degrees during every stage of its insertion and use during a procedure.

Figure 9:
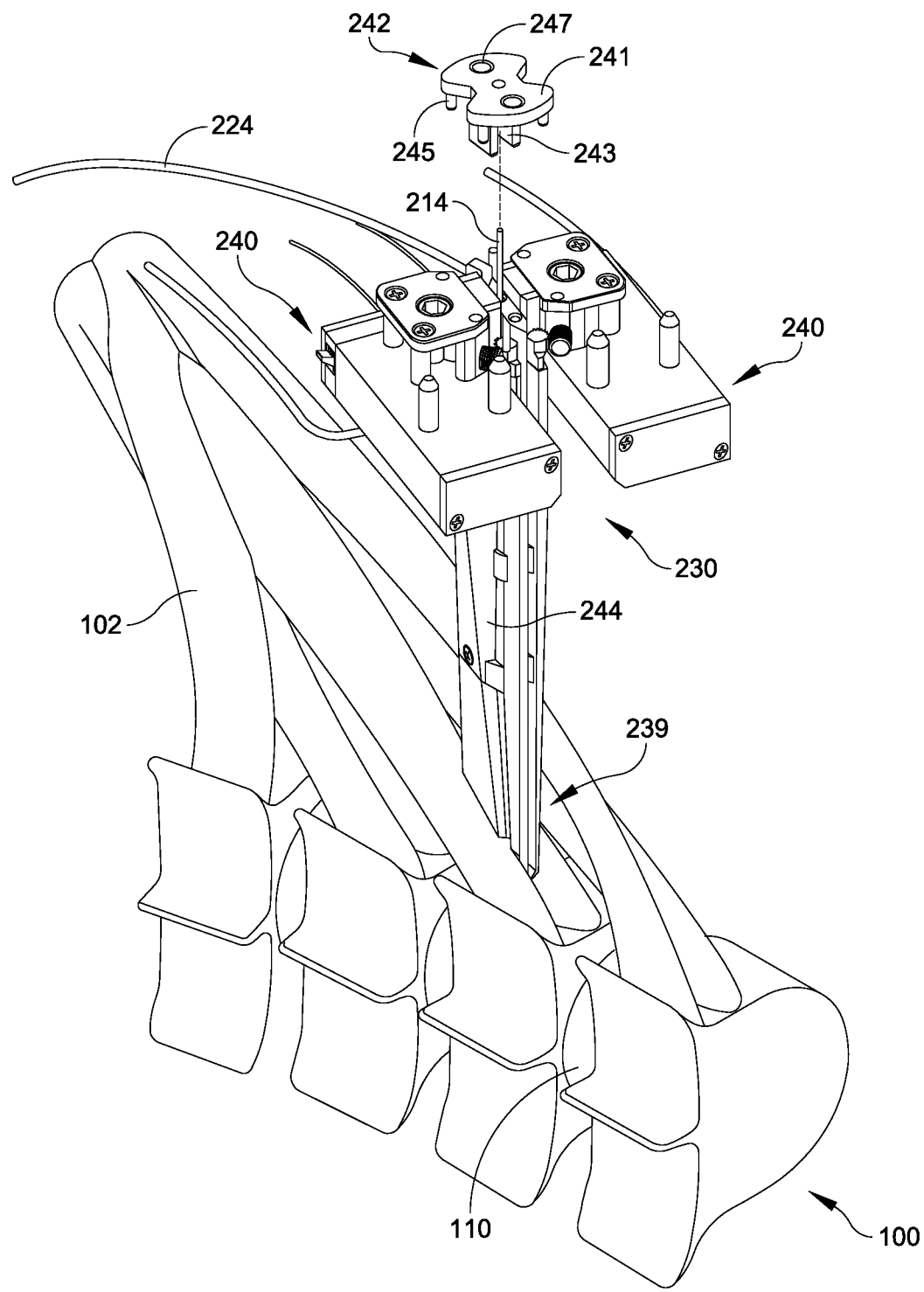
FIGS. 9-10 illustrate perspective and side views, respectively, of one embodiment of a dual-blade assembly passed over the inserted dilator of FIGS. 4-8 in the insertion orientation.
Figure 10:
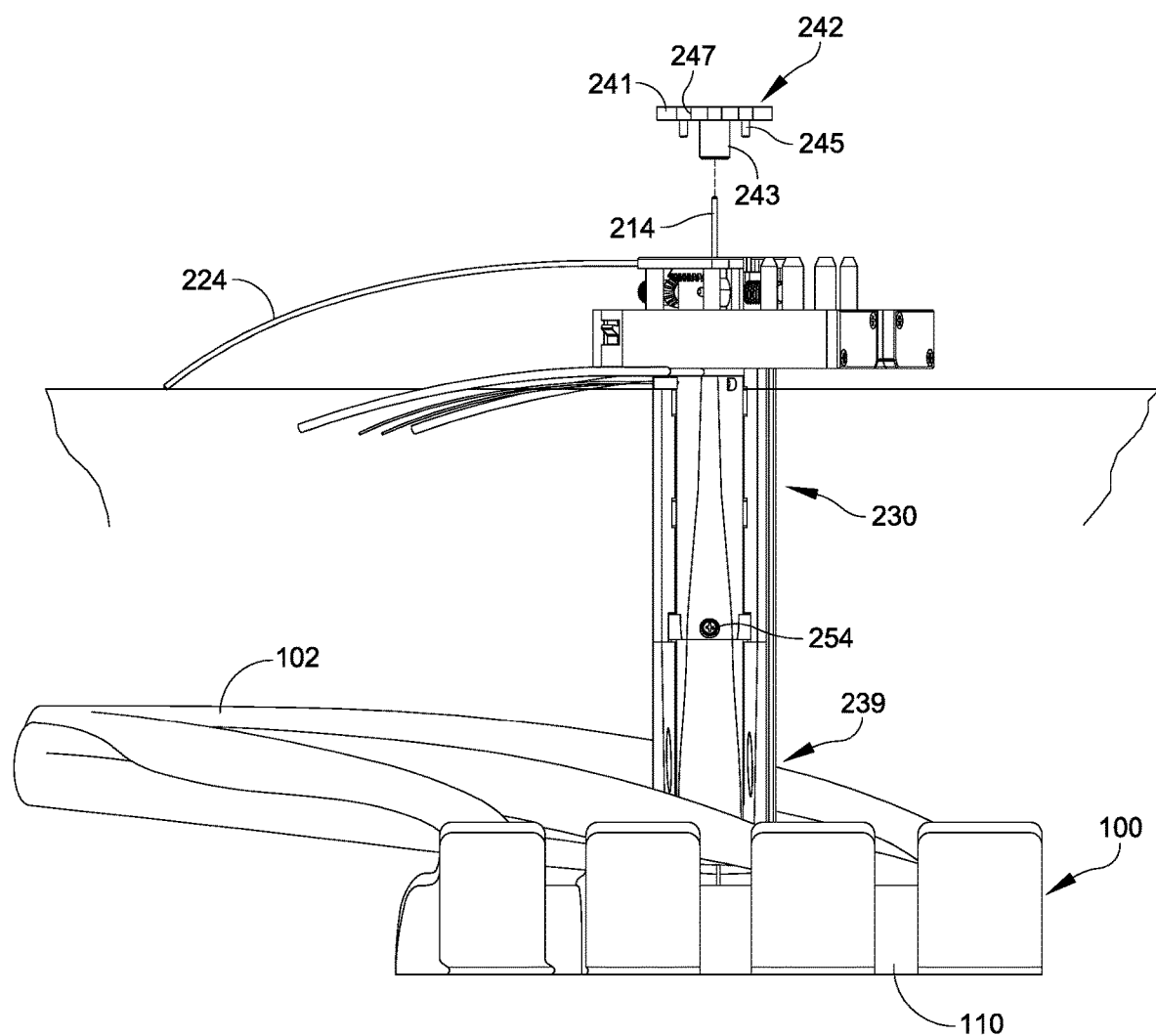

Referring to FIGS. 9-10, after securing the K-wire 214 (FIG. 35A, 510) into the disc space 110 of the spine 100 such that the dilator 202 is stabilized, secured, and providing continuous neuromonitoring, a dual-blade assembly 230 of a dual-blade lateral retractor system 200 (FIG. 32) may be passed over or introduced at the insertion orientation 239 alongside the dilator 202 such that each blade 244 of the dual-blade assembly 230 opposes and contacts one of the opposing flat surfaces 209 of the dilator 202 to further minimize damage to nerve structures and muscle fibers (FIG. 35A, 512).

As shown in FIGS. 9-10, the dual-blade assembly 230 may include two opposing and identical blade subassemblies 240 coupled to one another via a lower coupling device 242 configured to snap or press fit into receiving structures formed within each of the blade subassemblies 240. The lower coupling device 242 may include a platform 241 having a plurality of protrusions extending from a bottom of the platform 241 that are sized to be received by each of the blade subassemblies 240. The protrusions may include two opposing rectangular protrusions 243 and four opposing circular protrusions 245, each for insertion into a corresponding one of the blade subassemblies 240. The lower coupling device 242 may also include two circular receivers 247 formed within a top of the platform 241 and configured to receive components of additional functional assemblies that stack above the blade assembly 230, as detailed further below.

Figure 11:
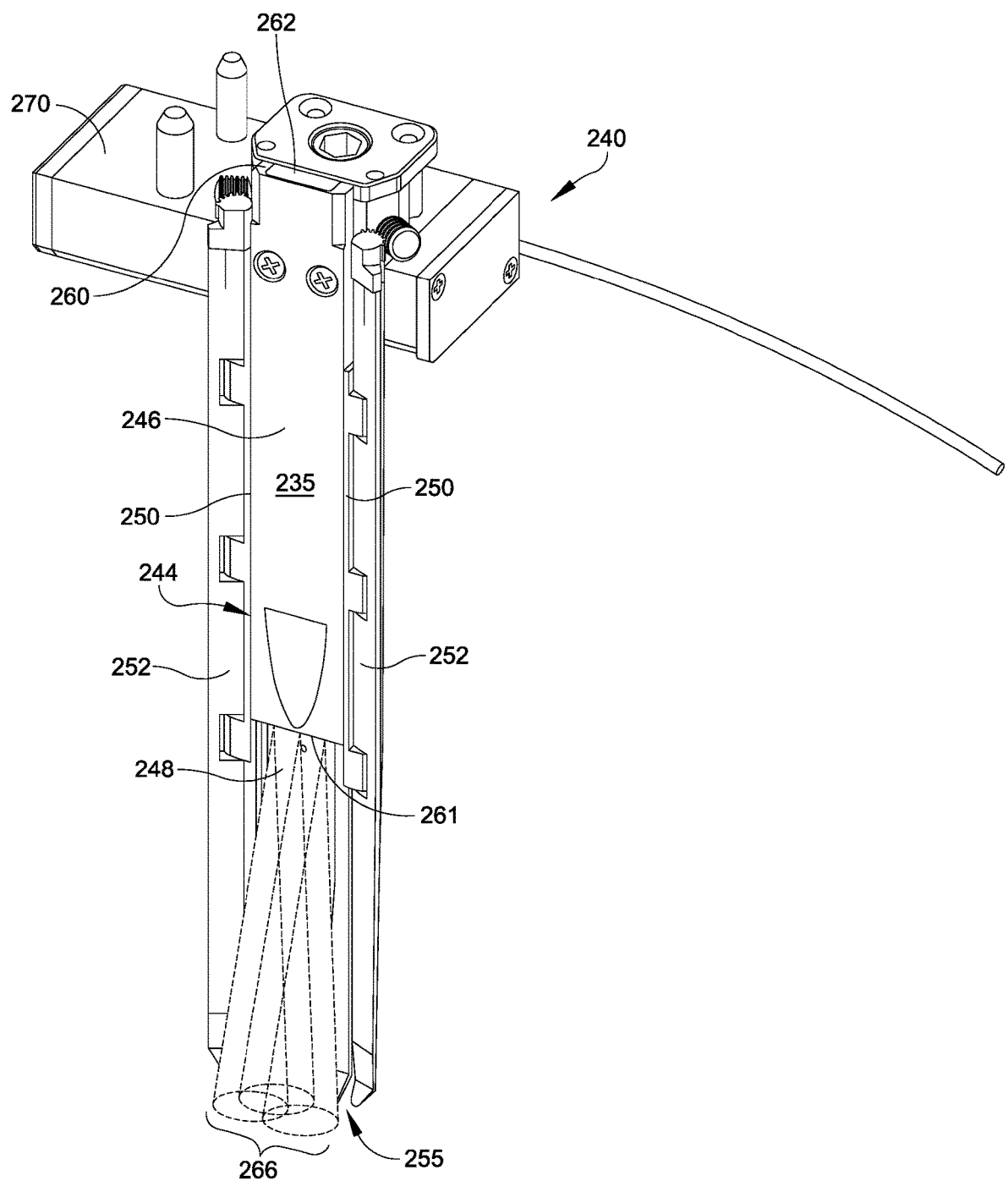
FIGS. 11-14 illustrate left-perspective, right-perspective, top-plan, and left-bottom-perspective views, respectively, of one embodiment of a blade subassembly of the dual-blade assembly of FIGS. 9-10.
Figure 12:
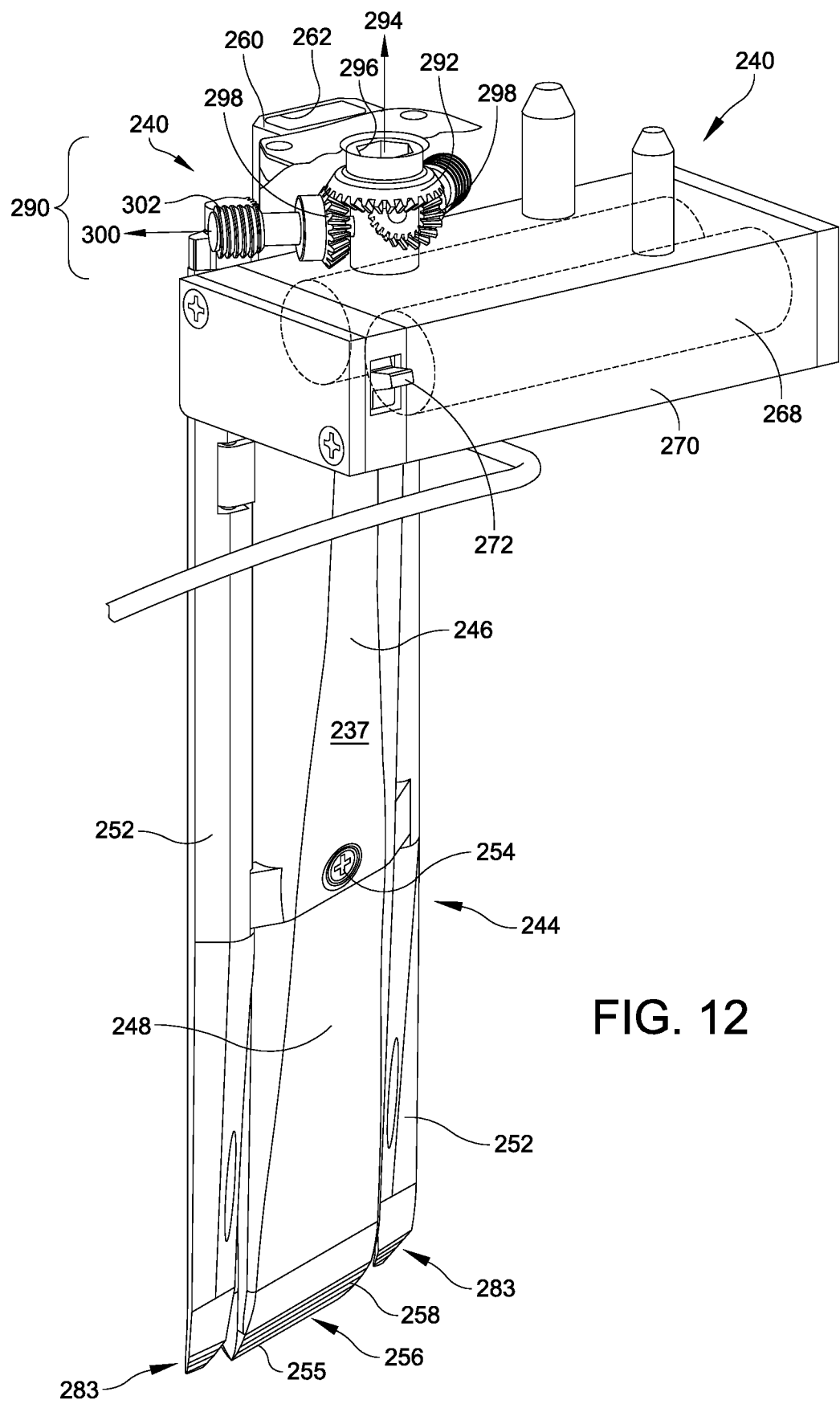
Figure 13:
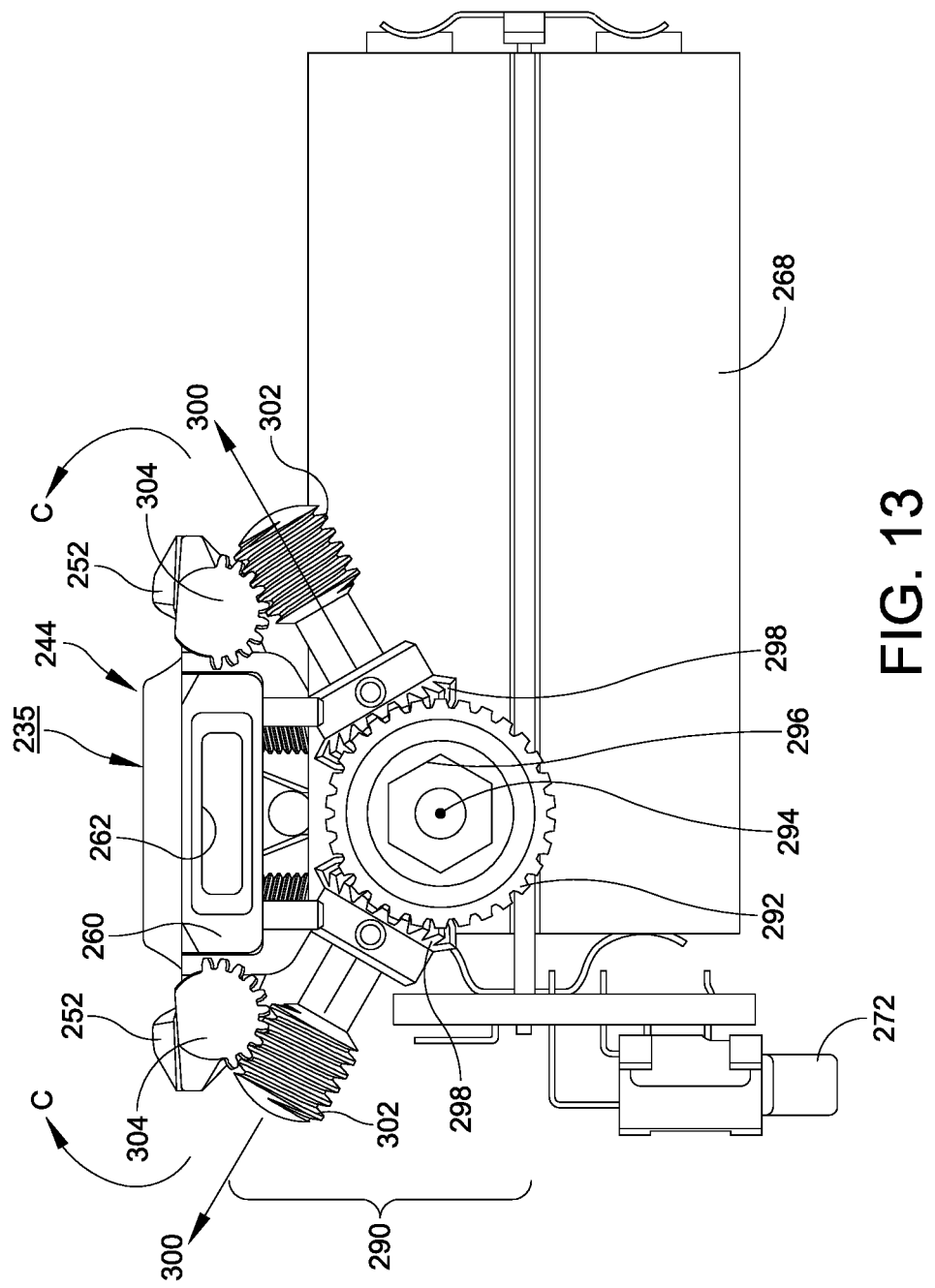

FIGS. 11-13 illustrate front-perspective, rear-perspective, and top-plan views of one exemplary embodiment of the blade subassembly 240, respectively. In this embodiment, the blade subassembly 240 may include a blade 244 having a planar inner surface 235 that faces the opposing blade 244 of the dual-blade assembly 230 (FIGS. 9-10), an outer surface 237, a proximal blade portion 246, a detachable distal blade portion 248, and opposing longitudinal edges 250 that extend between a proximal end 260 of the proximal blade portion 246 and a distal end 255 of the distal blade portion 248. Opposing adjustable wings 252 may be hingedly coupled with each of the opposing longitudinal edges 250, as detailed further below.

Turning to the blade 244, the detachable distal portion 248 may be a disposable, single-use insert of any appropriate length to accommodate the patient's size or physiology. In one embodiment, a plurality of detachable distal portions 248 may be provided in a peel pack (not shown), where each of the distal portions 248 contained within the peel pack feature a different length to accommodate a variety patient sizes and/or physiologies, which results in a variety of distances to traverse between the lateral surface 118 of the patient's body 108 and the spine 100. During use, the surgeon may select the detachable distal blade portion 248 with the appropriate length before attaching the select distal blade portion 248 to the reusable and sterilizable proximal portion 246 of the blade 244. The detachable distal portion 248 may attach to the reusable proximal portion 246 in any appropriate manner including, for example, a snap-fit of mating components or, as shown in FIG. 12, via an attachment screw 254 or another appropriate threaded fastener.

In one embodiment, the distal end 255 of the distal portion 248 of the blade 244 may form an active monitoring tip 256 similar to the active monitoring tip 222 of the dilator 202. In this regard, horizontal neurosensing wires 258 may be incorporated or built into the outer surface 237 of the blade 244 at the active monitoring tip 256. The horizontal neurosensing wires 258 may detect any impingement or encroachment upon nerve or plexus, and the resulting stimulus may be conducted through conducting wires embedded longitudinally in the blade, and through a monitoring cable for reporting to external equipment. Via the active monitoring tip 256 of each of the distal blade portions 248 of the blades 244, continuous real-time neuromonitoring may be performed to prevent nerve or plexus injury when the blade assembly 230 is inserted over the dilator 202 (FIG. 35A, 512, 514), as well as when the blade assembly 230 is rotated (FIG. 35A, 516) and/or laterally separated or retracted (FIG. 35A, 524), as discussed below. Unlike existing systems, neuromonitoring over a full 360-degree monitoring range may continue throughout the procedure.

The sterilizable and reusable proximal blade portion 246 may include a number of unique features that aid the surgeon. In one embodiment, the proximal end 260 of the proximal blade portion 246 may form a generally rectangular receiver 262 configured to receive one of the rectangular protrusions 243 of the lower coupling device 242 (FIGS. 9-10), which is adapted to temporarily couple the dual, opposing blade subassemblies 240 to one another during insertion and assist in rotating the blade subassemblies 240 from the insertion orientation 239 to a final, rotated orientation, as discussed below in relation to FIGS. 17-18.

Figure 14:
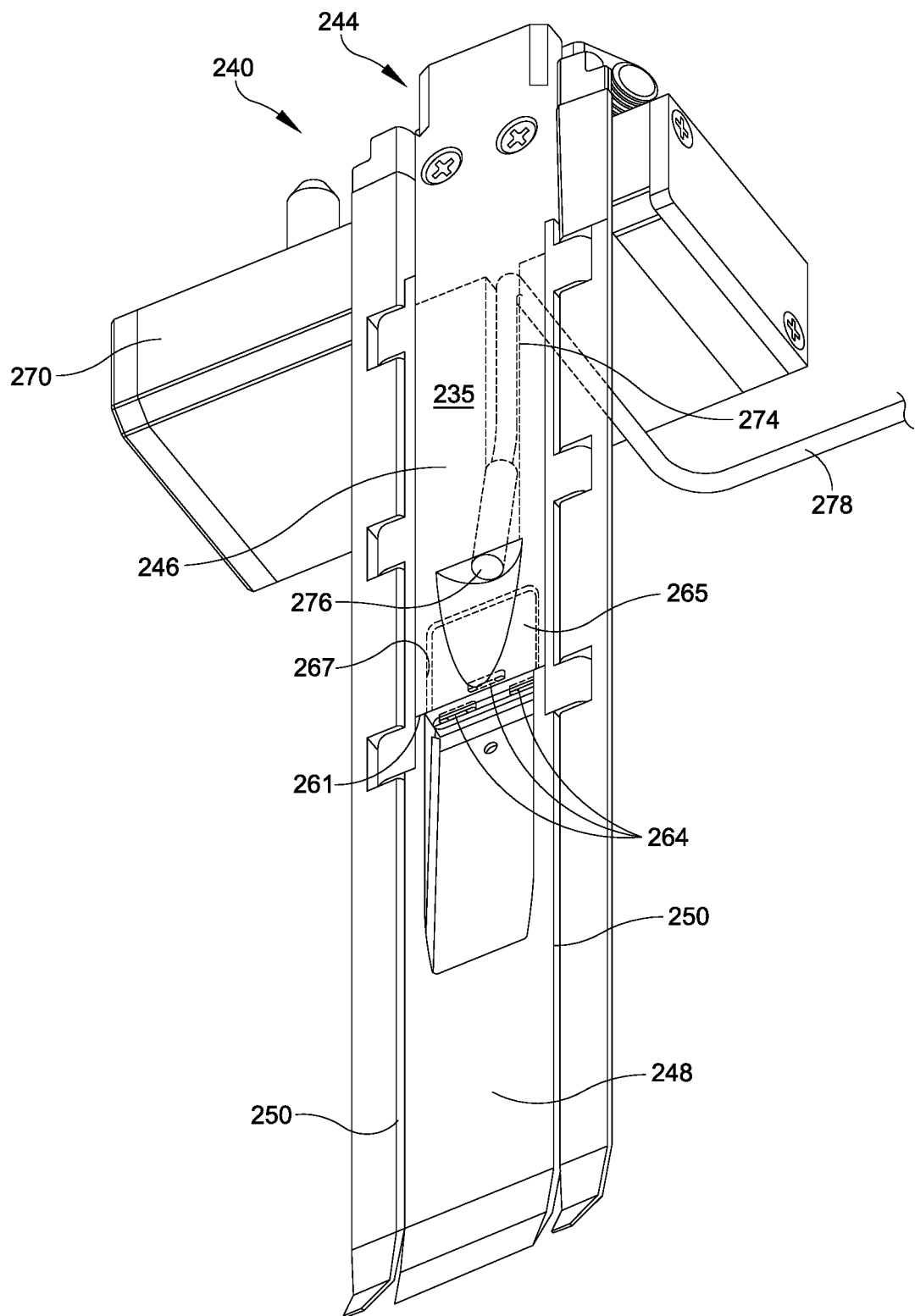

In addition, and referring to FIGS. 11-14, one or more light emitting diode (LED) lights 264 may be built into the proximal blade portion 246. As shown in FIGS. 11 and 14 and in this embodiment, three LED lights 264 may be positioned adjacent to the inner surface 235 of a distal end 261 of the proximal blade portion 246, such that the LED lights 264 illuminate a surgical area 266, as shown in FIG. 11. In one embodiment shown in FIG. 14, the LED lights 264 may be mounted to a printed circuit board (PCB) 265 housed within a PCB chamber 267 formed within the proximal blade portion 246 of the blade 244. The PCB 265 may incorporate control or interface circuitry that is, in turn, electrically coupled with a power source and a switch 272. In this embodiment, the power source may be one or more lithium ion batteries 268 housed within a battery housing 270 that is affixed in any appropriate manner to the outer surface 237 of the blade 244, as shown in FIGS. 11-13. The switch 272 may be electrically coupled between the batteries 268 and the PCB 265/LED lights 264, such that the switch 272 is configurable to control the lights 264 as necessary and/or desired by the surgeon. For example, the switch may be operated to illuminate a single one of the LED lights 264, a pair of the lights 264, or all of the LED lights 264 depending on the applicable light requirements and/or requisite run times.

Built-in lighting on the inner surfaces 235 of the blades 244 provides more accurate visualization for the surgeon due to the proximity of the light emitting source to the surgical field 266. The built-in lighting also eliminates the need for an external extension cord for lighting purposes, and prevents light projected from a separately attached light source, which is often attached to a proximal end of the apparatus, from reflecting off the blades and into the surgeon's eyes during operation.

The blade 244 may also include video capability to provide ergonomic operation for the surgeon. Specifically, and in one embodiment shown in FIG. 14, an interior of the proximal blade portion 246 may form a camera receiver channel 274 into which a video camera 276 (e.g., a commercially available micro-video camera) may be fed or positioned to provide a clear view of the surgical field 266. Images captured by the video camera 276 may be transmitted to one or more external monitors (e.g., flat screen television monitors) (not shown) via a video output 278 electronically coupled between the video camera 276 and the monitor(s). In one embodiment, the video camera 276/ video output 278 may employ wireless technology such as, for example, a Bluetooth, Zigbee, Wi-Fi or another appropriate transmitter or transceiver to communicate with the external monitoring devices. This video capability enables the surgeon to view his or her work within the surgical field 266 inside the dual-blade assembly 230 on the external monitors, and relieves the surgeon of the need to look straight down the assembly throughout the course of the procedure being performed.

As discussed above, each of the longitudinal edges 250 of the blade 244 may hingedly couple with an adjustable wing 252, as shown in FIGS. 11-14. As detailed below in relation to FIGS. 25-31, the adjustable wings 252 may be rotated or adjusted through 90 degrees relative to the inner surface 235 of the blade 244—from an open position 280 that is parallel with the blade 244 (FIGS. 25-27) to a closed position 282 that is perpendicular to the blade 244 (FIG. 30), and any position therebetween (FIGS. 28-29). This adjustment from the open position 280 to the closed position 282 essentially sections off the muscle surrounding the dual-blade assembly 230 as the blades 244 are separated or retracted away from one another, thereby preventing any "creep" of the muscle between the blades during retraction and enabling the dual-blade assembly 230 to accomplish what has previously required additional blades (e.g., multiple blades beyond two, a circular or radial blade configuration) to complete.

FIGS. 12-13 illustrate a perspective view of the blade subassembly 240 and a top view of the blade subassembly 240 with the battery housing 270 removed, respectively. Specifically, FIGS. 12-13 detail an exemplary actuation assembly 290 for the adjustable wings 252 on each blade 244. In this embodiment, the actuation assembly 290 may include a central miter gear 292 positioned horizontally such that a center axis 294 defined by the central miter gear 292 runs parallel to the blade 244. A top of the central miter gear 292 may form a hexagonal socket 296 configured to receive an actuating hex key (not shown), which may take the form of a removeable manual handle such as handles 310 and 316, discussed below in relation to the rotation and lateral retraction assemblies.

The central miter gear 292 may be enmeshed between two opposing vertical miter gears 298, each defining a center axis 300 that is perpendicular to and that intersects the center axis 294 of the central miter gear 292. Each of the vertical miter gears 298 may be affixed to a worm screw 302 that is, in turn, enmeshed with a corresponding worm wheel 304 affixed to a proximal end of the associated adjustable wing 252. To operate, the hex key/handle may be rotated within the hexagonal socket 296 to rotate the central miter gear 292, which, in turn rotates the vertical miter gears 298, the attached worms screws 302, and the corresponding worm wheels 304 affixed each adjustable wing 252 to move the wings 252 through 90 degrees in the direction of arrow C relative to the inner surface 235 of the blade 244, as shown in FIGS. 25-31.

Like the lower blade portion 248, the adjustable wings 252 may be single-use components that vary in length based upon an overall length of the blade 244 required to accommodate the patient's size and/or shape. Moreover, each of the adjustable wings 252 may form an active monitoring tip 283 (FIG. 12) on its outer surface similar to the active monitoring tips 222 and 256 of the dilator 202 and the blade 244, respectively.

Figure 15:
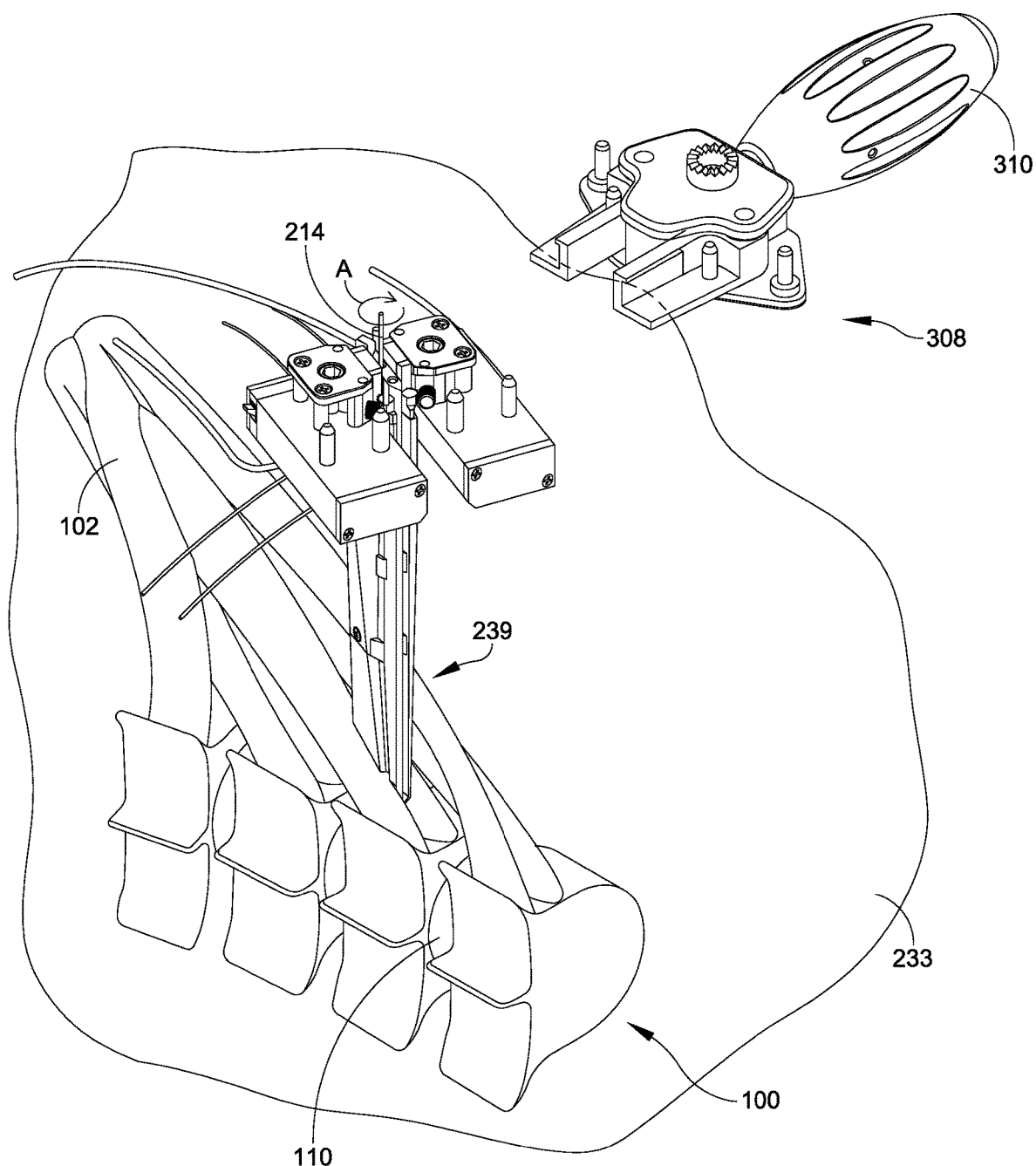
FIG. 15 illustrates a perspective view of the dual-blade assembly of FIGS. 9-10 installed in the insertion orientation, without a lower coupling device and disposed upon a surgical table in preparation for connection with a lateral retraction gearbox.
Figure 16:
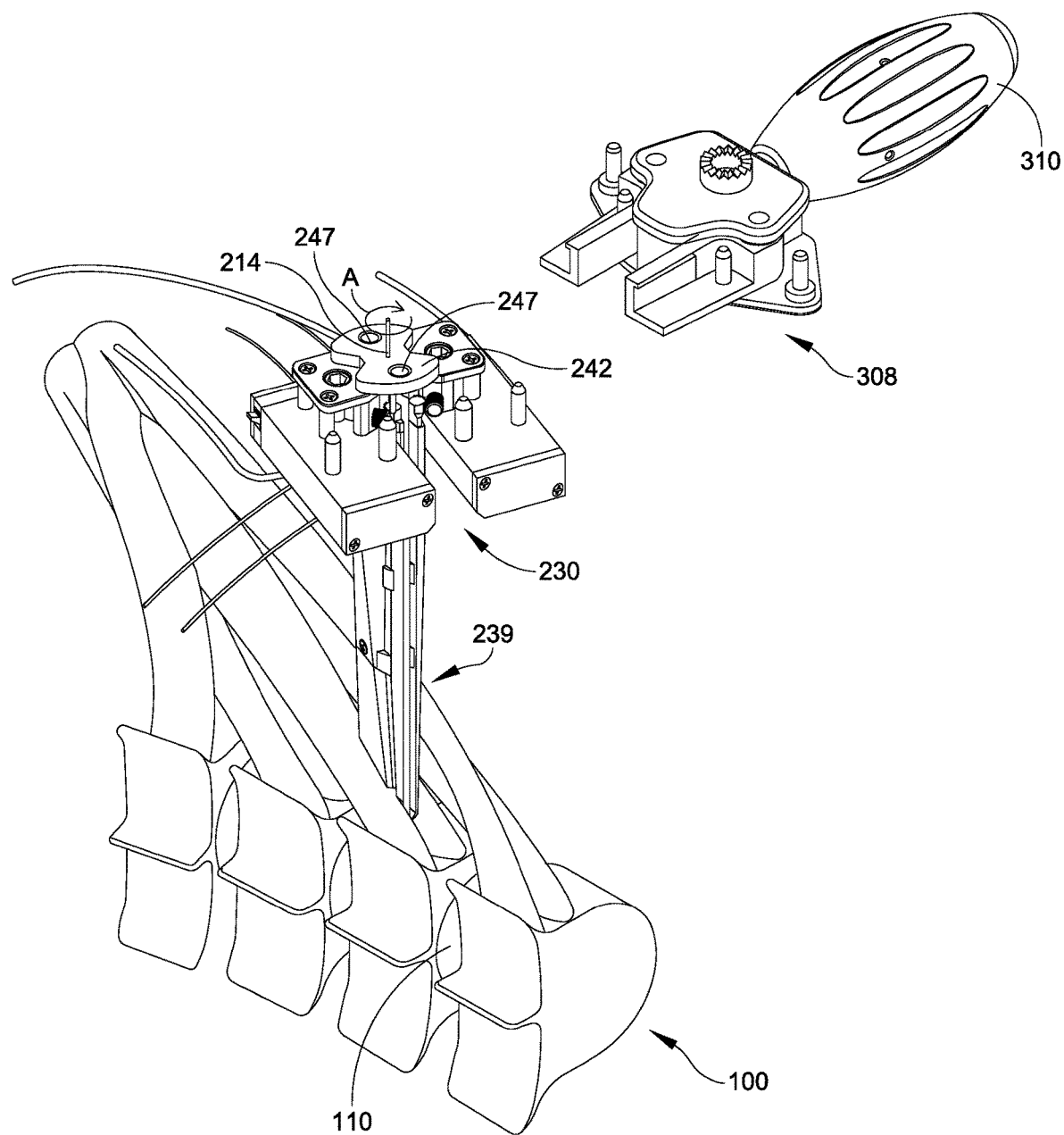
FIG. 16 illustrates a perspective view of the dual-blade assembly of FIGS. 9-10 including a lower coupling device attaching two of the blade subassemblies of FIGS. 11-14, in preparation for connection with the lateral retraction gearbox of FIG. 15.
Figure 17:
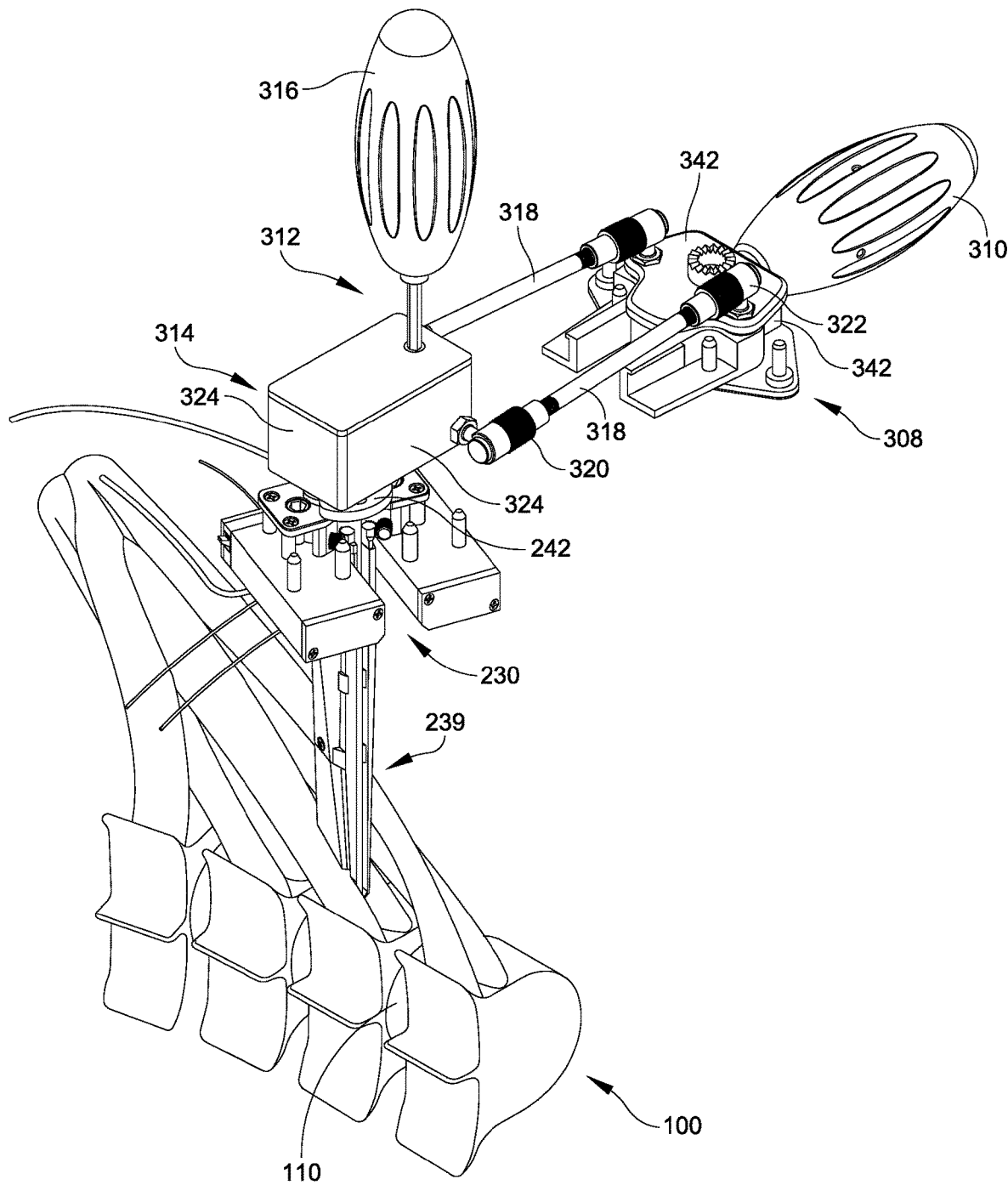
FIG. 17 illustrates a perspective view of the dual-blade assembly of FIG. 16 in the insertion orientation, connected to the lateral retraction gearbox of FIGS. 15-16 via one embodiment of a rotation assembly.
Figure 18:
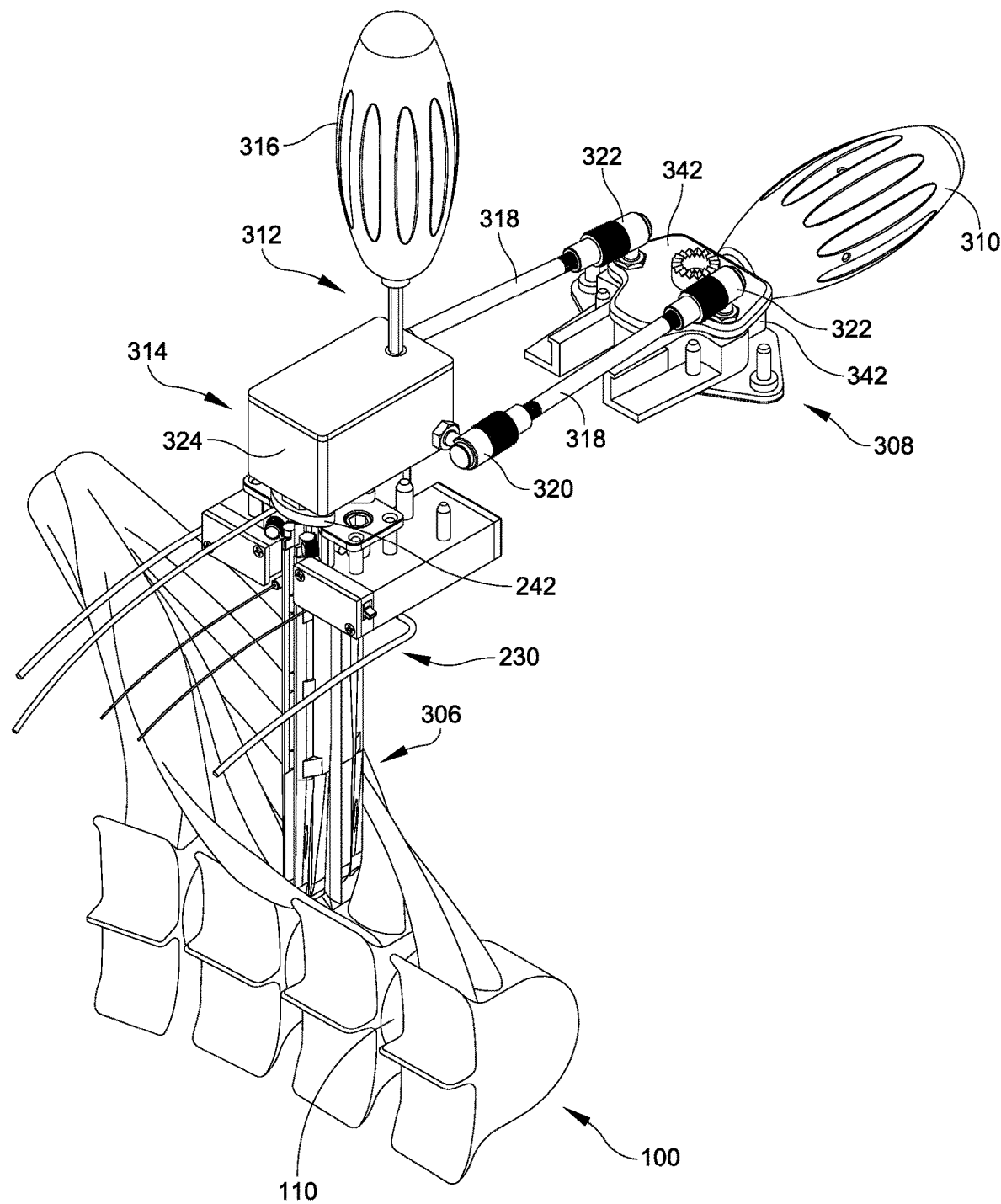
FIG. 18 illustrates a perspective view of the connected dual-blade assembly, lateral retraction gearbox, and rotation assembly of FIG. 17, with the dual-blade assembly rotated to a final rotated orientation via the rotation assembly.

Returning to the method and in relation to FIGS. 15-19, after the dual-blade assembly 230 is passed over the dilator 202 in a direction along the fibers of the psoas muscle 102 (FIG. 35A, 512), the dual-blade assembly 230 may be rotated approximately 45-50 degrees in the direction of arrow A about the K-wire 214, from its initial insertion orientation 239 parallel to the fibers of the psoas muscle 102, shown in FIGS. 15-17, to a final rotated orientation 306 parallel to the disc space 110, in which the blades 244 of the dual-blade assembly 230 are positioned transverse to the fibers of the psoas muscle 102 and begin to separate the fibers of the psoas muscle 102, as shown in FIG. 18 (FIG. 35B, 516).

To rotate the dual-blade assembly 230 from the insertion orientation 239 to the rotated orientation 306 (FIG. 35B, 516), additional assemblies may be operably coupled with the dual-blade assembly 230, as shown in FIGS. 15-19. Initially, a lateral actuation gearbox 308 and an actuating handle 310 may be securely attached to a fixed reference point such as a surgical table 233 via a standard tooth jaw and universal joint mechanism (not shown) (FIG. 35B, 518), as shown in FIG. 15. Then a rotation assembly 312 may be coupled between the blade assembly 230 and the lateral actuation gearbox 308 (FIG. 35B, 520).

Figure 19:
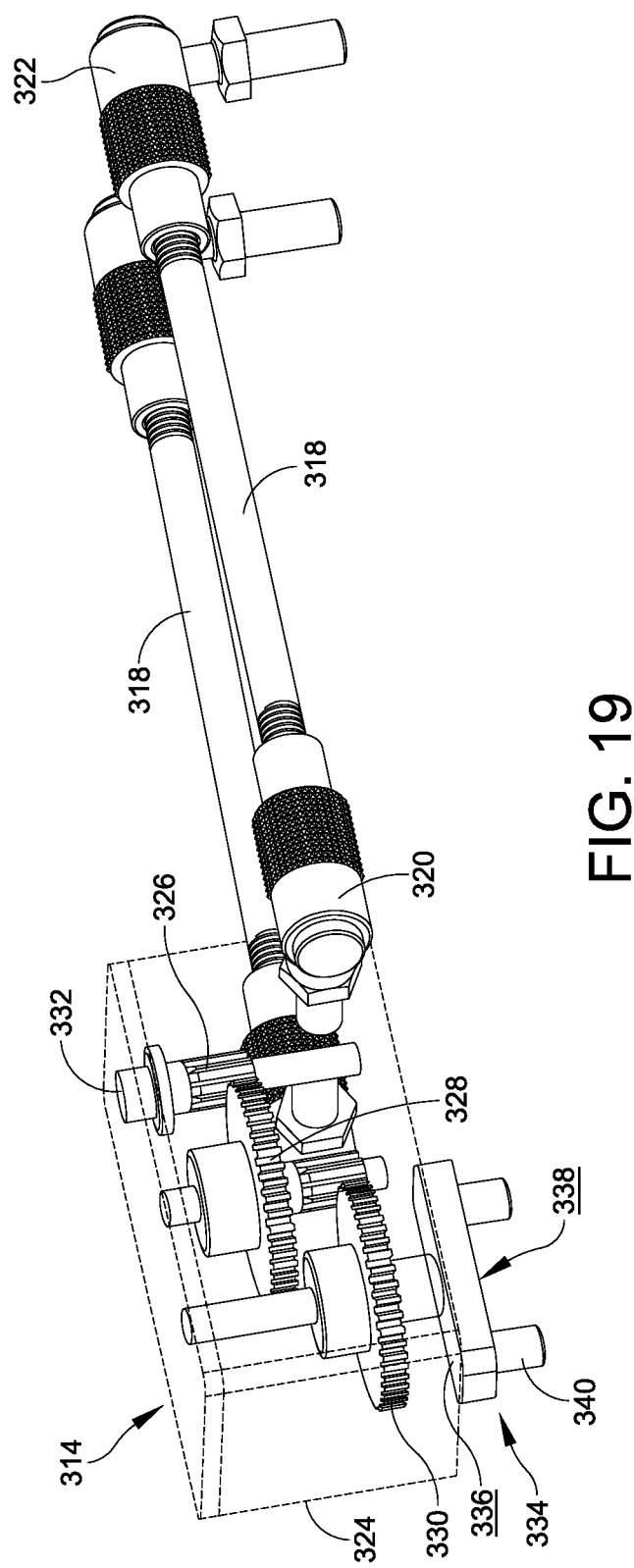
FIG. 19 illustrates a perspective view of one embodiment of a rotation gearbox and connecting rods of the rotation assembly of FIGS. 17-18.

In further detail and in one embodiment shown in FIGS. 17-19, the rotation assembly 312 may include a rotation gearbox 314, an actuating handle 316, and a pair of connecting rods 318 coupled between the rotation gearbox 314 and the lateral actuation gearbox 308, each having a first end 320 affixed to the a housing 324 of the rotational gearbox 314 and a second end 322 affixed to a housing 342 of the lateral actuation gearbox 308. The first and second ends 320, 322 of the connecting rods 318 may be affixed to the rotational gearbox housing 324 and the lateral actuation gearbox housing 342, respectively, in any appropriate manner including, for example, via threaded fasteners.

FIG. 19 illustrates a perspective view of one embodiment of the rotation gearbox 314 and the connecting rods 318, with the housing 324 of the rotation gearbox 314 in which the housing 324 is shown in wireframe to reveal the details of the gearbox 314. In this embodiment, the rotation gearbox 314 may contain first, second, and third rotational gears 326, 328, 330, respectively, that are rotationally mounted relative to one another within the housing 324. The first rotational gear 326 may include a hexagonal or other appropriately configured socket 332 adapted to receive a distal end of the handle 316, which, in this embodiment, may be configured as a hex key. The third rotational gear 330 may be affixed to an upper coupling device 334 having a top surface 336 adapted to attach to the third rotational gear 330 and a bottom surface 338 having two circular protrusions 340 extending therefrom. Each of the circular protrusions 340 may, when the rotation gearbox 314 is assembled to the blade assembly 230 as shown in FIGS. 17-18, extend into the circular receivers 247 of the lower coupling device 242 of the blade assembly 230, shown in FIG. 16 and detailed above in relation to FIGS. 9-10.

Once the rotation assembly 312 is coupled between the blade assembly 230 and the lateral actuation gearbox 308 (FIG. 35B, 520), as shown in FIG. 17, the handle may be manually actuated (FIG. 35B, 522) to turn the first rotational gear 326, which, in turn, rotates the enmeshed second rotational gear 328 and then the enmeshed third rotational gear 330. Because the lateral actuation gearbox 308, the connecting rods 318, and the rotation gearbox 314 are fixed relative to the operating table (not shown), rotation of the third rotational gear 330 causes the upper coupling device 334 to turn the attached lower coupling device 242 about the K-wire 214, which causes the two attached blade subassemblies 240 to rotate in the direction of arrow A (FIGS. 15-16) from the initial insertion orientation 239 of FIG. 17 to the final rotated orientation 306 of FIG. 18.

Figure 20:
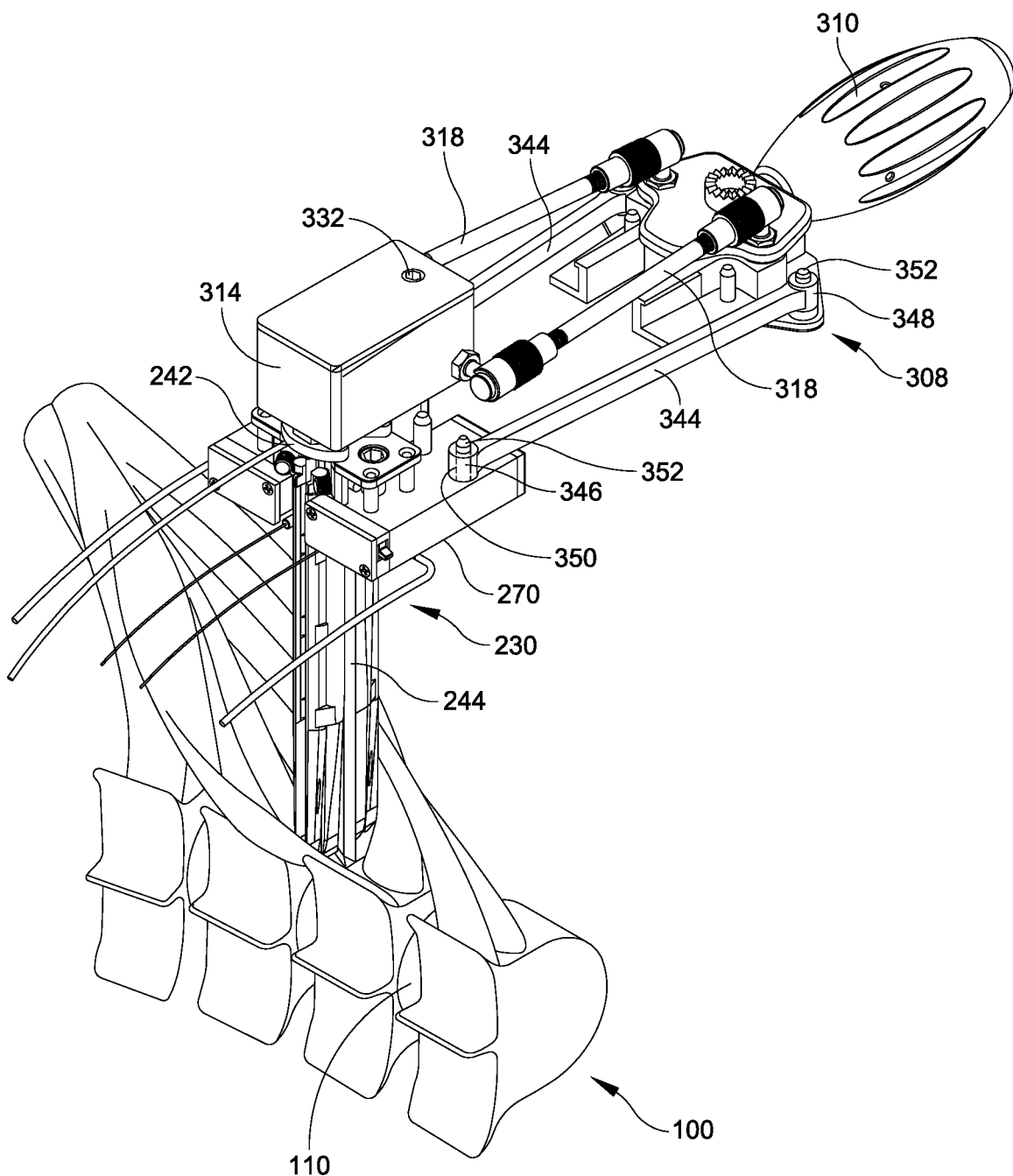
FIG. 20 illustrates a perspective view of the connected dual-blade assembly, lateral retraction gearbox, and rotation assembly of FIGS. 17-18, with a handle of the rotation assembly removed and an embodiment of a pair of opposing passive lateral arms coupled between the dual-blade assembly and the lateral retraction gearbox.
Figure 21:
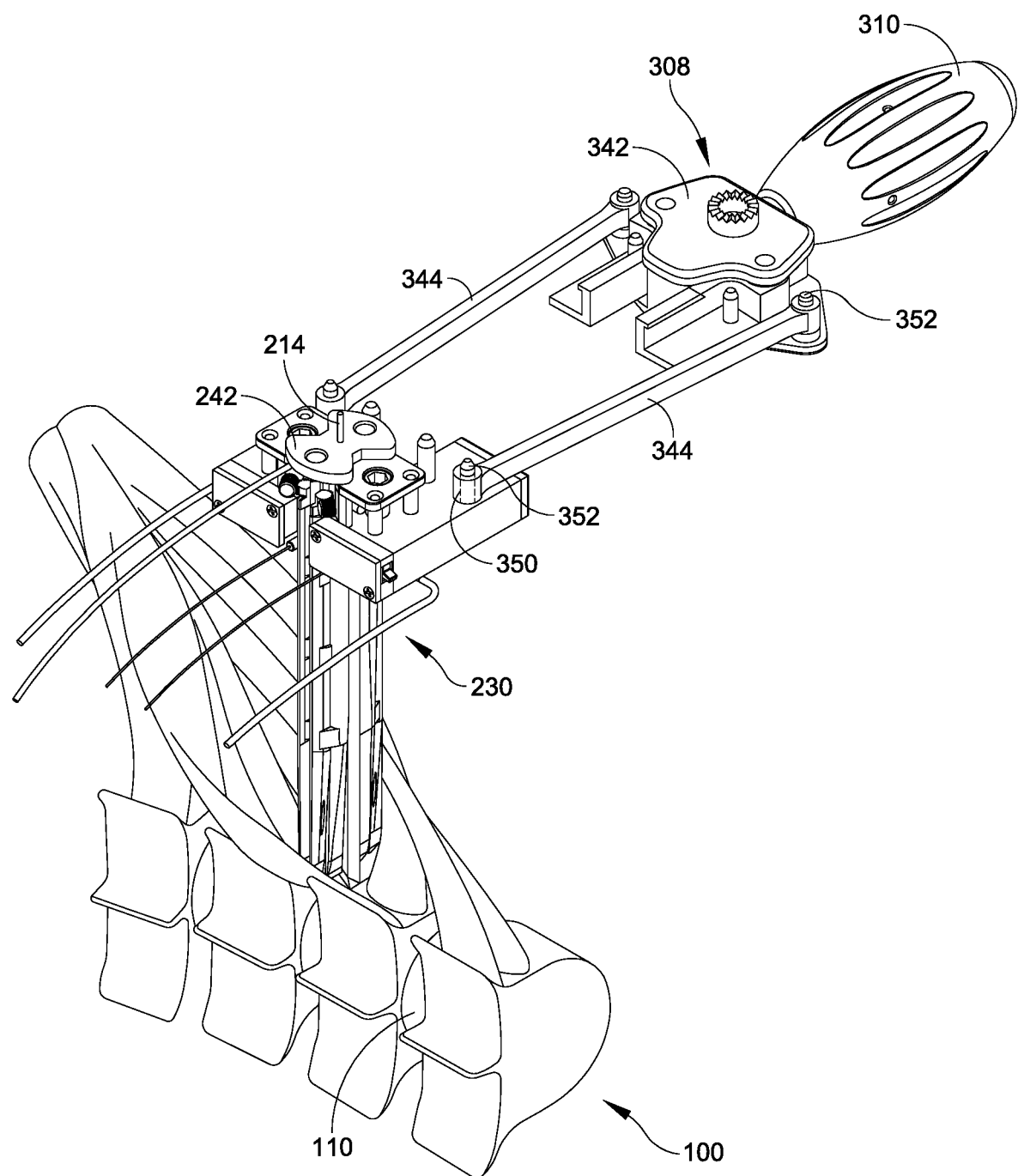
FIG. 21 illustrates the assembly of FIG. 20, with a gearbox of the rotation assembly removed.

After the dual-blade assembly 230 has been rotated into the final rotated orientation 306 (FIG. 35B, 516), the system may be reconfigured for separation, or lateral retraction, of the two opposing blade subassemblies 240 via the steps illustrated in FIGS. 20-25 (FIG. 35B, 524). First, and as shown in FIG. 20, a pair of opposing passive lateral arms 344 may be attached between the lateral actuation gearbox 308 and the battery housings 270 of the blade subassemblies 240 (FIG. 35B, 526). Each of the passive lateral arms 344 may have a first end 346 that is rotationally coupled with one of the battery housings 270 and a second end 348 that is rotationally coupled with the housing 342 of the lateral actuation gearbox 308, such that the passive lateral arms 344 may provide stabilization to the blade assembly 230 as the rotation gearbox 314 is removed, as shown in FIG. 21, as well as passively accommodate the lateral separation of the blade subassemblies 240, as discussed further below in relation to FIGS. 26-31. The rotational couplings between the passive lateral arms 344, the battery housings 270, and the lateral actuation gearbox 308 may take any appropriate shape, configuration, or type. In this embodiment, the first and the second ends 346, 348 of each of the passive lateral arms 344 may form a receiver 350 configured to receive a corresponding protrusion 352 extending from the battery housing 270 and from the lateral actuation gearbox 308 via a friction fit.

Figure 22:
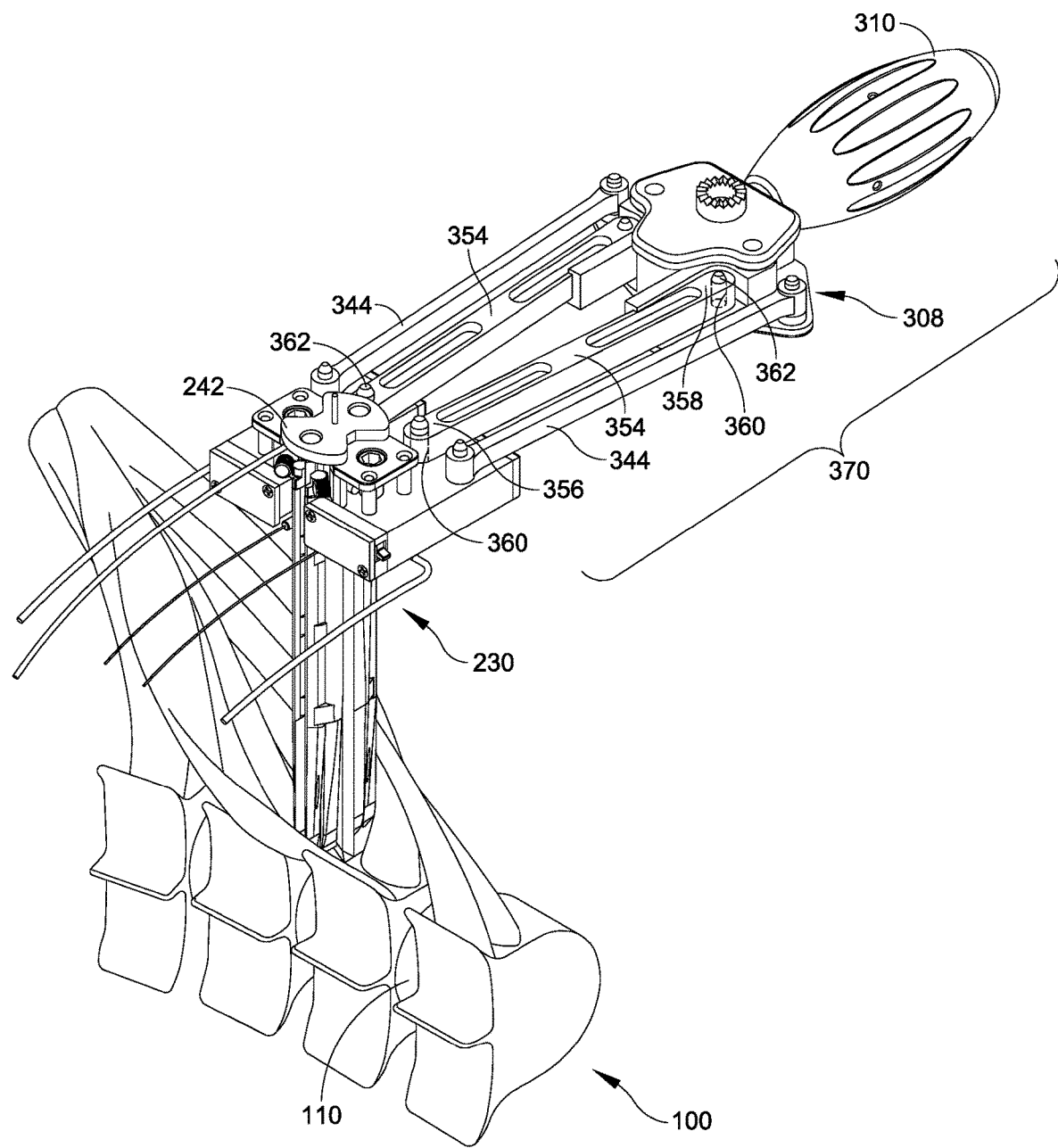
FIG. 22 illustrates a perspective view of the assembly of FIG. 21, with one embodiment of a pair of opposing lateral drive arms coupled between the dual-blade assembly and the lateral retraction gearbox.

Once the passive lateral arms 344 are attached (FIG. 35B, 526), the rotation assembly 312, including the rotation gearbox 314, the manual handle 316, and the connecting rods 318, may be removed as shown in FIGS. 20-21 by disengaging the upper and the lower coupling devices 334 and 242, all the while relying on the passive lateral arms 344 for stabilization of the blade assembly 230 during removal (FIG. 35B, 528). Then a pair of opposing lateral drive arms 354 may be coupled between the lateral actuation gearbox 308 and the battery housings 270 of the blade subassemblies 240 (FIG. 35B, 530), as shown in FIG. 22. Each of the lateral drive arms 354 may have a first end 356 that is rotationally coupled to one of the battery housings 270 of the blade subassemblies 240 and a second end 358 that is rotationally coupled to the housing 342 of the lateral actuation gearbox 308. These rotational couplings may take any appropriate form, though in one embodiment, they may mimic the structure of the rotational couplings of the passive lateral arms 344 in that each of the first and the second ends 356, 358 may form a receiver 360 configured to receive a corresponding protrusion 362 extending from the battery housing 270 and from the lateral actuation gearbox housing 342, respectively, via a friction fit.

Figure 23:
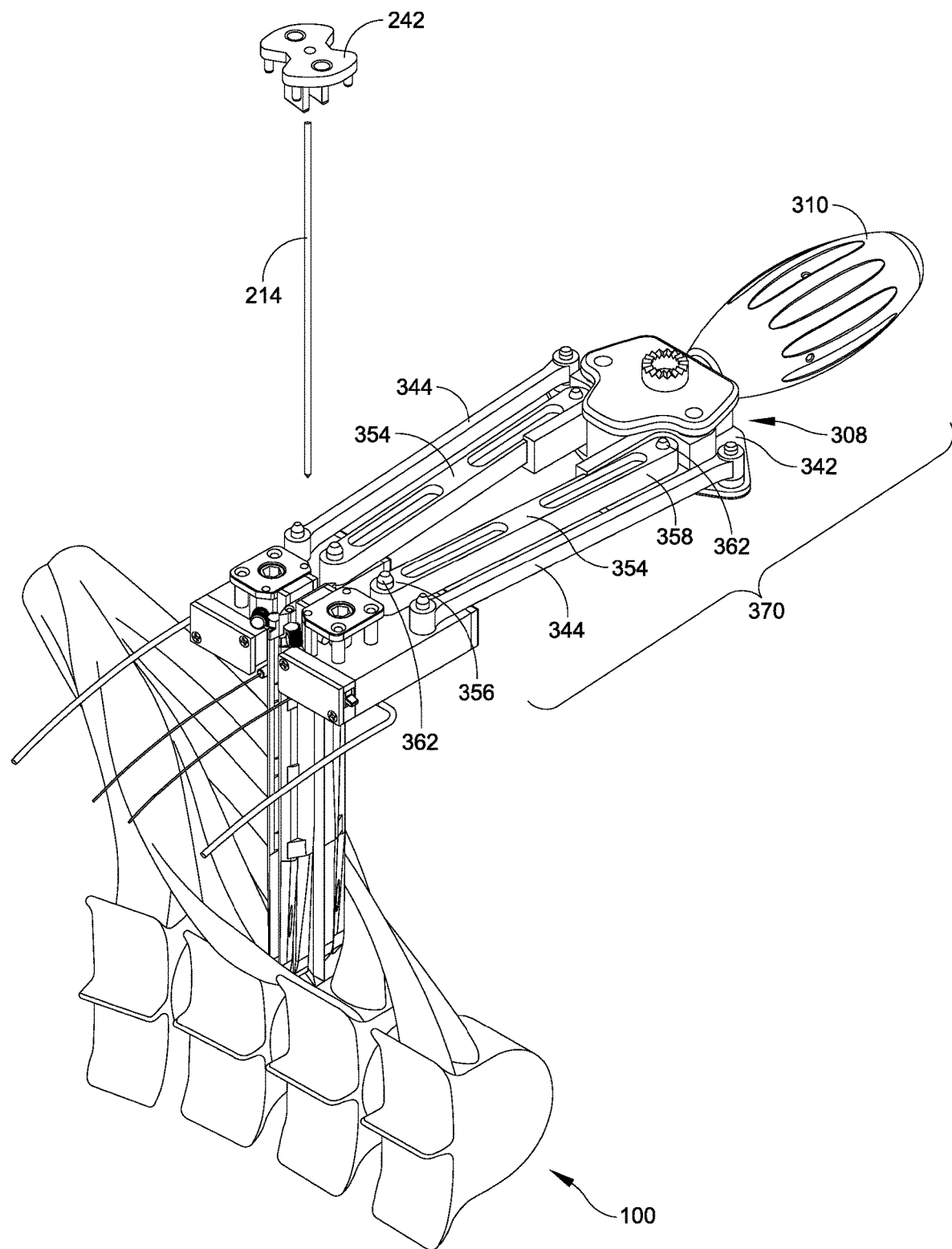
FIG. 23 illustrates a perspective view of the assembly of FIG. 22, with a K-wire and a lower coupling device removed from the dual-blade assembly to an exploded position.
Figure 24:
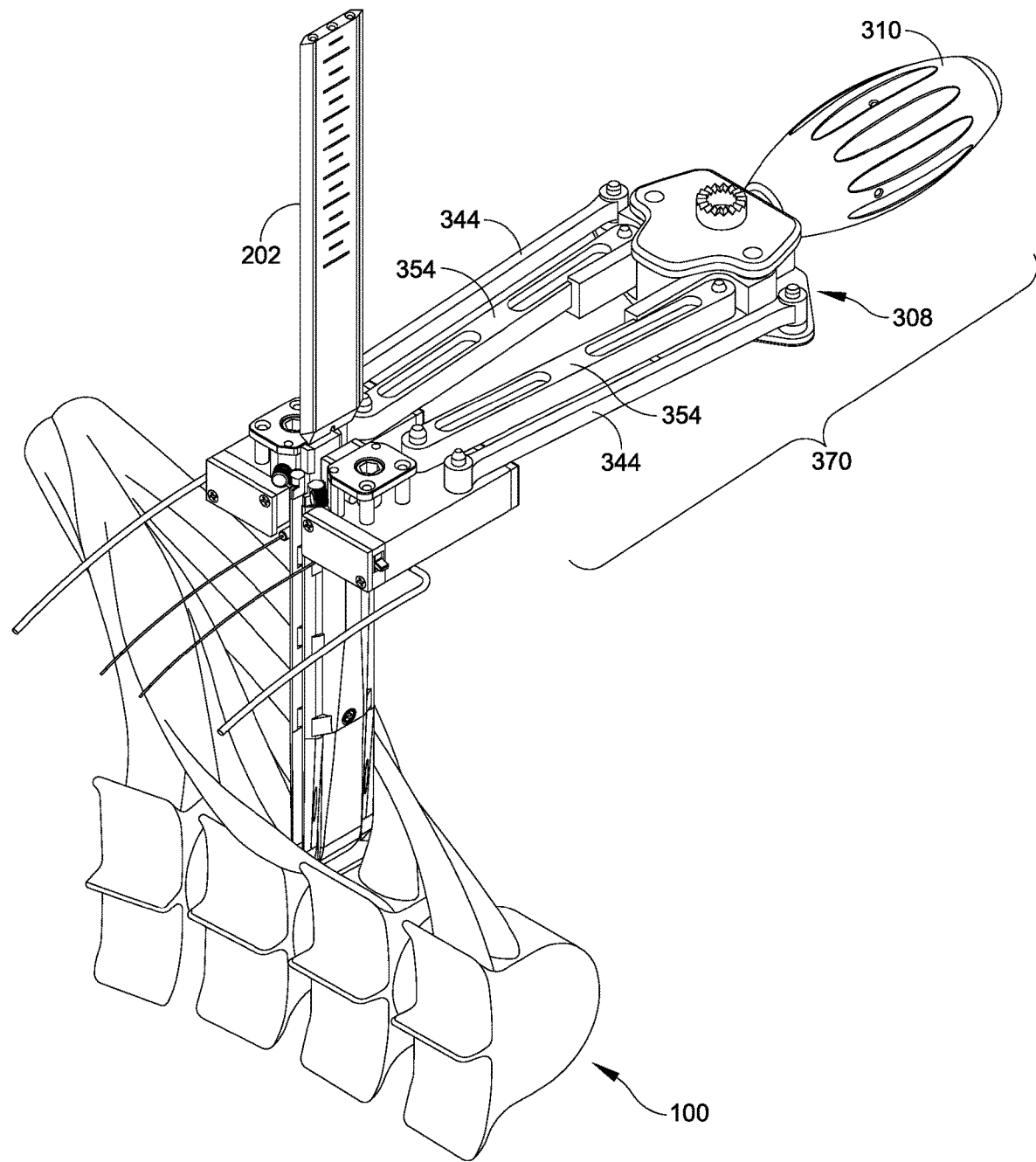
FIG. 24 illustrates a perspective view of the assembly of FIG. 23, with the dilator of FIGS. 4-8 removed to an exploded position.

After the lateral drive arms 354 are attached, the K-wire 214 and the lower coupling device 242 may be removed, as shown in FIG. 23 (FIG. 35B, 532), followed by the dilator 202, as shown in FIG. 24 (FIG. 35B, 534).

Figure 25:
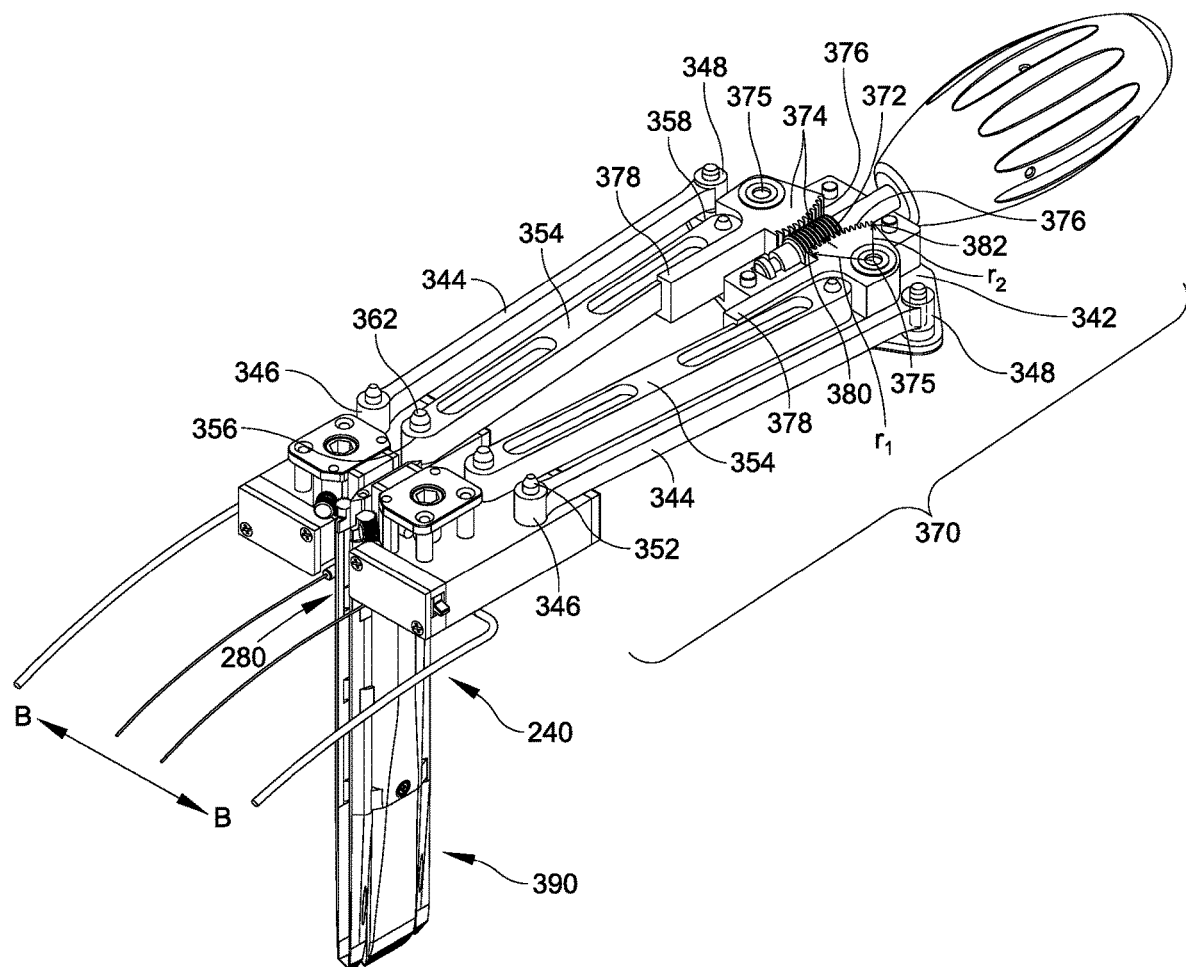
FIG. 25 illustrates a perspective view of the assembly of FIG. 24, with a housing of the lateral actuation gearbox removed to reveal one embodiment of a lateral retraction gear chain operating within the housing.
Figure 26:
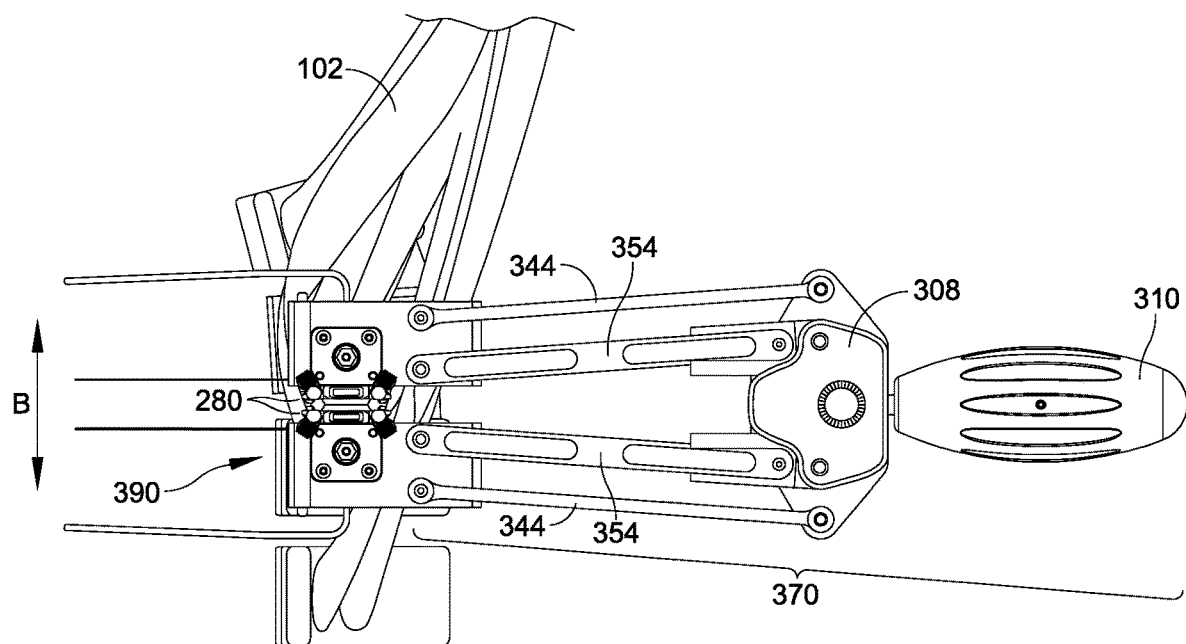
FIGS. 26-27 illustrate top views of two adjacent blade subassemblies of FIGS. 11-14 coupled with one embodiment of a lateral retraction assembly and in a closed blade position.
Figure 27:
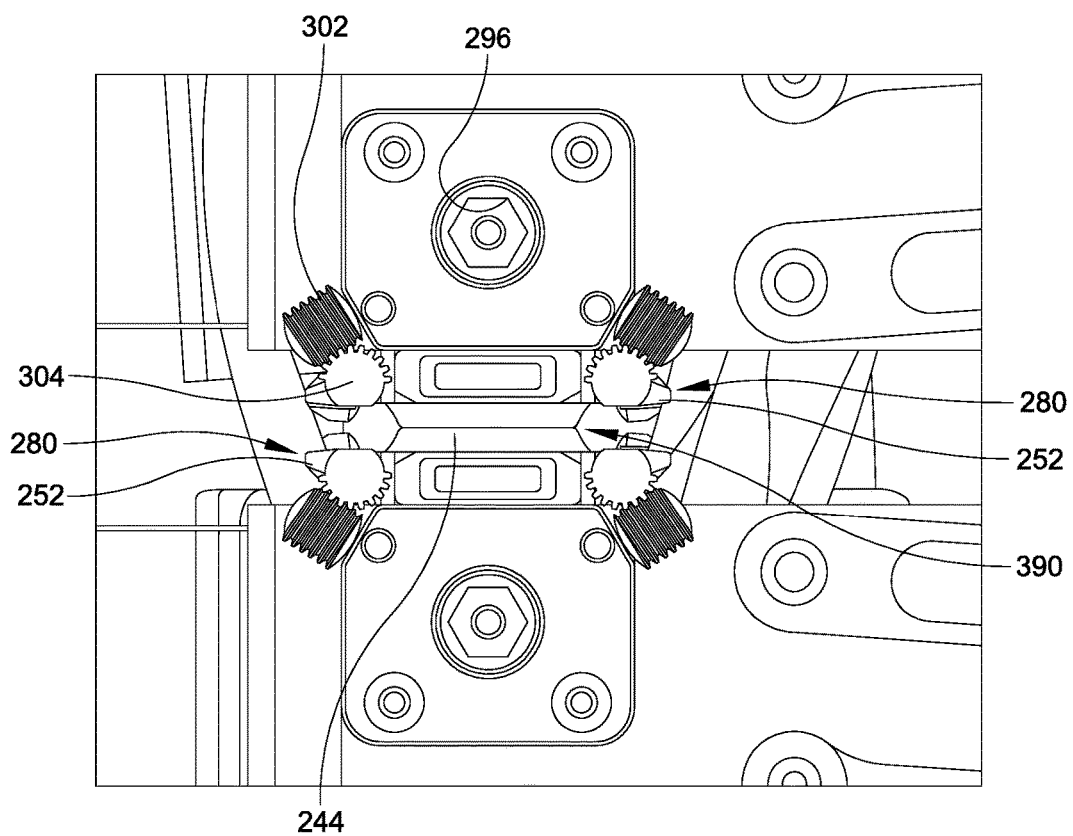
Figure 28:
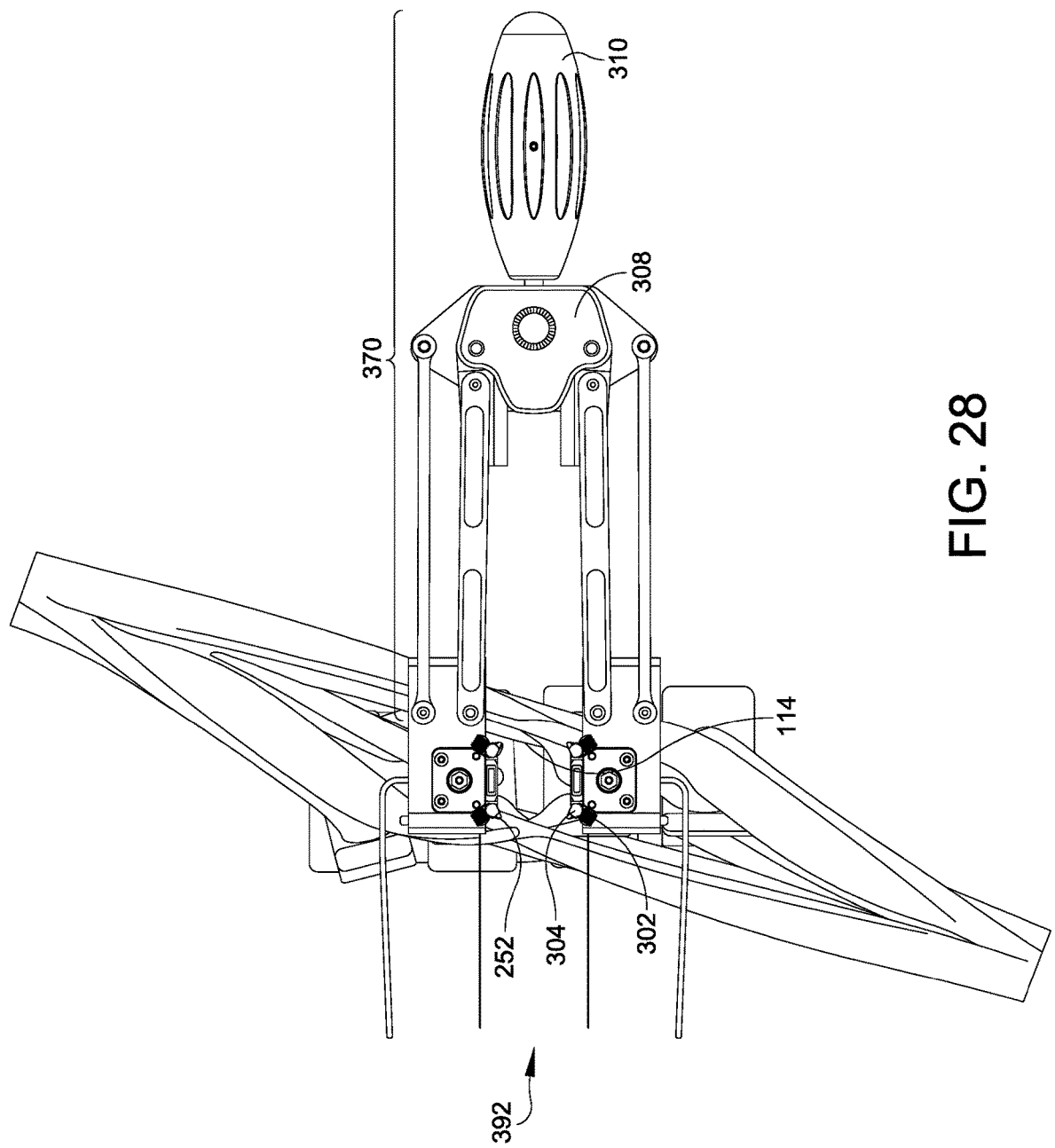
FIG. 28-30 illustrate top views of the two blade subassemblies coupled with the lateral retraction assembly of FIGS. 26-27 in a retracted blade position.
Figure 29:
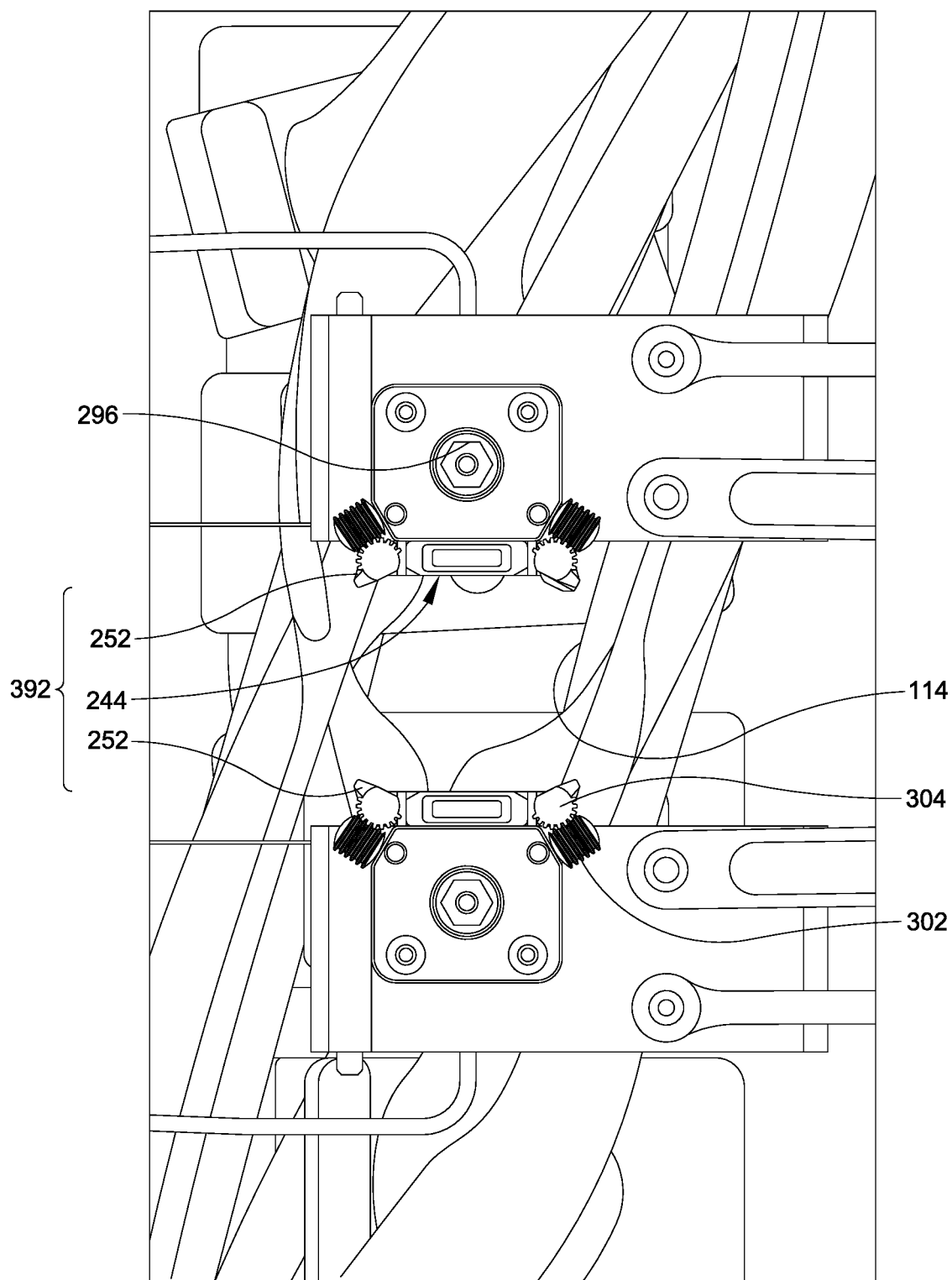

After removal of the K-wire 214, the lower coupling device 242, and the dilator 202, a lateral retraction assembly 370, which, in this embodiment, may include the handle 310, the lateral actuation gearbox 308, the opposing passive lateral arms 344, and the opposing lateral drive arms 354, may be employed to separate or laterally retract the blade subassemblies 240 from a closed position 390, shown in FIGS. 25-27, to a retracted position 392, shown in FIGS. 28-31 (FIG. 35B, 524, 536).

In further detail, FIG. 25 illustrates a perspective view of the lateral retraction assembly 370 having an open housing 342 of the lateral actuation gearbox 308 to detail one embodiment of the mechanics of the gearbox 308. In this embodiment, the handle 310 may incorporate a worm gear 372 at its distal end. The worm gear 372 may be positioned between and enmeshed with two opposing lateral gears 374, one bordering either side of the worm gear 372. Each of the lateral gears 374 may include a pivot point 375 about which the remaining components of the gear 374 rotate, a teeth portion 376 that engages with the worm gear 374, and a drive portion 378 containing a protrusion 362 configured to frictionally fit within the receiver 360 of the second end 358 of one of the lateral drive arms 354.

The teeth portion 376 of each of the lateral gears 374 may have a variable radius that extends between the pivot point 375 and the teeth portion 376. The variable radius may increase from a first radius, $r_1$, located at a first end 380 of the teeth portion 376 to a larger second radius, $r_2$, located at a second end 382 of the teeth portion 376.

In actuating the lateral retraction assembly 370 (FIG. 35B, 536), rotation of the worm gear 372 via the handle 342 causes the enmeshed teeth portions 376 of the opposing lateral gears 374 to travel from the first ends 380 engaged with the worm gear 372 at the smaller radius, $r_1$, to the second ends 382 engaged with the worm gear 372 at the larger radius, $r_2$. This travel causes the lateral gears 374 to pivot about the pivot points 375, such that the drive portions 378 of the gears swing outward in the direction of arrow B as the radius of each lateral gear 374 increases from $r_1$ to $r_2$. This outward trajectory, in turn, drives the lateral drive arms 354, and thus the connected blade subassemblies 240, in the outward direction of arrow B, from the closed position 390 of FIGS. 25-27 to the retracted position 392 of FIGS. 28-31.

Figure 30:
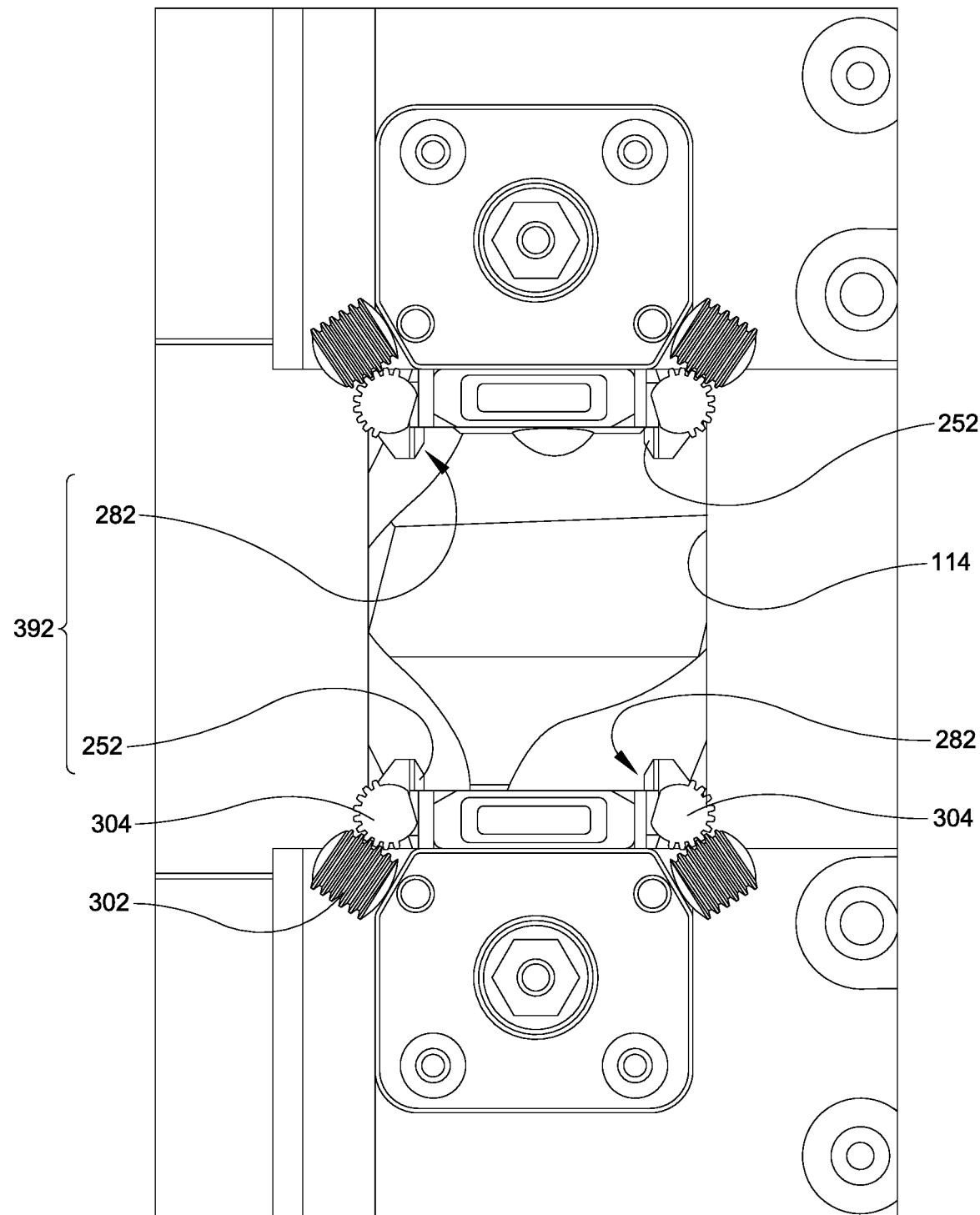
Figure 31:
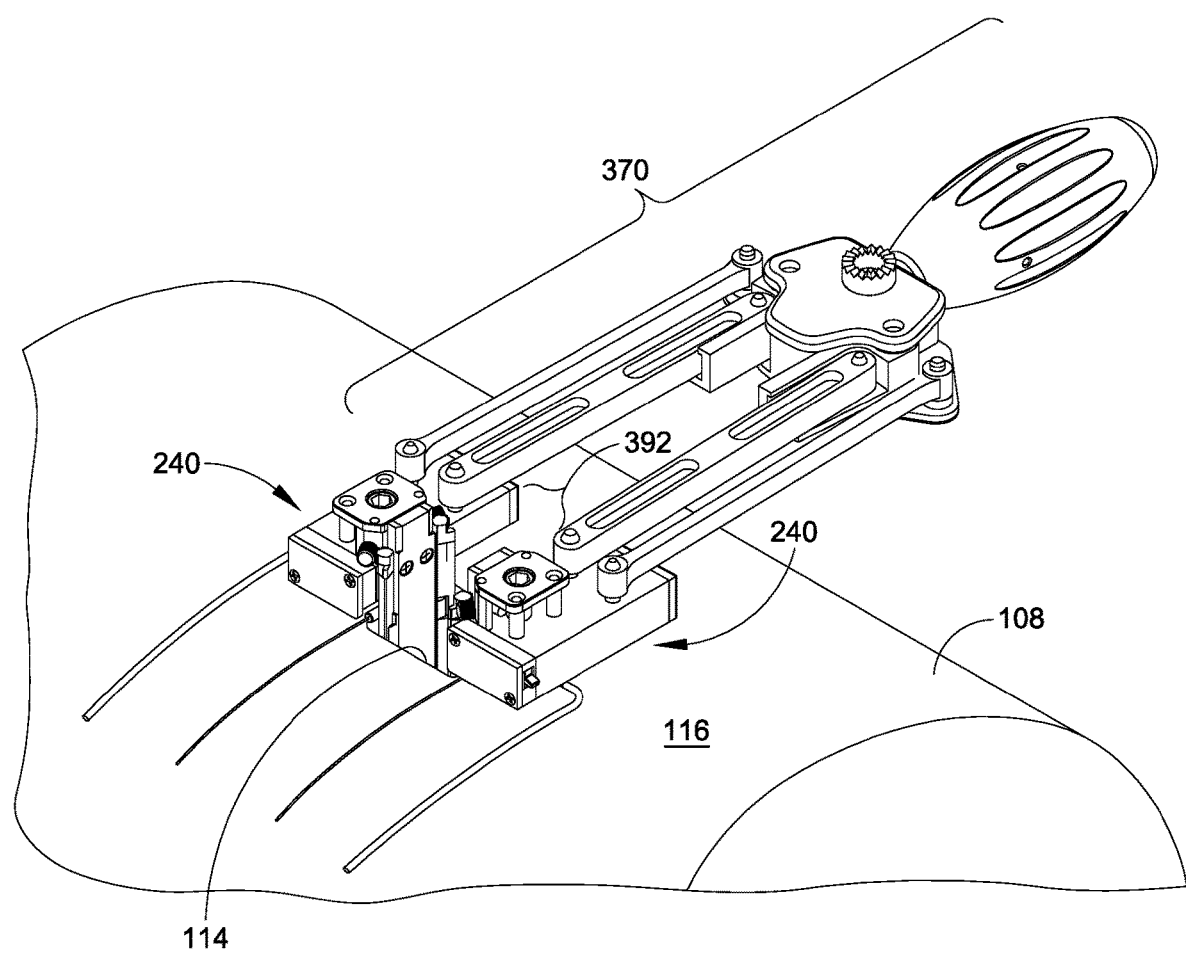
FIG. 31 illustrates a perspective view of the two blade subassemblies coupled with the lateral retraction assembly in the retracted blade position of FIG. 30, as inserted through the patient's side body.

Before, after, or at increments during the process of actuating the lateral retraction assembly 270 (FIG. 35B, 536), and as discussed above in relation to FIGS. 11-13, the wing actuation assembly 290 of each blade subassembly 240 may be employed to adjust the adjustable wings 252 from the open position 280 parallel with the blades 244, shown in FIGS. 25-27, the closed position 282 perpendicular to the blades 244, shown in FIG. 30, and any position therebetween, such as the angled position (e.g., 27 degrees relative the blade 244), shown in FIGS. 28-29 and 31 (FIG. 35B, 538). In this regard, the two opposing blades 244 are sufficient for lateral retraction, without the need for additional blades as required by existing retractor systems, as the adjustable wings 252 prevent creep of the muscle between the blades 244 and into the surgical pathway 114 during retraction. Throughout the steps of rotating the dual-blade assembly 230 from the insertion orientation 239 to the rotated orientation 306 (FIG. 35B, 516), laterally retracting the blade subassemblies 240 from the closed position 390 to the retracted position 392 (FIG. 35B, 524), and adjusting the adjustable wings 252 between the open position 280 and the closed position 282 (FIG. 35B, 538), the active monitoring tips 256 and 283 of the blades 244 and the wings 252, respectively, may be used to provide real-time neuromonitoring to prevent impingement and/or encroachment upon adjacent nerve structures (FIG. 35B, 542).

Figure 32:
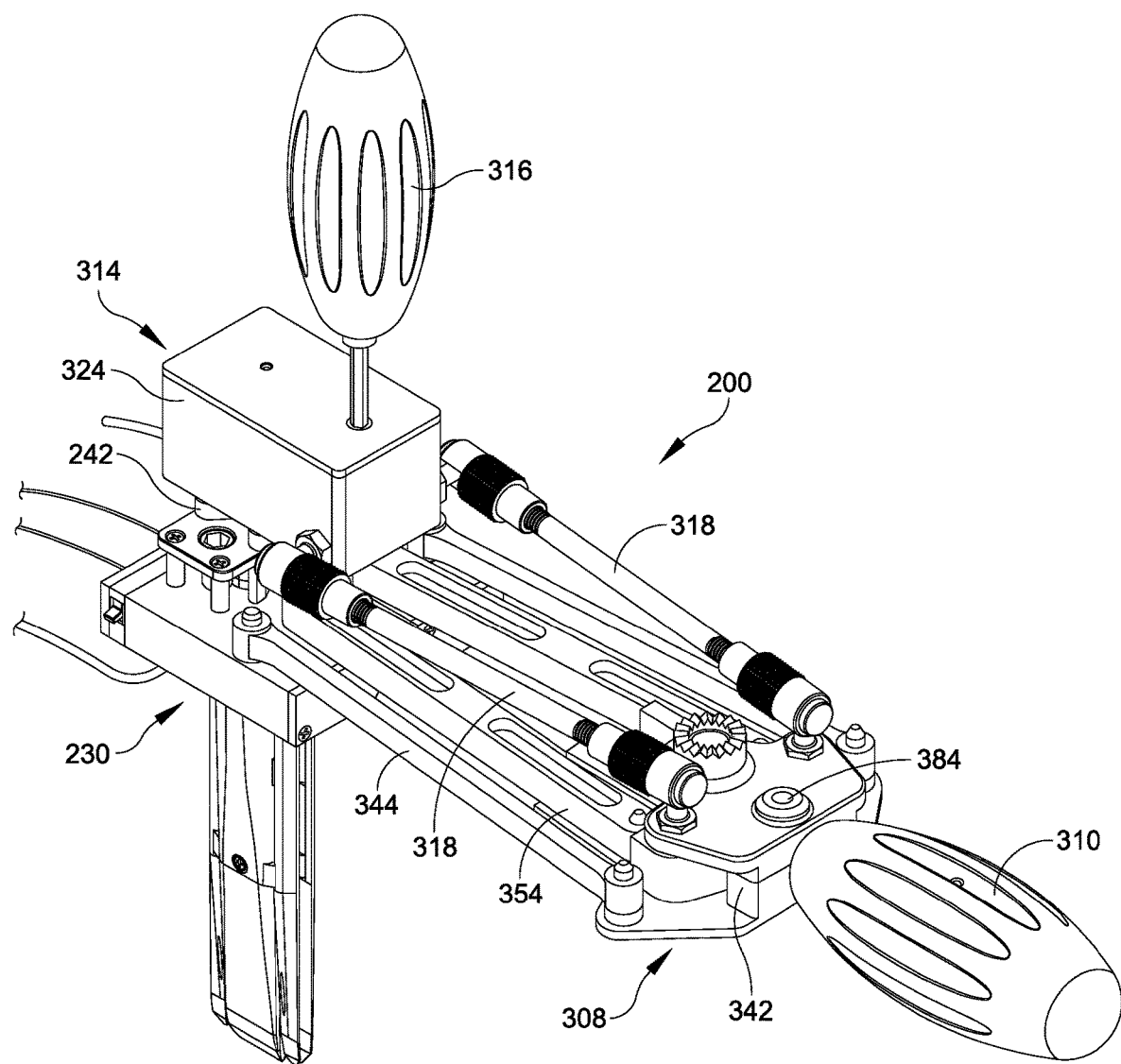
FIG. 32 illustrates a perspective view of one embodiment of a fully assembled lateral retraction system.

FIG. 32 illustrates a perspective view of a fully assembled lateral retractor system 200, including all of the components, assemblies, and subassemblies discussed above. In addition and in this embodiment, the housing 342 of the lateral actuation gearbox 308 may incorporate a level 384 to assist in positioning components of the system 200 when carrying out the disclosed method 500 of creating a surgical pathway 114 using embodiments the lateral retractor system 200, as provided in FIG. 35. The level 384 may be calibrated to level the system with respect to the floor, the surgical table 233, or any appropriate reference plane. Relying on the level 384 for partial positioning reduces the amount of real-time x-ray technology (e.g., fluoroscopy) required to locate the system 200 during operation, resulting in less radiation exposure to the patient, the surgeon, and everyone else in the operating theater. In one embodiment, the level 384 may be a bubble or spirit level, or the level may be a gyroscope.

Figure 33:
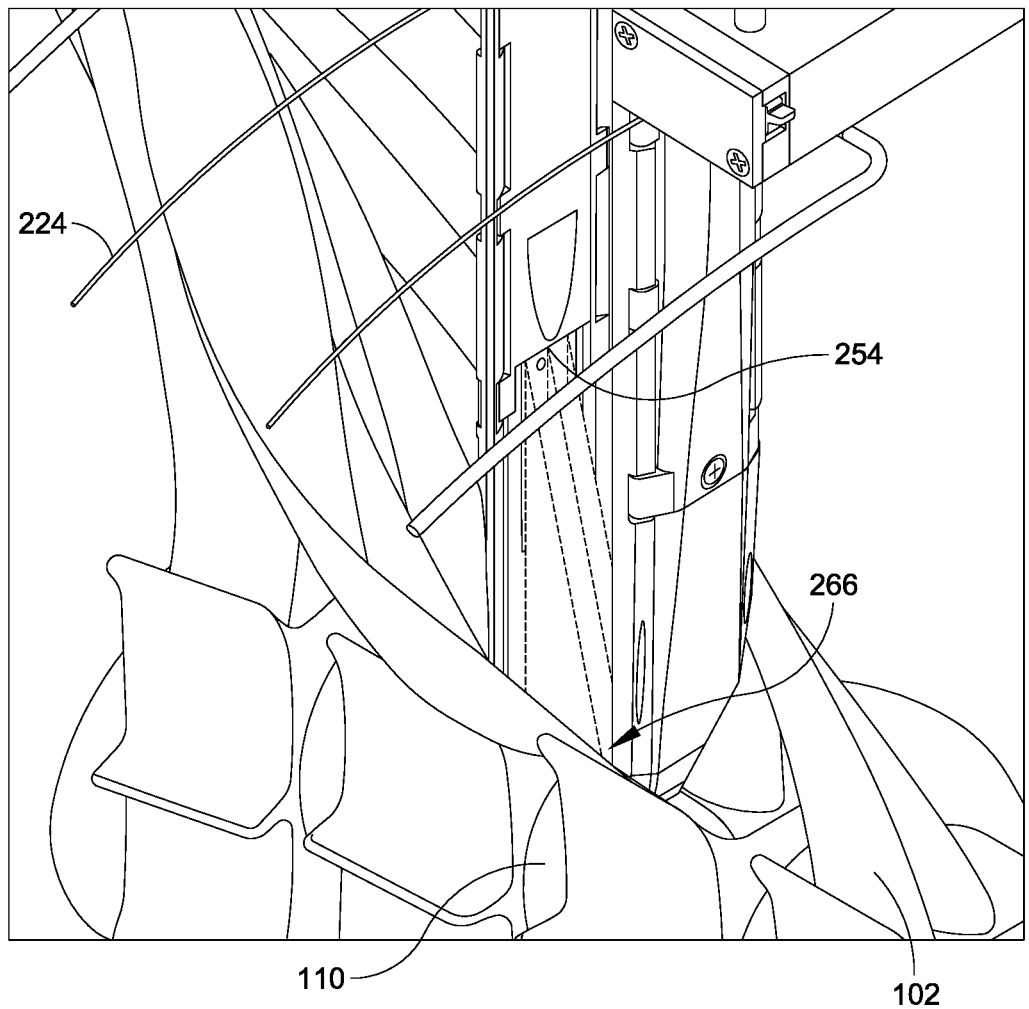
FIG. 33 illustrates a perspective view of a surgical area illuminated using LEDs built into one embodiment of the lateral retraction system of FIG. 32.
Figure 34:
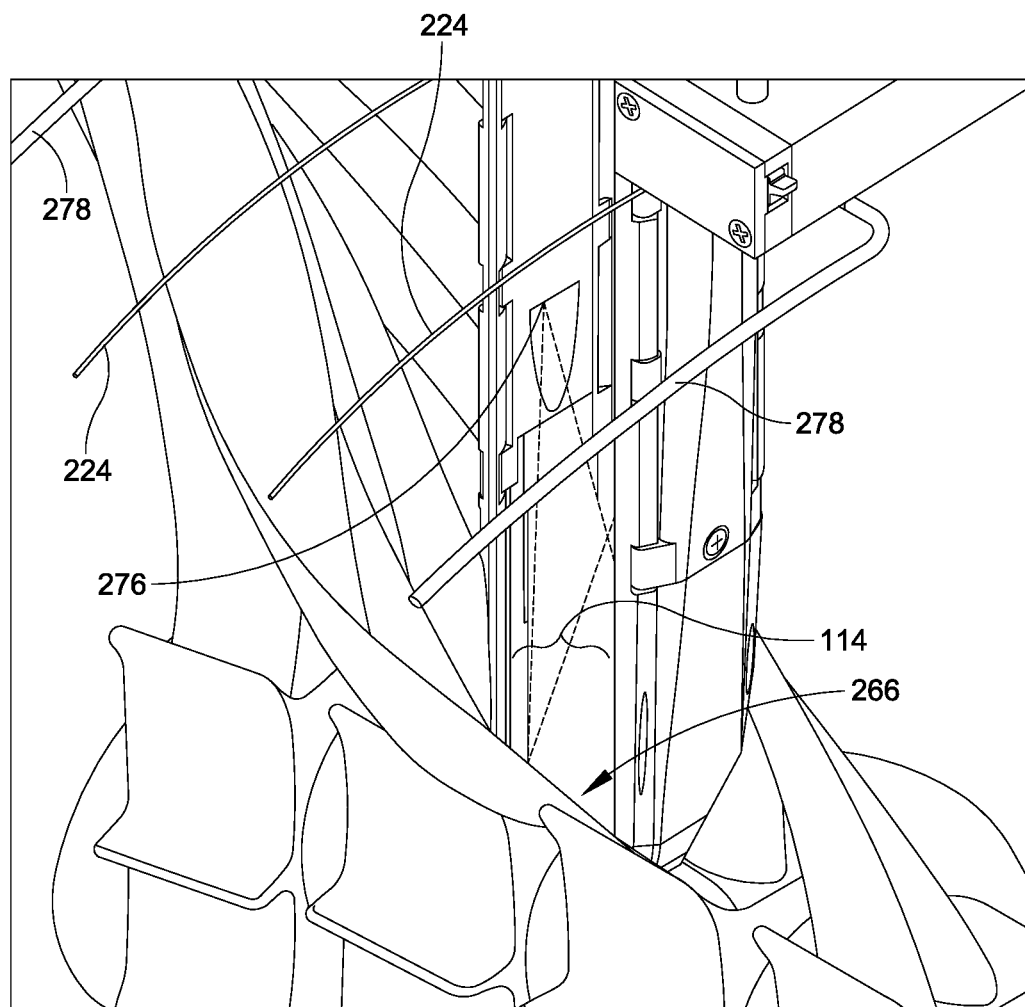
FIG. 34 illustrates a perspective view of an image area covered by a video camera incorporated within one embodiment of the lateral retraction system of FIG. 32.
Figure 35B:
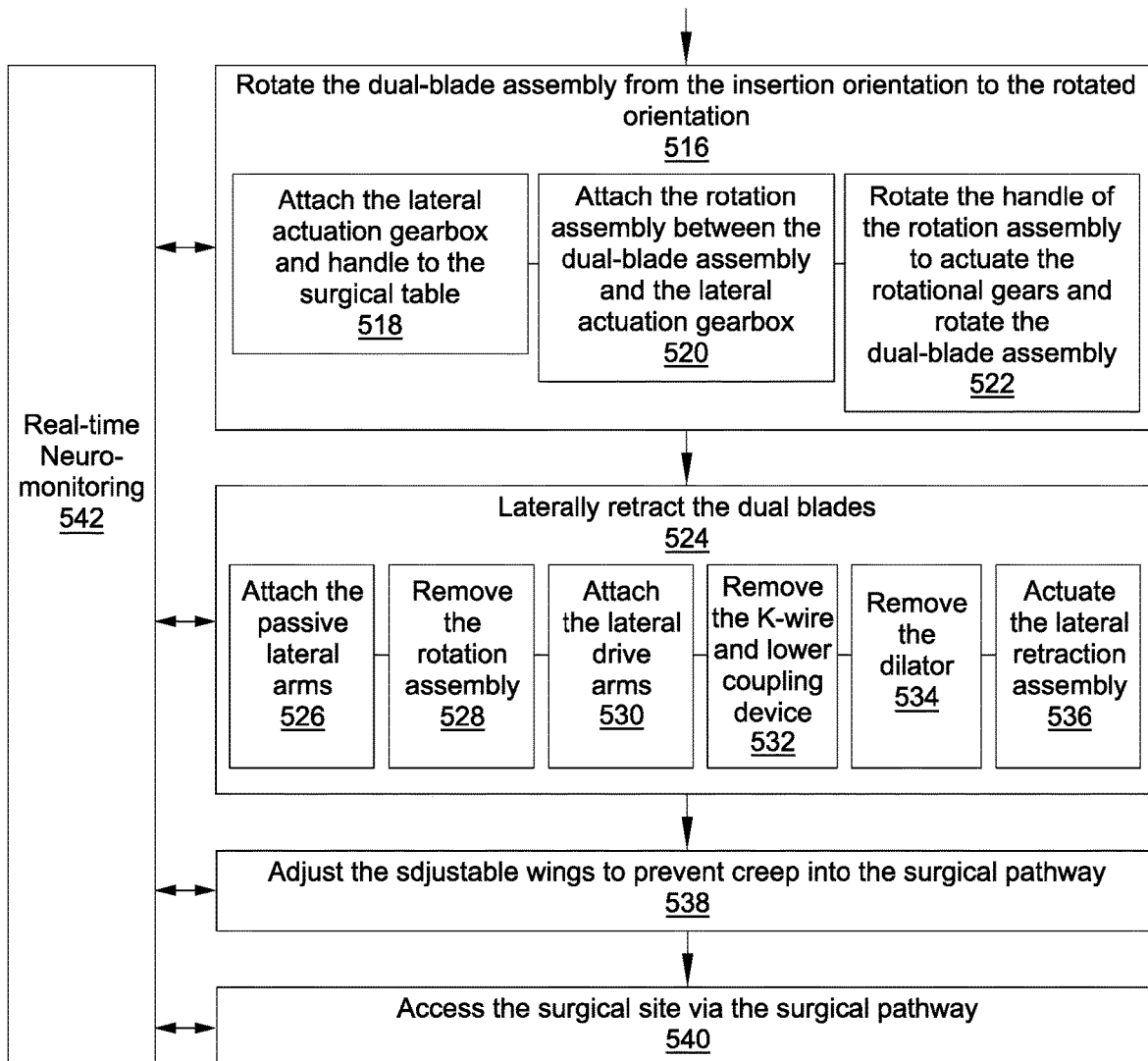

Once the lateral retraction assembly 270 has been employed to retract the blade subassemblies 240 to form the surgical pathway 114, the surgeon may access the spine 100 (FIG. 35B, 540) via the resulting surgical pathway 114, leveraging the LED lights 254 illuminating the surgical area 266 as desired, as shown in FIG. 33, and observing the images transmitted from the surgical area 266 via the video output 278 from the video cameras 276, as shown in FIG. 34.

Each of the components that form embodiments of lateral retractor system 200 discussed above may be formed of any appropriate conductive or nonconductive, autoclavable or otherwise sterilizable metal or plastic using any appropriate manufacturing method. As discussed, some components may be disposable to improve efficiency and customizability and reduce the possibility of disease transmission, while others may be reusable and sterilizable.

Embodiments of the lateral retractor system 200 provide three separate kinds of movement—rotation of the single-component dilator 202 and the dual-blade assembly 230 from the insertion orientation 239 to the final rotated orientation 306, rotation of the adjustable wings 252 from the open position 280 to the closed position 282, and retraction of the blade subassemblies 240 from the closed position 390 to the retracted position 392—that allow for a more sophisticated initial placement of the single-component dilator 202 and the dual-blade assembly 230 in a manner parallel to the psoas muscle 102 and, therefore, less damaging to the muscle and nerve structures adjacent to the patient's spine. Rather than crushing or trapping sensitive body tissues beneath the dilator and/or the blade assembly, the disclosed lateral retractor system enables embodiments of the dilator 102 and the dual-blade assembly 230 to bypass those tissues and instead "separate" them to create the surgical pathway 114, as desired, with the use of an elegant design that features only two blades. In addition, rotation of the flat, narrow dilator 202 allows the dilator 202 to separate the psoas muscle tissues without the need for a more complicated series of progressively larger circular dilators, as required in the prior art.

Further, built-in lighting and video capabilities provide the surgeon with streamlined and flexible lighting of the surgical area and the ability to view his or her actions without hunching over the patient and/or the surgical apparatus. Detachable and disposable distal blade portions and adjustable wings allow the system to accommodate any patient physiology and can be selected in the operating theater as deemed necessary by the surgeon. In sum, the unique lateral retractor system allows for a lateral approach to the spine to be made in a more safe and efficient manner for the patient and for the surgeon.

In addition, continuous, real-time neuromonitoring via the active neuromonitoring tips 222, 256, and 283 located at the distal ends of the dilator 102, the blades 244, and the adjustable wings 252, respectively, further assists in reducing damage to the patient's nerves and plexus in that the system may continuously monitor, and avoid, impingement or encroachment upon nerve structures within a 360-degree monitoring range about the circumference of the system 200. This continuous neuromonitoring occurs throughout the process of forming the surgical pathway 114 and any subsequent surgical procedure.

Figure 36A:
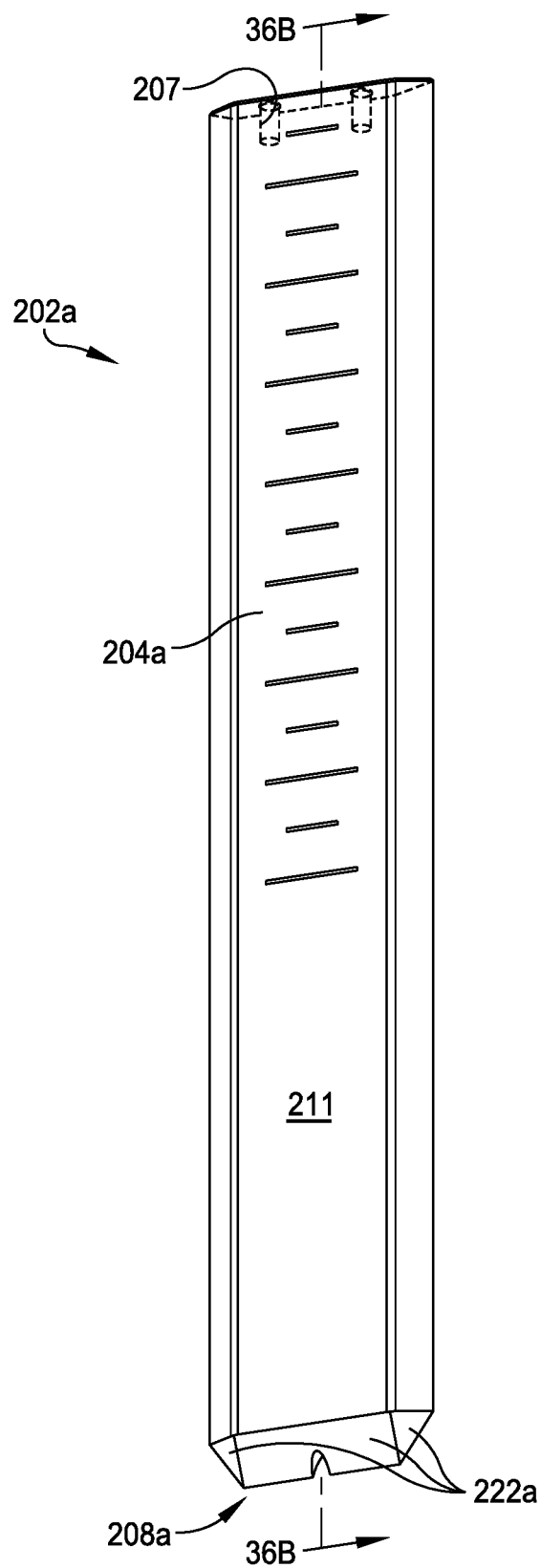
FIGS. 36A-36B illustrate perspective and cross-sectional views of another embodiment of a planar dilator featuring non-wired, continuous, and simultaneous neuromonitoring about 360-degrees of a circumference of the dilator.
Figure 36B:
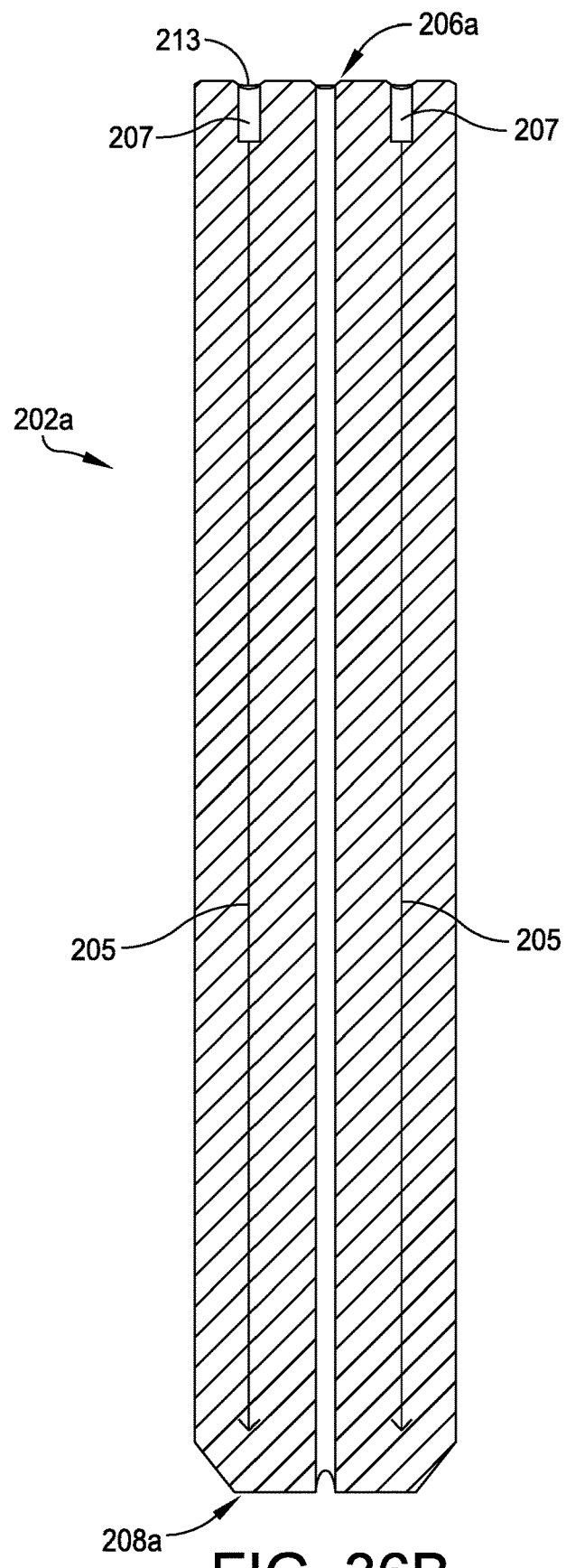

In one embodiment shown in FIGS. 36A-36B, a dilator 202a may be substituted for the dilator 202, discussed above, to provide neuromonitoring capabilities free of internal wires. In this embodiment, the dilator 202a may be formed of a conductive material such as, for example, aluminum and may leverage the internal conductivity of the dilator's rectangular body 204a to form a conductive electrical pathway 205 between one or more conductive input surfaces 207 formed at a proximal end 206a of the rectangular body 204a and a conductive active monitoring tip 222a disposed at a distal end 208a of the rectangular body 204a.

In this embodiment, the electrical pathway 205 may be configured via selective shielding applied to portions of the dilator 202a. For instance, dilator surfaces intended to be nonconductive, insulated surfaces may be coated with an insulative or nonconductive layer. In one embodiment, a portion of an outer surface 211 of the aluminum body 204a may be coated with an anodized layer 213, which may be nonconductive and also provide a hardened surface that resists scratching and other damage to the dilator 202a. In one embodiment, a non-stick material such as Teflon may be added to the anodization to render the anodized layer 213 "slippery" such that the dilator 202a more easily glides relative to other system components and/or bodily tissues during the insertion and removal processes.

In applying the anodized layer 213, portions of the outer surface 211 that are desired to be free of anodization, and thus conductive, may be masked during the anodizing process. In this embodiment, the conductive input surfaces 207 and the active monitoring tip 222a may be masked such that those surfaces remain conductive in their entireties. Thus, when an electrical signal is applied, through the monitoring cable 224 (FIG. 8) or otherwise, to the dilator 202a at the conductive input surfaces 207 at the proximal end 206a of the dilator 202a, the signal travels via the conductive electrical pathway(s) 205 to the active monitoring tip 222a, which spans 360 degrees of the distal end 208a of the dilator 222a.

Impingement or encroachment of the active monitoring tip 222a upon one or more nerve structures causes the nerve structures to fire and generate a responsive signal, which is conducted back through the electrical pathway(s) 205 to the monitoring cable(s) 224 in communication with the electrical pathway(s) 205 at the conductive input surfaces 207, thereby translating the neurosensing stimulation of the active monitoring tip 222a to external monitoring equipment (not shown) via the monitoring cable 224 and determining, in real time, with 360 degrees of monitoring range, and with an internal-wire-free mechanism that is more simply and cost-effectively manufactured, a possibility of nerve or plexus injury as the dilator 202a is inserted (FIG. 35A, 508).

In a manner similar to the dilator, the blades and the adjustable wings may also be configured for continuous, real-time, 360-degree neuromonitoring that does not require a wired electrical pathway within their components. FIGS. 37A-37F illustrate front, rear, and numerous partial views of an exemplary embodiment of a blade 244a, hingedly bordered by two opposing adjustable wings 252a. In operation and in one embodiment, the blade 244a and the wings 252a may be electively substituted for the blade 244 and the wings 252 described above. In this embodiment, the blade 244a and the wings 252a are similar to the blade 244 and the wings 252, discussed above, in both structure and function, and additionally feature no-wire neuromonitoring capabilities similar to the dilator 202a, discussed above in relation to FIGS. 36A-36B.

Figure 37A:
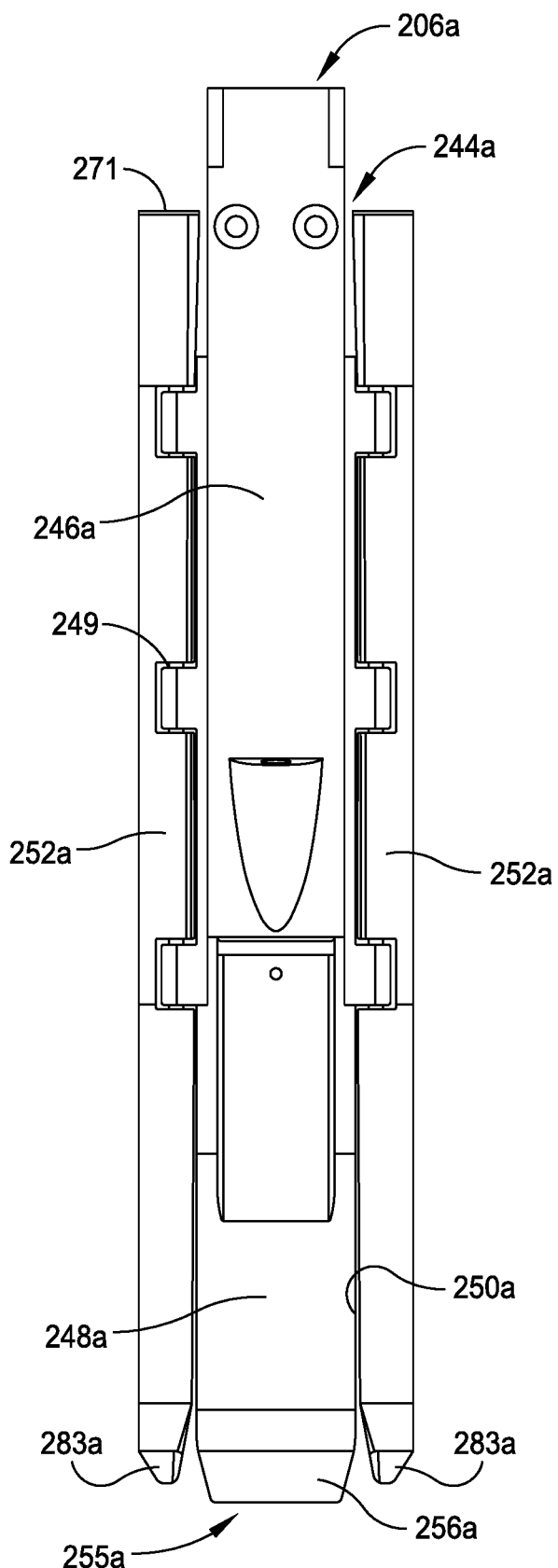
FIGS. 37A-37F illustrate respective front, rear, partial-rear-perspective, partial-side-perspective, unassembled partial-rear perspective, and assembled partial-rear perspective views of one embodiment of a blade and adjustable wings for incorporation into the blade subassembly of FIGS. 11-18, featuring non-wired, continuous, and simultaneous neuromonitoring about 360-degrees of a circumference of the blade and the adjustable wings.
Figure 37B:
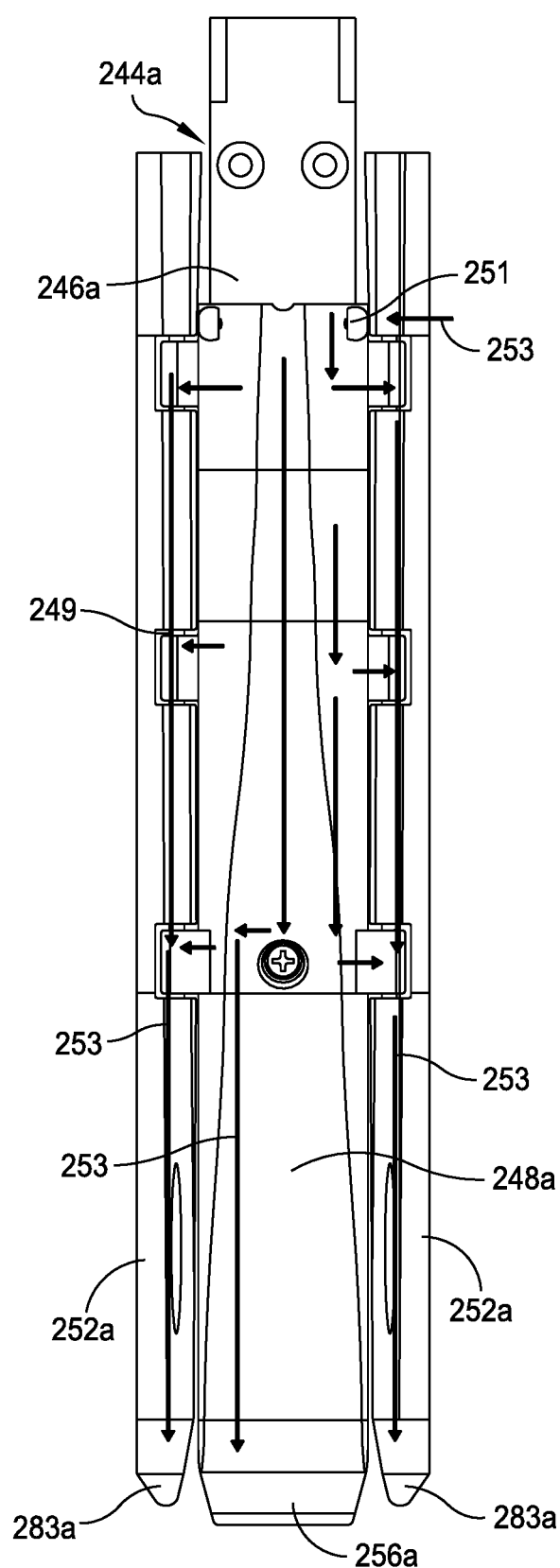
Figure 37C:
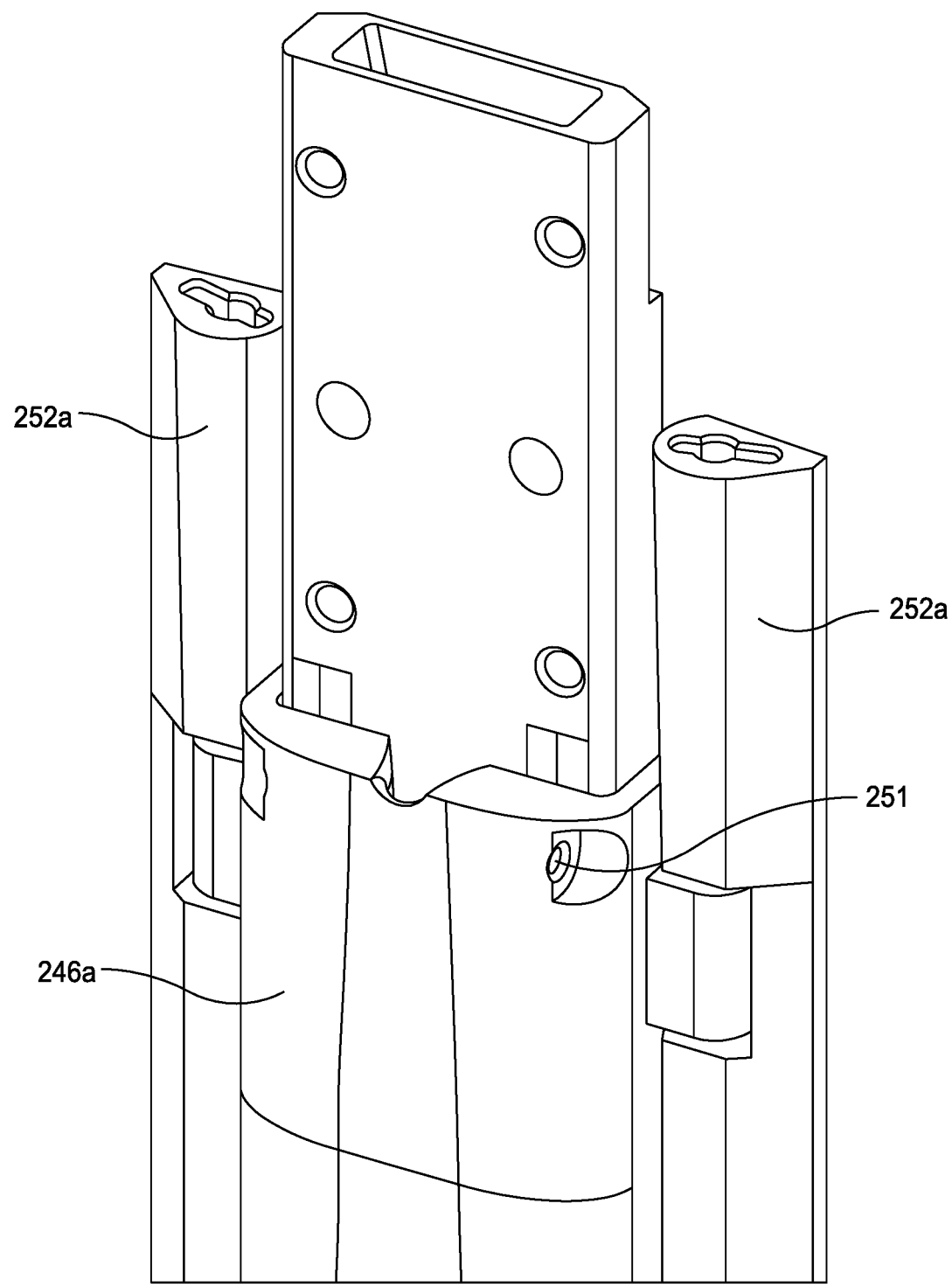
Figure 37D:
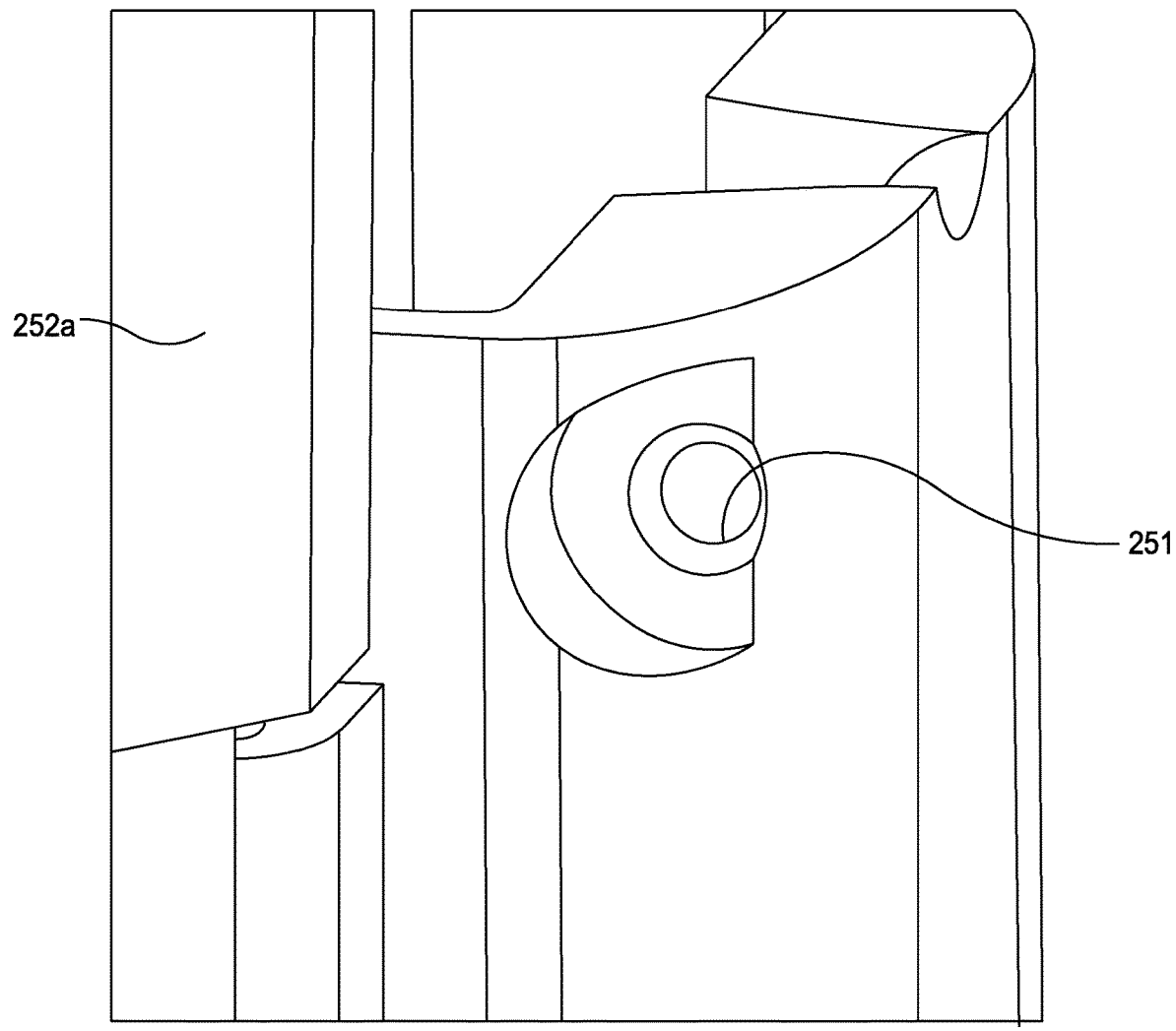

In further detail and as shown in FIGS. 37A-37B, the blade 244a may have a proximal blade portion 246a, a detachable, disposable distal blade portion 248a, and opposing longitudinal edges 250a that extend between a proximal end 260a of the proximal blade portion 246a and a distal end 255a of the distal blade portion 248a. The opposing adjustable wings 252a may be hingedly coupled with each of the opposing longitudinal edges 250a via a plurality of hinge pins 249, as shown in FIGS. 37A-37B.

Figure 37E:
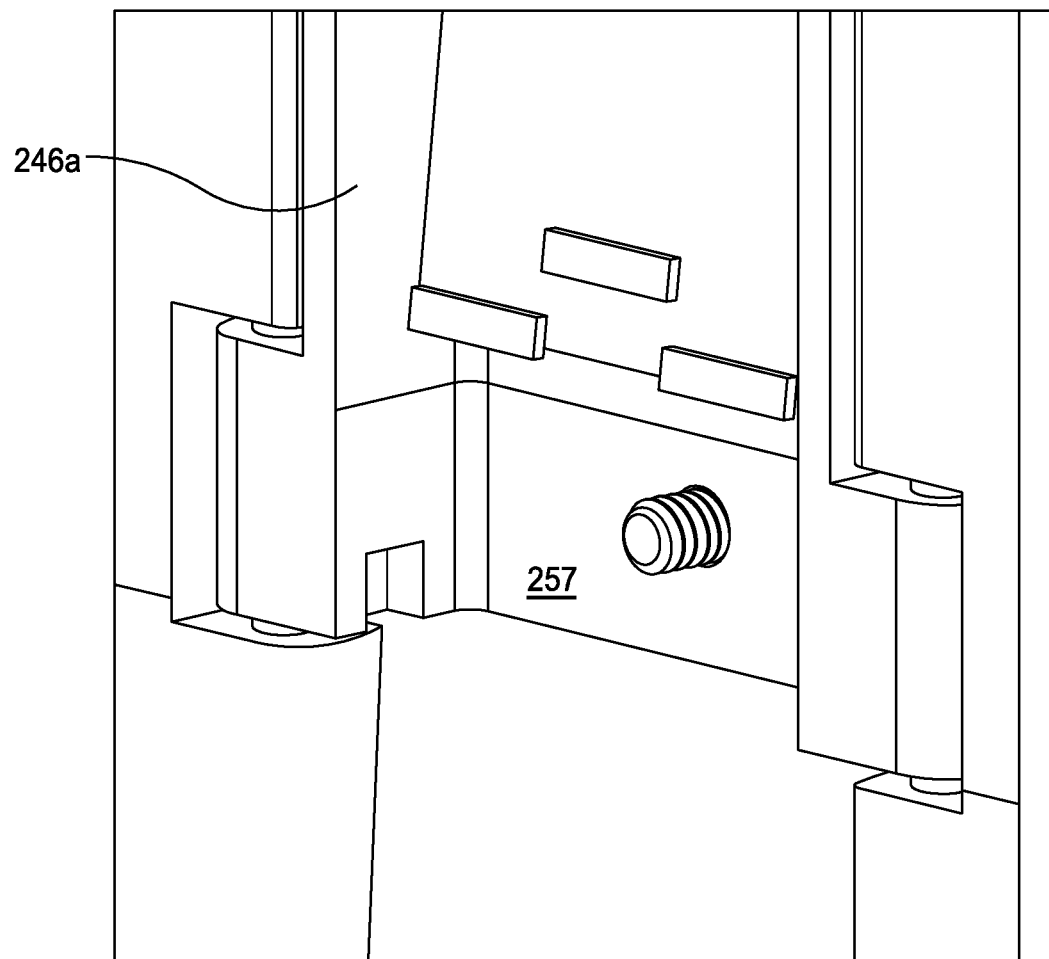
Figure 37F:
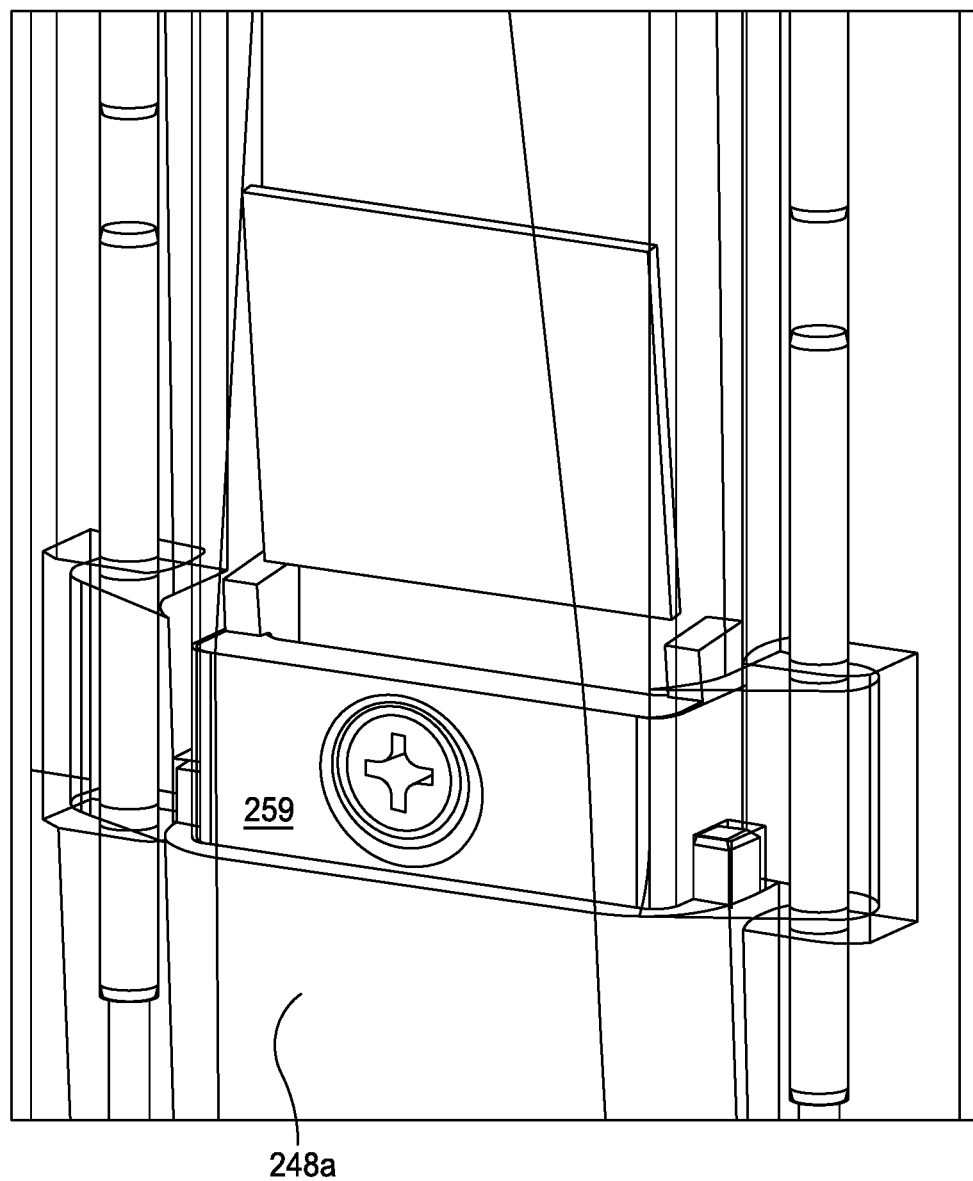

In this embodiment, all components forming the blade 244a and the adjustable wings 252a, including the proximal blade portion 246a, the removeable and disposable distal blade portion 248a, the wings 252a, and the hinge pins 249, may be formed of a conductive material such as, for example, aluminum and may be strategically coated with a nonconductive, insulated layer such as an anodized layer 271 so as to form an internal conductive electrical pathway 253 through the multiple components. In this regard, the proximal portion 246a of the blade 244a may include at least one conductive electrical connection point, conductive input surface, or "jack" 251, shown in FIGS. 37C-37D, and the distal portion 248a of the blade 244a and the opposing adjustable wings 252a may each terminate distally in respective active monitoring tips 256a, 283a similar to the active monitoring tip 222a of the dilator 202a. As shown in FIGS. 37E-37F, select surfaces of the proximal blade portion 246a and the distal blade portion 248a may be masked so as to form adjacent and contacting electrically conductive surfaces 257, 259 when the proximal and distal blade portions 246a, 246b are assembled together.

In operation, the electrical connection point 251 may act as an input point where electrical conduction initiates, via the monitoring cable 224 or another appropriate source, such that an applied electrical signal conducts from the electrical connection point 251, through the proximal blade portion 246a, to and through the wings 252a via the pins 249, to and through the distal blade portion 248a via the conductive surfaces 257, 259, and through the active monitoring tips 256a, 283a along the conductive electrical pathway 253 shown in FIG. 37B. This stimulus of the active monitoring tips 256a, 283a causes nearby nerve structures to fire and generate a responsive electrical signal, which may in turn be conducted back from the active monitoring tips 256a, 283a to the electrical connection point 251 and to the monitoring cable 224 in electronic communication with external monitoring equipment, thereby sensing the stimulation of the active monitoring tips 256a, 283a caused by proximity to nearby nerve structure(s) in real time and with 360 degrees of monitoring range or field of view about an entirety of the distal ends of the blade 244a and the wings 252a. Thus, via the active monitoring tips 256a, 283a of each of the distal blade portions 248a of the blades 244a, continuous real-time neuromonitoring may be performed to prevent nerve or plexus injury when the blade assembly 230 is inserted over the dilator 202a (FIG. 35A, 512, 514), as well as when the blade assembly 230 is rotated (FIG. 35A, 516) and/or laterally separated or retracted (FIG. 35A, 524), as discussed above. Unlike existing systems, neuromonitoring over a full 360-degree monitoring range may continue throughout the procedure.

Due to the multi-component nature of the wings as assembled to the blade, the internal conductive electrical pathway 253 avoids the complexity of a design which routes a wired pathway to the active monitoring tips 256a, 283a, allowing for a more streamlined instrument with fewer components that is more efficient and less expensive to manufacture.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A lateral retractor system for forming a surgical pathway through a plurality of psoas muscle fibers to a patient's intervertebral disc space, comprising:
   A planar dilator for traversing the plurality of the psoas muscle fibers, the planar dilator including:
      a conductive body defined by opposing flat surfaces that extend between a proximal end and a distal end;
      a first nonconductive layer disposed upon an outer surface of the conductive body;
      a first active neuromonitoring tip protruding from the distal end of the conductive body to a leading distal edge configured for insertion into the intervertebral disc space; and
      a first conductive electrical pathway extending from a first conductive input surface at the proximal end of the conductive body, through the conductive body, and to the first active neuromonitoring tip such that an electrical signal applied to the first conductive input surface causes the first active neuromonitoring tip to simultaneously and continuously stimulate one or more nerve structures located adjacent to any portion of a circumference of the distal end of the conductive body to assess for an encroachment of the planar dilator upon the one or more of the nerve structures.

2. The lateral retractor system of claim 1, wherein the first active neuromonitoring tip has a maximum active width that equals a width of the conductive body.

3. The lateral retractor system of claim 1, further comprising a retractable dual-blade assembly having two opposing blade subassemblies, each of the opposing blade subassemblies comprising:
   a conductive blade body having a planar inner-facing surface, an outer-facing surface, and opposing longitudinal edges extending from a proximal end to a distal end of the conductive blade body, the retractable dual-blade assembly configured to pass over the planar dilator such that the planar inner-facing surfaces of the conductive blade bodies contact the opposing flat surfaces of the planar dilator;
   a second nonconductive layer disposed upon an outer surface of the conductive blade body;
   a second active neuromonitoring tip protruding from the distal end of the conductive blade body; and
   a second conductive electrical pathway extending from a second conductive input surface at the proximal end of the conductive blade body, through the conductive blade body, and to the second active neuromonitoring tip such that a second electrical signal applied to the second conductive input surface causes the second active neuromonitoring tip to simultaneously and continuously stimulate one or more nerve structures located adjacent to any portion of a circumference of the distal end of the conductive blade body to assess for an encroachment of the distal end of the conductive blade body upon the one or more of the nerve structures.

4. The lateral retractor system of claim 3, wherein the second active neuromonitoring tip has a maximum active width that equals a width of the conductive blade body.

5. The lateral retractor system of claim 3, each of the opposing blade subassemblies further comprising an adjustable wing rotatively coupled with each of the opposing longitudinal edges of the conductive blade body via at least one conductive hinge, each of the adjustable wings configured to move between an open position parallel to the planar inner-facing surface of the conductive blade body and a closed position perpendicular to the planar inner-facing surface of the conductive blade body, wherein each of the adjustable wings comprises:
   a conductive wing body having a planar inner-facing surface and an outer-facing surface extending from a proximal end to a distal end of the conductive wing body;
   a third nonconductive layer disposed upon an outer surface of the conductive wing body; and
   a third active neuromonitoring tip protruding from the distal end of the conductive wing body, the second conductive pathway extending from the second conductive input surface at the proximal end of the conductive blade body, through the at least one conductive hinge, through the conductive hinge body, and to the third active neuromonitoring tip such that the second electrical signal applied to the second conductive input surface causes the third active neuromonitoring tip to simultaneously and continuously stimulate one or more nerve structures located adjacent to any portion of a circumference of the distal end of the conductive wing body to assess for an encroachment of the conductive wing body upon the one or more of the nerve structures.

6. The lateral retractor system of claim 5, wherein the third active neuromonitoring tip has a maximum active width that equals a width of the conductive wing body.

7. The lateral retractor system of claim 5, wherein the first and the second conductive electrical pathways are free of conductive wiring.

8. The lateral retractor system of claim 5, wherein the conductive body of the planar dilator, each of the conductive blade bodies, and each of the conductive wing bodies are formed of aluminum.

9. The lateral retractor system of claim 5, further comprising a rotation assembly operably coupled to the retractable dual-blade assembly, wherein:
   the rotation assembly is configured to rotate the planar dilator and the retractable dual-blade assembly about a longitudinal center axis of the planar dilator from an insertion orientation in which the opposing flat surfaces of the planar dilator and the planar inner-facing surfaces of the conductive blade bodies are disposed parallel to a grain of the plurality of the psoas muscle fibers to a rotated orientation in which the opposing flat surfaces of the planar dilator and the planar innerfacing surfaces of the conductive blade bodies are disposed parallel to a plane that laterally bisects the intervertebral disc space; and the rotation assembly comprises a rotation gearbox operably coupled to the retractable dual-blade assembly, the rotation gearbox including a gear chain that, when actuated, rotates the planar dilator and the retractable dual-blade assembly about the longitudinal center axis from the insertion orientation to the rotated orientation.

10. The lateral retractor system of claim 9, further comprising a lateral retraction assembly operably coupled with the retractable blade assembly, the lateral retraction assembly configured to retract the two opposing blade subassemblies away from one another, wherein the lateral retraction assembly comprises:

a lateral actuation gearbox operably coupled between each of the two opposing blade subassemblies and a surgical table, the lateral actuation gearbox including a retraction gear chain; and a pair of lateral drive arms, each extending between one of the two opposing blade assemblies and the lateral actuation gearbox, wherein actuation of the retraction gear chain retracts the pair of the lateral drive arms, and thus the two opposing blade assemblies, away from one another.

11. A dilation system for minimizing damage to a patient's psoas muscle fibers when forming a surgical pathway to an intervertebral disc space of the patient's spine, the dilation system having a planar dilator for traversing a plurality of the patient's psoas muscle fibers, the planar dilator including:

a conductive body portion comprising two opposing flat surfaces that extend between a proximal end and distal end;

an insulative coating overlaying the conductive body portion; and a conductive neuromonitoring portion extending distally from the distal end of the conductive body portion to a leading distal edge configured for insertion between the patient's psoas muscle fibers, wherein when an electrical dilator stimulus is applied to the proximal end of the conductive body portion, the electrical dilator stimulus propagates through the conductive body portion to the conductive neuromonitoring portion such that the conductive neuromonitoring portion simultaneously stimulates one or more nerve structures located adjacent to any point about a circumference of the conductive neuromonitoring portion.

12. The dilation system of claim 11, wherein a maximum circumference of the conductive neuromonitoring portion equals a circumference of the conductive body portion.

13. The dilation system of claim 11, further comprising:

a retractable blade assembly comprising opposing detachably-attached blades, each of the opposing detachably-attached blades configured to be passed over the planar dilator on either side of the two opposing flat surfaces of the planar dilator, each of the opposing detachably-attached blades including:

a conductive body portion comprising a planar inner surface and an outer surface that extend between a proximal end and a distal end of each of the opposing detachably-attached blades;

an insulative coating overlaying the conductive body portion of each of the opposing detachably-attached blades; and a conductive neuromonitoring portion extending distally from the distal end of the conductive body portion of each of the opposing detachably-attached blades to a leading distal edge of each of the opposing detachably-attached blades, wherein when an electrical blade stimulus is applied to the proximal end of the conductive body portion of each of the opposing detachably-attached blades, the electrical blade stimulus propagates through the conductive body portion to the conductive neuromonitoring portion of each of the opposing detachably-attached blades such that the conductive neuromonitoring portion of each of the opposing detachably-attached blades simultaneously stimulates one or more nerve structures located adjacent to any point about a circumference of the conductive neuromonitoring portion of each of the opposing detachably-attached blades.

14. The dilation system of claim 13, wherein a maximum circumference of the conductive neuromonitoring portions of the opposing detachably-attached blades equals a circumference of the conductive body portions of the opposing detachably-attached blades.

15. The dilation system of claim 13, further comprising:

an adjustable wing hingedly attached to each longitudinal edge of each of the opposing detachably-attached blades, each of the adjustable wings comprising:

a conductive body portion comprising a planer inner surface and an outer surface that extend between a proximal end and a distal end of each of the adjustable wings;

an insulative coating overlaying the conductive body portion of each of the adjustable wings; and a conductive neuromonitoring portion extending distally from the distal end of the conductive body portion of each of the adjustable wings to a leading distal edge of each of the adjustable wings, wherein when the electrical blade stimulus is applied to the proximal end of the conductive body portion of each of the adjustable wings, the electrical blade stimulus propagates through the conductive body portion to the conductive neuromonitoring portion of each of the adjustable wings such that the conductive neuromonitoring portion of each of the adjustable wings simultaneously stimulates one or more nerve structures located adjacent to any point about a circumference of the conductive neuromonitoring portion of each of the adjustable wings.

16. The dilation system of claim 15, wherein a maximum circumference of the conductive neuromonitoring portions of the adjustable wings equals a circumference of the conductive body portions of the adjustable wings.

17. The dilation system of claim 15, wherein the conductive body portions and the conductive neuromonitoring portions of the planar dilator, the opposing detachably-attached blades, and the adjustable wings are formed from aluminum.

18. A retraction system for forming a surgical pathway through a patient's psoas muscle to the patient's intervertebral disc space, comprising:

a planar dilator for traversing a plurality of fibers of the patient's psoas muscle, the planar dilator having a dilator body portion with opposing flat surfaces and a dilator neuromonitoring portion extending distally from the dilator body portion;

a dual-blade retractor having opposing retractable blades, each of the opposing retractable blades configured to pass over the planer dilator such that each of the opposing retractable blades contacts one of the opposing flat surfaces of the planar dilator, each of the opposing retractable blades having a blade body portion and a blade neuromonitoring portion extending distally from the blade body portion, wherein:

the planar dilator and each of the opposing retractable blades are conductive such that an electrical dilator stimulus applied to the dilator body portion propagates to the dilator neuromonitoring portion and an electrical blade stimulus applied to the blade body portion of each of the opposing retractable blades propagates to each of the blade neuromonitoring portions to simultaneously and continuously stimulate one or more nerve structures located adjacent to any portion of a circumference of the dilator neuromonitoring portion and any portion of a circumference of each of the blade neuromonitoring portions to assess for an encroachment of the planar dilator and the dual-blade retractor upon the one or more of the nerve structures.

19. The retraction system of claim 18, the dual-blade retractor further comprising an adjustable wing rotationally coupled to each longitudinal edge of each of the opposing retractable blades via at least one hinge mechanism, each of the adjustable wings having a wing body portion and a wing neuromonitoring portion extending distally from the wing body portion, wherein the electrical blade stimulus applied to the blade body portion of each of the opposing retractable blades propagates to each of the wing neuromonitoring portions to simultaneously and continuously stimulate one or more nerve structures located adjacent to any portion of a circumference of the wing neuromonitoring portions to assess for an encroachment of the dual-blade retractor upon the one or more of the nerve structures.

20. The retraction system of claim 19, further comprising an insulative dilator coating disposed upon the dilator body portion, an insulative blade coating disposed upon each of the blade body portions, and an insulative wing coating disposed upon each of the wing body portions.

* * * * *